(12) United States Patent
Shultz et al.

(10) Patent No.: US 6,270,974 B1
(45) Date of Patent: *Aug. 7, 2001

(54) EXOGENOUS NUCLEIC ACID DETECTION

(75) Inventors: John William Shultz, Verona; Martin K. Lewis, Madison; Donna Leippe, Middleton; Michelle Mandrekar, Oregon; Daniel Kephart, Cottage Grove; Richard Byron Rhodes, Madison; Christine Ann Andrews, Cottage Grove; James Robert Hartnett; Trent Gu, both of Madison; Ryan J. Olson, Middleton; Keith V. Wood, Madison, all of WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,147

(22) Filed: Sep. 27, 1999

Related U.S. Application Data

(63) Continuation-in-part of application No. 09/358,972, filed on Jul. 21, 1999, which is a continuation-in-part of application No. 09/252,436, filed on Feb. 18, 1999, which is a continuation-in-part of application No. 09/042,287, filed on Mar. 13, 1998.

(51) Int. Cl.[7] ............................. C12Q 1/68; C12P 19/34; G01N 24/00; C07H 19/04
(52) U.S. Cl. ............................. 435/6; 435/7; 435/91.2; 435/91.5; 436/173; 436/501; 536/26; 536/27; 536/28; 935/77; 935/82
(58) Field of Search ..................... 435/6, 7, 91.2, 435/91.5; 436/173, 501; 536/26, 27, 28; 935/77, 82

(56) References Cited

U.S. PATENT DOCUMENTS

| | | | |
|---|---|---|---|
| 4,303,752 | 12/1981 | Kolehmainen et al. | 435/8 |
| 4,331,762 | 5/1982 | Nakajima et al. | 435/190 |
| 4,338,395 | 7/1982 | Leon et al. | 435/17 |
| 4,352,881 | 10/1982 | Inagawa et al. | 435/17 |
| 4,357,420 | 11/1982 | Bostick et al. | 435/8 |
| 4,368,261 | 1/1983 | Klose et al. | 435/15 |
| 4,371,611 | 2/1983 | Fusee | 435/14 |
| 4,394,445 | 7/1983 | Nix et al. | 435/19 |
| 4,415,655 | 11/1983 | De Castro et al. | 435/17 |
| 4,438,124 | 3/1984 | Meister et al. | 424/270 |
| 4,443,594 | 4/1984 | Buckmann | 536/27 |
| 4,446,231 | 5/1984 | Self | 435/7 |
| 4,460,684 | 7/1984 | Bauer | 435/14 |
| 4,485,177 | 11/1984 | Siedel et al. | 436/547 |
| 4,595,655 | 6/1986 | Self | 435/7 |
| 4,683,195 | 7/1987 | Mullis et al. | 435/6 |
| 4,683,202 | 7/1987 | Mullis et al. | 435/91 |
| 4,735,897 * | 4/1988 | Vary et al. | 435/17 |
| 4,743,561 | 5/1988 | Shaffar | 436/501 |
| 4,755,458 | 7/1988 | Rabbani et al. | 435/5 |
| 4,800,159 | 1/1989 | Mullis et al. | 435/172.3 |
| 5,356,776 | 10/1994 | Kambara et al. | 435/6 |
| 5,389,512 | 2/1995 | Sninsky et al. | 435/5 |
| 5,391,480 | 2/1995 | Davis et al. | 435/6 |
| 5,399,491 | 3/1995 | Kacian et al. | 435/6 |
| 5,403,711 | 4/1995 | Walder et al. | 435/6 |
| 5,445,933 | 8/1995 | Eadie et al. | 435/6 |
| 5,494,810 | 2/1996 | Barany et al. | 435/91.52 |
| 5,498,523 | 3/1996 | Tabor et al. | 435/6 |
| 5,512,439 | 4/1996 | Hornes et al. | 435/6 |
| 5,516,663 | 5/1996 | Backman et al. | 435/91.2 |
| 5,530,192 | 6/1996 | Murase et al. | 800/205 |

(List continued on next page.)

FOREIGN PATENT DOCUMENTS

| | | | |
|---|---|---|---|
| 0 229 601 | 11/1986 | (EP) . | |
| 639 647 | 7/1994 | (EP) . | |
| 0 663 447 | 12/1994 | (EP) . | |
| 0 894 867 | 11/1997 | (EP) . | |
| 2055200 | 12/1981 | (GB) | G01N/21/76 |
| WO 90/05530 | 5/1990 | (WO) . | |
| WO 91/17264 | 11/1991 | (WO) . | |
| WO 92/13963 | 8/1992 | (WO) . | |
| WO 94/25619 | 11/1994 | (WO) | C12Q/1/00 |
| WO 95/21938 | 8/1995 | (WO) . | |
| WO 96/41014 | 12/1996 | (WO) . | |
| WO 97/41256 | 11/1997 | (WO) . | |
| WO 98/13523 | 4/1998 | (WO) | C12Q/1/68 |
| WO 98/54362 | 4/1998 | (WO) . | |
| WO 98/28440 | 7/1998 | (WO) | C12Q/1/68 |

OTHER PUBLICATIONS

Most Probable Number (MPN), WQA Glossary of Terms, 3rd Ed., Water Quality Association undated.

P. Nyren, B. Pettersson, and M. Uhlen. "Solid Phase DNA Minisequencing by an Enzymatic Luminometric Inorganic Pyrophosphate Detection Assay," *Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

(List continued on next page.)

*Primary Examiner*—Jeffrey Fredman
*Assistant Examiner*—Arun Chakrabarti
(74) *Attorney, Agent, or Firm*—Welsh & Katz, Ltd.

(57) ABSTRACT

Processes are disclosed using the depolymerization of a nucleic acid hybrid to qualitatively and quantitatively analyze for the presence of a predetermined exogenous nucleic acid. Applications of those processes include the detection of single nucleotide polymorphisms, identification of single base changes, determination of viral load, genotyping, medical marker diagnostics, and the like.

51 Claims, 2 Drawing Sheets

U.S. PATENT DOCUMENTS

| | | | |
|---|---|---|---|
| 5,541,311 | 7/1996 | Dahlberg et al. | 536/23.7 |
| 5,561,044 | 10/1996 | Walker et al. | 435/6 |
| 5,573,906 | 11/1996 | Bannwarth et al. | 435/6 |
| 5,622,824 | 4/1997 | Koster et al. | 435/6 |
| 5,648,232 | 7/1997 | Squirrell | 435/34 |
| 5,660,988 | 8/1997 | Duck et al. | 435/6 |
| 5,667,964 | 9/1997 | Ho | 435/5 |
| 5,683,877 | 11/1997 | Lu-Chang et al. | 435/6 |
| 5,691,146 | 11/1997 | Mayrand | 435/6 |
| 5,723,591 | 3/1998 | Livak et al. | 536/22.1 |
| 5,731,146 | 3/1998 | Duck et al. | 435/6 |
| 5,736,365 | 4/1998 | Walker et al. | 435/91.2 |
| 5,741,635 | 4/1998 | Boss et al. | 435/4 |
| 5,759,820 | 6/1998 | Hornes et al. | 435/91.1 |
| 5,763,181 | 6/1998 | Han et al. | 435/6 |
| 5,766,849 | 6/1998 | McDonough et al. | 435/6 |
| 5,786,139 | 7/1998 | Burke et al. | 435/6 |
| 5,786,183 | 7/1998 | Ryder et al. | 435/91.2 |
| 5,814,491 | 9/1998 | Vijg et al. | 435/91.2 |
| 5,824,517 | 10/1998 | Cleuziat et al. | 435/91.2 |
| 5,834,202 | 10/1998 | Auerbach | 435/6 |
| 5,840,873 | 11/1998 | Nelson et al. | 536/24.3 |
| 5,843,660 | 12/1998 | Schumm et al. | 435/6 |
| 5,849,547 | 12/1998 | Cleuziat et al. | 435/91.21 |
| 5,853,981 | 12/1998 | Kondo et al. | 435/5 |
| 5,854,033 | 12/1998 | Lizardi | 435/91.2 |
| 5,861,242 | 1/1999 | Chee et al. | 435/5 |
| 5,863,736 | 1/1999 | Haaland | 435/6 |
| 5,866,337 | 2/1999 | Schon | 435/6 |
| 5,869,252 | 2/1999 | Bouma et al. | 435/6 |
| 5,871,902 | 2/1999 | Weininger et al. | 435/5 |
| 5,876,924 | 3/1999 | Zhang et al. | 435/5 |
| 5,876,930 | 2/1999 | Livak et al. | 435/6 |
| 5,876,978 | 3/1999 | Willey et al. | 435/91.2 |
| 5,880,473 | 3/1999 | Ginestet | 250/458.1 |
| 5,882,856 | 3/1999 | Shuber | 435/6 |
| 5,885,775 | 3/1999 | Haff et al. | 435/6 |
| 5,888,819 | 3/1999 | Goelet et al. | 435/5 |
| 5,902,722 | 5/1999 | Di Cesare et al. | 435/4 |
| 6,007,987 | 12/1999 | Cantor et al. | 435/6 |
| 6,066,483 | 5/2000 | Riggs et al. | 435/194 |

OTHER PUBLICATIONS

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerse chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70:79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2):237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1988).

P. Nyren, et al., *Anal. Biochem.*, 244:367–373 (1997).

S. Borman, "Developers of Novel DNA Sequencers Claim Major Performance Advances", *C &EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

A.E. Sippel, "Purification and Characterization of Adenosine Triphosphate: Ribonucleic Acid Adenyltransferase from *Escherichia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Bioluminometric Method for Real–Time Detection of Reverse Transcriptase Activity", *Biotechniques*, 24:302–306 (Feb., 1998).

B. Hove–Jensen, K.W. Harlow, C.J. King, R.L. Switzer, "Phosphoribosylpyrophospate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.,* 220:219–21 (1994).

S. Tabor and C.C. Richardson, "DNA Sequence Analysis With a Modified Bacteriophage T7 DNA Polymerase", *J. Biol. Chem.,* 265(14):8322–8328 (1990).

R.S. Chittock, J.–M. Hawronsky, J. Holah and C.W. Wharton, "Kinetic Aspects of ATP Amplification Reactions", *Anal. Biochem.,* 255:120–126 (Jan. 1, 1998).

Kung, et al., "Picogram Quantitation ofTotal DNA Using DNA–Binding Proteins in a Silicon Sensor–Based System", *Anal. Biochem.,* 187:220–227 (1990).

Srivastavan & Modak, *J. Biol. Chem.,* 255(5):2000–2004 (1980).

Sano & Feix, *Eur. J. Biochem.,* 71:577–583 (1976).

Sabina, et al., *Science,* 223:1193–1195 (1984).

Parks & Agarwal in *The Enzymes,* vol. 9:307–333, P. Boyer Ed. (1973).

Shimofuruya & Suzuki, *Biochem. Intl.,* 26(5):853–861 (1992).

Nyren, et al., "Detection of Single–Base Changes Using a Bioluminomeatric Primer Extension Assay", *Anal. Biochem.,* 244:367–373 (1977).

P. Bernard et al., *Am. J. Pathol.,* 153:1055–1061 (1998).

G. Garinis et al., *J. Clin. Lab. Anal.,* 13:122–125 (1999).

Holguin, et al., *Eur. J. Clin. Microbiol. Infect. Dis.,* 18:256–259 (1999).

Boriskin, et al., *Arch. Dis. Child.,* 80:132–136 (1999).

de Vega, et al., "Primer Terminus Stabilizing at the 3'–5' exonuclease active site of _29 DNA polymerase. Involvement of two amino acid residues highly conserved in proofreading DNA polymerases", *EMBO J.,* 15(5):1182–1192 (1996).

S. Patel et al., *Biochemistry,* 30:511–525 (1991).

I. Wong et al., *Biochemistry,* 30:526–537 (1991).

S. Zinnen et al., *J. Biological Chemistry,* 269(39):24195–24202 (1994).

J. Lindquist, Dept. of Bacteriology, University of Wisconsin–Madison,http://www.bact.wisc.edu/bact102/102dil3, 3a.html undated.

Newton et al., *Nucl. Acids Res.,* 17:2503–2516 (1989).

Wu et al., *Proc. Natl. Acad. Sci., USA,* 86:2757–2760 (1989).

T. Nikiforov, et al., *Nucl. Acids Res.,* 22:4167–4175 (1994).

C. Wittwer, et al., *Biotechniques,* 22:130–138 (1997).

P. Holland, et al., *Proc. Natl. Acad. Sci., USA,* 88:7276–7280 (1991).

R. Kramer, et al., *Nat. Biotechnol.,* 14:303–308 (1996).

J. Schultz, D. Leippe, K. Lewis and M. Nelson, "Non–radioactive Measurement of DNA Using Coupled Enzymatic Reactions", Presentation Mar. 16–20, 1998 at a Parenteral Drug Association meeting in San Francisco, California.

Seq ID No. 1, "Blast Archaeal Gemone Sequences at Center of Marine Biotechnology" Online, May 21, 1999, Retrieved on 8/7/200 @ http://Combdna.umbi.umd.edu/bags.html. http://Comb5–156.umbi.umd.edu/cgi–bin/PfurGene-.PL?GeneID=894645&Dataset=Nayb&Geneidtxt–994645, Online! XP002144446, Retrieved from the internet on 2000–08–07.

Giartosio, et al., "Thermal stability of hexameric and tetrameric nucleoside diphosphate kinases: Effect of subunit interaction", *J. Biol. Chem.,* 271(30)17845–17851 (1996).

Bi. W., et al., "Detection of known mutation by proof–reading PCR", *Nucleic Acid Research,* GB 26(12):3073–3075 (1998).

Kawarabayashi, et al., "Complete Sequence and Gene Organization of the Genorne of hyper–thermophilic Archaebacteriurn, *Pyrococcus horikoshii* OT3", *DNA Research,* 5:55–76 (1998).

* cited by examiner

Fig. 1

A Wild Type Template

```
3'    CTGAGCAGTACAGAGTCGAAATC 5' 10866(SEQ ID NO:81)
      TCTGACTCGTCATGTCTCAGCTTTAGTTTAATACGACTCACTATAG
      T                                           G
      A                                           G
      GTCTCTTTCTGTTATATCAAG 5'  3' TCCACCTTAGTGTGACTC 10865(SEQ ID NO:76)
5' TTGCAGAGAAAGACAATATAGTTCTTGGAGAAGGTGGAATCACACTGAGTGGA 10870(SEQ ID NO:77)
                         3' CCACTTCCACCTTAGTGTGACTC 5' 10869(SEQ ID NO:79)
```

B Mutant Template

```
3'    CTGAGCAGTACAGAGTCGAAATC 5' 10866(SEQ ID NO:81)
      TCTGACTCGTCATGTCTCAGCTTTAGTTTAATACGACTCACTATAG
      T                                           G
      A                                           G
      GTCTCTTTCTGTTATATCAAG 5'  3' TCCACCTTAGTGTGACTC 10865(SEQ ID NO:76)
5' TTGCAGAGAAAGACAATATAGTTCTTTGAGAAGGTGGAATCACACTGAGTGGA 10994(SEQ ID NO:78)
                     3' ACACTTCCACCTTAGTGTGACTC 5' 10989(SEQ ID NO:80)
```

Fig. 2

A.
5'...CCCGGAGAGACCTCCTTAAGGGGCCATATTATTCGTCGATTCCAGTGTTGGCCAAACGG
                                                              A—T...3'
       3'AGCTAAGGTCACAACCGGTTTGCCGCTTTATTATACCGGGG 5'
                                    SEQ ID NO:68
SEQ ID NO:67

B.
5'...CCCGGAGAGACCTCCTTAAGGGGCCATATTATTCGTCGATTCCAGTGTTGGCCAAACGG
                                                              A—T...3'
3'...GGGCCTCTCTGGAGGAATTCCCGGTATAATAAAGCAGCTAAGGTCACAACCGGTTTGCCGCTTTATTATACCGGGG 5'
SEQ ID NO:67                                                  SEQ ID NO:69

C.
                                      →
5'  CCCGGAGAGACCTCCT 3'
3'  GGGCCTCTCTGGAGGAATTCCCGGTATAATAAAGCAGCTAAGGTCACAACCGGTTTGCCGCTTTATTATACCGGGG 5'
SEQ ID NO:70                                                  SEQ ID NO:69

D.
                                      →
5'  CCCGGAGAGACCTCCTTAAGGGGCCATATTATTTCGTCGATTCCAGTGTTGGCCAAACGGGCGAAATATGGCCCC 3'
3'  GGGCCTCTCTGGAGGAATTCCCGGTATAATAAAGCAGCTAAGGTCACAACCGGTTTGCCGCTTTATTATACCGGGG 5'
SEQ ID NO:71                                                  SEQ ID NO:69

E.
                                      →
3'                                    CCCCGGTATAATAAGC
5'  CCCGGAGAGACCTCCTTAAGGGGCCATATTATTTCGTCGATTCCAGTGTTGGCC
SEQ ID NO:71

SEQUENCE LISTING

<160> NUMBER OF SEQ ID NOS: 92

<210> SEQ ID NO 1
<211> LENGTH: 74
<212> TYPE: DNA
<213> ORGANISM: Cytomegalovirus

<400> SEQUENCE: 1
cgcttctacc acgaatgctc gcagaccatg ctgcacgaat acgtcagaaa gaacgtggag    60
cgtctgttgg agct                                                       74

<210> SEQ ID NO 2
<211> LENGTH: 74
<212> TYPE: DNA
<213> ORGANISM: Cytomegalovirus

<400> SEQUENCE: 2
ccaacagacg ctccacgttc tttctgacgt attcgtgcag catggtctgc gagcattcgt    60
ggtagaagcg agct                                                       74

-continued

```
<210> SEQ ID NO 3
<211> LENGTH: 74
<212> TYPE: DNA
<213> ORGANISM: mutant Cytomegalovirus

<400> SEQUENCE: 3
cgcttctacc acgaatgctc gcagatcatg ctgcacgaat acgtcagaaa gaacgtggag      60
cgtctgttgg agct                                                       74

<210> SEQ ID NO 4
<211> LENGTH: 74
<212> TYPE: DNA
<213> ORGANISM: mutant Cytomegalovirus

<400> SEQUENCE: 4
ccaacagacg ctccacgttc tttctgacgt attcgtgcag catgatctgc gagcattcgt      60
ggtagaagcg agct                                                       74

<210> SEQ ID NO 5
<211> LENGTH: 21
<212> TYPE: DNA
<213> ORGANISM: Cytomegalovirus

<400> SEQUENCE: 5
ctaccacgaa tgctcgcaga c                                               21

<210> SEQ ID NO 6
<211> LENGTH: 21
<212> TYPE: DNA
<213> ORGANISM: Cytomegalovirus

<400> SEQUENCE: 6
ctaccacgaa tgctcgcaga t                                               21

<210> SEQ ID NO 7
<211> LENGTH: 21
<212> TYPE: DNA
<213> ORGANISM: Cytomegalovirus

<400> SEQUENCE: 7
tgacgtattc gtgcagcatg g                                               21

<210> SEQ ID NO 8
<211> LENGTH: 21
<212> TYPE: DNA
<213> ORGANISM: Cytomegalovirus

<400> SEQUENCE: 8
tgacgtattc gtgcagcatg a                                               21

<210> SEQ ID NO 9
<211> LENGTH: 70
<212> TYPE: DNA
<213> ORGANISM: Listeria

<400> SEQUENCE: 9
gaagtaaaac aaaactacaca agcaactaca cctgcgccta aagtagcaga aacgaaagaa    60
actccagtag                                                            70

<210> SEQ ID NO 10
<211> LENGTH: 70
<212> TYPE: DNA
```

-continued

<213> ORGANISM: Listeria

<400> SEQUENCE: 10
ctactggagt tctttcgtt tctgctactt taggcgcagg tgtagttgct tgtgtagttt    60
gttttacttc                                                          70

<210> SEQ ID NO 11
<211> LENGTH: 30
<212> TYPE: DNA
<213> ORGANISM: Listeria

<400> SEQUENCE: 11
gcaactacac ctgcgcctaa agtagcagaa                                    30

<210> SEQ ID NO 12
<211> LENGTH: 30
<212> TYPE: DNA
<213> ORGANISM: Listeria

<400> SEQUENCE: 12
ttctgctact taggcgcag gtgtagttcg                                     30

<210> SEQ ID NO 13
<211> LENGTH: 70
<212> TYPE: DNA
<213> ORGANISM: Listeria

<400> SEQUENCE: 13
catcgacggc aacctcggag acttacgaga tattttgaaa aaaggcgcta cttttaatcg    60
agaaacacca                                                          70

<210> SEQ ID NO 14
<211> LENGTH: 70
<212> TYPE: DNA
<213> ORGANISM: Listeria

<400> SEQUENCE: 14
tggtgtttct cgattaaaag tagcgccttt tttcaaaata tctcgtaagt ctccgaggtt    60
gccgtcgatg                                                          70

<210> SEQ ID NO 15
<211> LENGTH: 30
<212> TYPE: DNA
<213> ORGANISM: Listeria

<400> SEQUENCE: 15
ctcggagact tacgagatat tttgaaaaaa                                    30

<210> SEQ ID NO 16
<211> LENGTH: 30
<212> TYPE: DNA
<213> ORGANISM: Listeria

<400> SEQUENCE: 16 tttttcaaa atatctcgta agtctccgag                                     30

<210> SEQ ID NO 17
<211> LENGTH: 60
<212> TYPE: DNA
<213> ORGANISM: Salmonella

<400> SEQUENCE: 17
tttaattccg agcctgtgt aatgaaagaa atcaccgtca ctgaacctgc ctttgtcacc    60

<210> SEQ ID NO 18
<211> LENGTH: 60
<212> TYPE: DNA
<213> ORGANISM: Salmonella

<400> SEQUENCE: 18
ggtgacaaag gcaggttcag tgacggtgat ttctttcatt acacaggctc cggaattaaa    60

<210> SEQ ID NO 19
<211> LENGTH: 30
<212> TYPE: DNA
<213> ORGANISM: Salmonella

<400> SEQUENCE: 19
tgtgtaatga agaaatcac cgtcactgaa    30

<210> SEQ ID NO 20
<211> LENGTH: 30
<212> TYPE: DNA
<213> ORGANISM: Salmonella

<400> SEQUENCE: 20
ttcagtgacg gtgatttctt tcattacaca    30

<210> SEQ ID NO 21
<211> LENGTH: 24
<212> TYPE: DNA
<213> ORGANISM: kanamycin RNA oligo

<400> SEQUENCE: 21
gcaacgctac ctttgccatg tttc    24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: PROBE FOR
      KANAMYCIN RNA, ALTERED AT 3' TERMINUS

<400> SEQUENCE: 22
gcaacgctac ctttgccatg tttg    24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: PROBE TO
      KANAMYCIN RNA, ALTERED AT 3' TERMINUS

<400> SEQUENCE: 23
gcaacgctac ctttgccatg ttta    24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: PROBE TO
      KANAMYCIN RNA, ALTERED AT 3' TERMINUS

<400> SEQUENCE: 24

```
gcaacgctac ctttgccatg tttt                                          24

<210> SEQ ID NO 25
<211> LENGTH: 30
<212> TYPE: DNA
<213> ORGANISM: rabbit

<400> SEQUENCE: 25
atggtgcatc tgtccagtga ggagaagtct                                    30

<210> SEQ ID NO 26
<211> LENGTH: 30
<212> TYPE: DNA
<213> ORGANISM: rabbit

<400> SEQUENCE: 26
agacttctcc tcactggaca gatgcaccat                                    30

<210> SEQ ID NO 27
<211> LENGTH: 26
<212> TYPE: DNA
<213> ORGANISM: rabbit

<400> SEQUENCE: 27
gctgctggtt gtctacccat ggaccc                                        26

<210> SEQ ID NO 28
<211> LENGTH: 26
<212> TYPE: DNA
<213> ORGANISM: rabbit

<400> SEQUENCE: 28
gggtccatgg gtagacaacc agcagc                                        26

<210> SEQ ID NO 29
<211> LENGTH: 30
<212> TYPE: DNA
<213> ORGANISM: Escherichia coli

<400> SEQUENCE: 29
cagtcacgac gttgtaaaac gacggccagt                                    30

<210> SEQ ID NO 30
<211> LENGTH: 30
<212> TYPE: DNA
<213> ORGANISM: Escherichia coli

<400> SEQUENCE: 30
actggccgtc gttttacaac gtcgtgactg                                    30

<210> SEQ ID NO 31
<211> LENGTH: 75
<212> TYPE: DNA
<213> ORGANISM: Campylobacter jejuni

<400> SEQUENCE: 31
cttgaagcat agttcttgtt tttaaacttt gtccatcttg agccgcttga gttgagttgc    60
cttagtttta atagt                                                    75

<210> SEQ ID NO 32
<211> LENGTH: 30
<212> TYPE: DNA
```

-continued

<213> ORGANISM: Campylobacter jejuni

<400> SEQUENCE: 32
agttcttgtt tttaaacttt gtccatcttg                                      30

<210> SEQ ID NO 33
<211> LENGTH: 70
<212> TYPE: DNA
<213> ORGANISM: Campylobacter jejuni

<400> SEQUENCE: 33
actattaaaa ctaaggcaac tcaagcggct caagatggac aaagtttaaa aacaagaact     60
atgcttcaag                                                            70

<210> SEQ ID NO 34
<211> LENGTH: 30
<212> TYPE: DNA
<213> ORGANISM: Campylobacter jejuni

<400> SEQUENCE: 34
caagatggac aaagtttaaa aacaagaact                                      30

<210> SEQ ID NO 35
<211> LENGTH: 21
<212> TYPE: DNA
<213> ORGANISM: Cytomegalovirus

<400> SEQUENCE: 35
cactttgata ttcacccat g                                                21

<210> SEQ ID NO 36
<211> LENGTH: 21
<212> TYPE: DNA
<213> ORGANISM: Cytomegalovirus

<400> SEQUENCE: 36
cactttgata ttcacccgt g                                                21

<210> SEQ ID NO 37
<211> LENGTH: 65
<212> TYPE: DNA
<213> ORGANISM: Cytomegalovirus

<400> SEQUENCE: 37
cgtgtatgcc actttgatat tacacccatg aacgtgctca tcgacgtgaa cccgcacaac     60
gagct                                                                 65

<210> SEQ ID NO 38
<211> LENGTH: 65
<212> TYPE: DNA
<213> ORGANISM: Cytomegalovirus

<400> SEQUENCE: 38
cgttgtgcgg gttcacgtcg atgagcacgt tcatgggtgt aatatcaaag tggcatacac     60
gagct                                                                 65

<210> SEQ ID NO 39
<211> LENGTH: 65
<212> TYPE: DNA
<213> ORGANISM: Cytomegalovirus

<400> SEQUENCE: 39
cgtgtatgcc actttgatat tacacccgtg aacgtgctca tcgacgtgaa cccgcacaac    60
gagct    65

<210> SEQ ID NO 40
<211> LENGTH: 65
<212> TYPE: DNA
<213> ORGANISM: Cytomegalovirus

<400> SEQUENCE: 40
cgttgtgcgg gttcacgtcg atgagcacgt tcacgggtgt aatatcaaag tggcatacac    60
gagct    65

<210> SEQ ID NO 41
<211> LENGTH: 26
<212> TYPE: DNA
<213> ORGANISM: Cytomegalovirus

<400> SEQUENCE: 41
tcacacagga aacagctatg accatg    26

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: M13 FORWARD
      PROBE

<400> SEQUENCE: 42
gcaaggcgat taagttgggt aacg    24

<210> SEQ ID NO 43
<211> LENGTH: 40
<212> TYPE: DNA
<213> ORGANISM: Hepatitis C virus

<400> SEQUENCE: 43
ctgctagccg agtagtgttg ggtcgcgaaa ggccttgtgg    40

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: 35S
      PROMOTER PCR PRIMER

<400> SEQUENCE: 44
gatagtggga ttgtgcgtca    20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: 35S
      PROMOTER PCR PRIMER

<400> SEQUENCE: 45
gctcctacaa atgccatca    19

<210> SEQ ID NO 46
<211> LENGTH: 20

```
<212> TYPE: DNA
<213> ORGANISM: Artificial Sequence
<220> FEATURE:
<223> OTHER INFORMATION: Description of Artificial Sequence: NOS
      TERMINATOR

<400> SEQUENCE: 46
ttatcctagt ttgcgcgcta                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: NOS
      TERMINATOE PCR PRIMER

<400> SEQUENCE: 47
gaatcctgct gccggtcttg                                              20

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: 35S PROBE

<400> SEQUENCE: 48
gcaagtggat tgatg                                                   15

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: 35S PROBE

<400> SEQUENCE: 49
ccaaccacgt cttcaaa                                                 17

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: NOS PROBE

<400> SEQUENCE: 50
tttatgagat gggttt                                                  16

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: NOS probe

<400> SEQUENCE: 51
atgattagag tcccg                                                   15

<210> SEQ ID NO 52
<211> LENGTH: 16
<212> TYPE: DNA
<213> ORGANISM: Human immunodeficiency virus

<400> SEQUENCE: 52
```

-continued

```
ccatttagta ctgtct                                                16

<210> SEQ ID NO 53
<211> LENGTH: 16
<212> TYPE: DNA
<213> ORGANISM: Human immunodeficiency virus

<400> SEQUENCE: 53
ccatttagta ctgttt                                                16

<210> SEQ ID NO 54
<211> LENGTH: 16
<212> TYPE: DNA
<213> ORGANISM: Human immunodeficiency virus

<400> SEQUENCE: 54
ctagttttct ccattt                                                16

<210> SEQ ID NO 55
<211> LENGTH: 16
<212> TYPE: DNA
<213> ORGANISM: Human immunodeficiency virus

<400> SEQUENCE: 55
ctagttttct ccatct                                                16

<210> SEQ ID NO 56
<211> LENGTH: 16
<212> TYPE: DNA
<213> ORGANISM: Human immunodeficiency virus

<400> SEQUENCE: 56
ttctctgaaa tctact                                                16

<210> SEQ ID NO 57
<211> LENGTH: 16
<212> TYPE: DNA
<213> ORGANISM: Human immunodeficiency virus

<400> SEQUENCE: 57
ttctctgaaa tctatt                                                16

<210> SEQ ID NO 58
<211> LENGTH: 50
<212> TYPE: DNA
<213> ORGANISM: Human immunodeficiency virus

<400> SEQUENCE: 58
aaaaaagaca gtactaaatg gagaaaacta gtagatttca gagaacttaa           50

<210> SEQ ID NO 59
<211> LENGTH: 50
<212> TYPE: DNA
<213> ORGANISM: Human immunodeficiency virus

<400> SEQUENCE: 59
aaaaaaaaca gtactaaatg gagaaaacta gtagatttca gagaacttaa           50

<210> SEQ ID NO 60
<211> LENGTH: 50
<212> TYPE: DNA
<213> ORGANISM: Human immunodeficiency virus

<400> SEQUENCE: 60
```

```
aaaaaagaca gtactagatg gagaaaacta gtagatttca gagaacttaa          50

<210> SEQ ID NO 61
<211> LENGTH: 50
<212> TYPE: DNA
<213> ORGANISM: Human immunodeficiency virus

<400> SEQUENCE: 61
aaaaaagaca gtactaaatg gagaaaacta atagatttca gagaacttaa          50

<210> SEQ ID NO 62
<211> LENGTH: 11
<212> TYPE: DNA
<213> ORGANISM: Human immunodeficiency virus

<400> SEQUENCE: 62
agtgactggg g                                                    11

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence: probe which
      forms hairpin when allowed to self-anneal

<400> SEQUENCE: 63
atgaacgtac gtcggatgag cacgttcat                                 29

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: probe which
      forms hairpin when allowed to self-anneal

<400> SEQUENCE: 64
gtgaacgtac gtcggatgag cacgttcat                                 29

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: probe which
      forms hairpin when allowed to self-anneal

<400> SEQUENCE: 65
ataaacgtac gtcggatgag cacgttcat                                 29

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: probe which
      forms hairpin when allowed to self-anneal

<400> SEQUENCE: 66
ataaacgtac gtcggatgag cacg                                      24

<210> SEQ ID NO 67
<211> LENGTH: 62
<212> TYPE: DNA
```

```
<213> ORGANISM: Artificial Sequence
<220> FEATURE:
<223> OTHER INFORMATION: Description of Artificial Sequence: synthetic
      target sequence

<400> SEQUENCE: 67
cccggagaga cctccttaag gggccatatt atttcgtcga ttccagtgtt ggccaaacgg      60
at                                                                    62

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: synthetic
      target sequence

<400> SEQUENCE: 68
ggggccatat tatttcgccg tttggccaac actggaatcg a                         41

<210> SEQ ID NO 69
<211> LENGTH: 77
<212> TYPE: DNA
<213> ORGANISM: Artificial Sequence
<220> FEATURE:
<223> OTHER INFORMATION: Description of Artificial Sequence: synthetic
      target sequence

<400> SEQUENCE: 69
ggggccatat tatttcgccg tttggccaac actggaatcg acgaaataat atggccccctt     60 aaggaggtct ctccggg                                                    77

<210> SEQ ID NO 70
<211> LENGTH: 16
<212> TYPE: DNA
<213> ORGANISM: Artificial Sequence
<220> FEATURE:
<223> OTHER INFORMATION: Description of Artificial Sequence: synthetic
      target sequence

<400> SEQUENCE: 70
cccggagaga cctcct                                                     16

<210> SEQ ID NO 71
<211> LENGTH: 77
<212> TYPE: DNA
<213> ORGANISM: Artificial Sequence
<220> FEATURE:
<223> OTHER INFORMATION: Description of Artificial Sequence: synthetic
      target sequence

<400> SEQUENCE: 71
cccggagaga cctccttaag gggccatatt atttcgtcga ttccagtgtt ggccaaacgg      60
cgaaataata tggcccc                                                    77

<210> SEQ ID NO 72
<211> LENGTH: 65
<212> TYPE: DNA
<213> ORGANISM: Cytomegalovirus

<400> SEQUENCE: 72
cgtgtatgcc actttgatat tacacccatg aacgtgctca tcgacgtcaa cccgcacaac      60
gagct                                                                 65
```

```
<210> SEQ ID NO 73
<211> LENGTH: 65
<212> TYPE: DNA
<213> ORGANISM: Cytomegalovirus

<400> SEQUENCE: 73
cgttgtgcgg gttcacgtcg atgagcacgt tcatgggtgt aatatcaaag tggcatacac    60
gagct                                                                 65

<210> SEQ ID NO 74
<211> LENGTH: 65
<212> TYPE: DNA
<213> ORGANISM: Cytomegalovirus

<400> SEQUENCE: 74
cgtgtatgcc actttgatat tacacccgtg aacgtgctca tcgacgtcaa cccgcacaac    60
gagct                                                                 65

<210> SEQ ID NO 75
<211> LENGTH: 65
<212> TYPE: DNA
<213> ORGANISM: Cytomegalovirus

<400> SEQUENCE: 75
cgttgtgcgg gttcacgtcg atgagcacgt tcacgggtgt aatatcaaag tggcatacac    60
gagct                                                                 65

<210> SEQ ID NO 76
<211> LENGTH: 89
<212> TYPE: DNA
<213> ORGANISM: Artificial Sequence
<220> FEATURE:
<223> OTHER INFORMATION: Description of Artificial Sequence: probe to
      wild-type targets 10870 and 10994

<400> SEQUENCE: 76
gaactatatt gtctttctct gattctgact cgtcatgtct cagctttagt ttaatacgac    60
tcactatagg gctcagtgtg attccacct                                       89

<210> SEQ ID NO 77
<211> LENGTH: 53
<212> TYPE: DNA
<213> ORGANISM: Artificial Sequence
<220> FEATURE:
<223> OTHER INFORMATION: Description of Artificial Sequence: wild-type
      target

<400> SEQUENCE: 77
ttgcagagaa agacaatata gttcttggag aaggtggaat cacactgagt gga            53

<210> SEQ ID NO 78
<211> LENGTH: 53
<212> TYPE: DNA
<213> ORGANISM: Artificial Sequence
<220> FEATURE:
<223> OTHER INFORMATION: Description of Artificial Sequence: mutant
      target

<400> SEQUENCE: 78
ttgcagagaa agacaatata gttctttgag aaggtggaat cacactgagt gga            53

<210> SEQ ID NO 79
```

```
<211> LENGTH: 22
<212> TYPE: DNA
<213> ORGANISM: Artificial Sequence
<220> FEATURE:
<223> OTHER INFORMATION: Description of Artificial Sequence: probe which
      hydridizes to only to wild-type target

<400> SEQUENCE: 79
ctcagtgtga ttccacttca cc                                              22

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: probe which
      hydridizes only to mutant target

<400> SEQUENCE: 80
ctcagtgtga ttccaccttc aca                                             23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: probe which
      hydridizes to 10870 and 10994

<400> SEQUENCE: 81
ctaaagctga gacatgacga gtc                                             23

<210> SEQ ID NO 82
<211> LENGTH: 65
<212> TYPE: DNA
<213> ORGANISM: Cytomegalovirus

<400> SEQUENCE: 82
cgttgtgcgg gttcacgtcg atgagcacgt tcatgggtgt aatatcaaag tggcatacac     60
gagct                                                                 65

<210> SEQ ID NO 83
<211> LENGTH: 65
<212> TYPE: DNA
<213> ORGANISM: Cytomegalovirus

<400> SEQUENCE: 83
cgtgtatgcc actttgatat tacacccgtg aacgtgctca tcgacgtgaa cccgcacaac     60
gagct                                                                 65

<210> SEQ ID NO 84
<211> LENGTH: 65
<212> TYPE: DNA
<213> ORGANISM: Cytomegalovirus

<400> SEQUENCE: 84
cgttgtgcgg gttcacgtcg atgagcacgt tcacgggtgt aatatcaaag tggcatacac     60
gagct                                                                 65

<210> SEQ ID NO 85
<211> LENGTH: 24
<212> TYPE: DNA
<213> ORGANISM: kanamycin
```

-continued

```
<400> SEQUENCE: 85
gcaacgctac ctttgccatg tttc                                              24

<210> SEQ ID NO 86
<211> LENGTH: 12
<212> TYPE: DNA
<213> ORGANISM: Homo sapiens

<400> SEQUENCE: 86
ccagacgcct ca                                                           12

<210> SEQ ID NO 87
<211> LENGTH: 12
<212> TYPE: DNA
<213> ORGANISM: Homo sapiens

<400> SEQUENCE: 87
accttcacgc ca                                                           12

<210> SEQ ID NO 88
<211> LENGTH: 11
<212> TYPE: DNA
<213> ORGANISM: Unknown
<220> FEATURE:
<223> OTHER INFORMATION: Description of Unknown Organism:common probe to
      cytochrome B

<400> SEQUENCE: 88
tgccgagacg t                                                            11

<210> SEQ ID NO 89
<211> LENGTH: 12
<212> TYPE: DNA
<213> ORGANISM: chicken

<400> SEQUENCE: 89
gcagacacat cc                                                           12

<210> SEQ ID NO 90
<211> LENGTH: 12
<212> TYPE: DNA
<213> ORGANISM: chicken

<400> SEQUENCE: 90
ggaatctcca cg                                                           12

<210> SEQ ID NO 91
<211> LENGTH: 12
<212> TYPE: DNA
<213> ORGANISM: Bos sp.

<400> SEQUENCE: 91
acatacacgc aa                                                           12

<210> SEQ ID NO 92
<211> LENGTH: 12
<212> TYPE: DNA
<213> ORGANISM: Canis sp.

<400> SEQUENCE: 92
atatgcacgc aa                                                           12
```

EXOGENOUS NUCLEIC ACID DETECTION

CROSS-REFERENCE TO RELATED APPLICATIONS

This application is a continuation-in-part of U.S. Ser. No. 09/358,972, filed on Jul. 21, 1999, which is a continuation-in-part of U.S. Ser. No. 09/252,436, filed on Feb. 18, 1999, which is a continuation-in-part of U.S. Ser. No. 09/042,287, filed Mar. 13, 1998, all of which are incorporated herein by reference.

DESCRIPTION

1. Field of the Invention

The invention relates to nucleic acid detection. More specifically, the invention relates to the detection of a predetermined exogenous nucleic acid target sequence in a nucleic acid target/probe hybrid, and the various applications of such detection.

2. Background of the Invention

Methods to detect nucleic acids provide a foundation upon which the large and rapidly growing field of molecular biology is built. There is widespread application of such general methods to the detection of specific, exogenous nucleic acids. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity needed for a certain application, the ease of analysis, or the ability to automate the process.

The detection of nucleic acids, including specific exogenous nucleic acids, is often a portion of a process rather than an end in itself. There are many applications of the detection of nucleic acids in the art, and new applications are always being developed. The ability to detect and quantify exogenous nucleic acids is useful in detecting microorganisms and viruses and biological molecules (e.g. non-native promoter or terminator sequences or foreign genes) in a biological sample, and thus affects many fields, including human and veterinary medicine, food processing and environmental testing. Additionally, the detection and/or quantification of specific biomolecules from biological samples (e.g. tissue, sputum, urine, blood, semen, saliva) has applications in medicine and forensic science.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to a labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Enzymes having template-specific polymerase activity for which some 3'→5' depolymerization activity has been reported include E. coli DNA Polymerase (Deutscher and Kornberg, J. Biol. Chem., 244(11):3019–28 (1969)), T7 DNA Polymerase (Wong et al., Biochemistry 30:526–37 (1991); Tabor and Richardson, J. Biol. Chem. 265: 8322–28 (1990)), E. coli RNA polymerase (Rozovskaya et al., Biochem. J. 224:645–50 (1994)), AMV and RLV reverse transcriptases (Srivastava and Modak, J. Biol. Chem. 255: 2000–4 (1980)), and HIV reverse transcriptase (Zinnen et al., J. Biol. Chem. 269:24195–202 (1994)). A template-dependent polymerase for which 3' to 5' exonuclease activity has been reported on a mismatched end of a DNA hybrid is phage 29 DNA polymerase (de Vega, M. et al. EMBO J., 15:1182–1192, 1996)

There is a need for highly sensitive, diagnostic applications that are capable of determining the number of virus molecules present in a body ("viral load"). For example, the presence of viral particles in the circulation system or in specific tissues is a means of monitoring the severity of viral infection. Several methods are currently used in the art for determining viral load. U.S. Pat. No. 5,667,964 discloses a method for the determination of the number of HIV-1 infected patient cells using reactive oxygen-intermediate generators. U.S. Pat. No. 5,389,512 discloses a method for determining the relative amount of a viral nucleic acid segment in a sample using PCR.

G. Garinis et al., J. Clin. Lab. Anal. 13:122–5 (1999) compare the determination of viral load results using an enzyme-linked immunosorbent assay (ELISA), a recombinant immunoblot assay (RIBA), and a reverse transcriptase polymerase chain reaction method (RT-PCR) in the detection of hepatitis C virus (HCV) infection in haemodialysis patients. The quantitative hepatitis HCV RT-PCR assay had a detection level of about 2,000 viral copies/mL serum. Holguin et al., Eur. J. Clin. Microbiol. Infect. Dis. 18:256–9 (1999) compare plasma HIV-1 RNA levels using several commercially available assays, namely the second-generation HIV-1 branched DNA assay, the Nuclisens assay, the Amplicor® Monitor reverse transcriptase polymerase chain reaction assay, and the Ultradirect Monitor. Differing values were noted in comparing results among these various assays. Boriskin et al., Arch. Dis. Child. 80:132–6 (1999) used a nested polymerase chain reaction to measure HIV-1 proviral DNA and CMV genomic DNA in peripheral blood leukocytes of children infected with HIV-1. There remains a need for a reliable means to detect and quantify viral load.

There is a demand for methods to determine viral load when the quantities of viral particles are very low.

There is a need for alternative methods for detection of nucleic acid hybrids. There is a demand for highly sensitive methods that are useful for determining the presence or absence of specific nucleic acid sequences that are non-native or "exogenous" to an organism's nucleic acid. For example, there is a need to determine the presence of non-native nucleic acid present in a cell, both when the non-native nucleic acid is incorporated into the native nucleic acid and when it is not incorporated. For example, there is a need for methods to determine viral load that are able to reliably detect as few as 10 copies of a virus present in a body, tissue, fluid, or other biological sample. There is great demand for methods to determine the presence of a mutant virus, e.g. a drug-resistant mutant, in a biological sample containing a viral population. There is great demand for methods to determine the presence or absence of non-native sequences unique to a particular species in a sample, for example the identification of bacterial contamination present in a primarily non-bacterial biological sample. There is also great demand for methods that are more highly sensitive than the known methods, methods that are highly reproducible and automatable.

It would be beneficial if another method were available for detecting the presence of a sought-after, predetermined exogenous target nucleotide sequence. It would also be beneficial if such a method were operable using a sample size of the microgram to picogram scale. It would further be beneficial if such a detection method were capable of providing multiple analyses in a single assay (multiplex assays). The disclosure that follows provides one such method.

BRIEF SUMMARY OF THE INVENTION

A method of this invention is used to determine the presence or absence of a predetermined exogenous nucleic acid target sequence in a nucleic acid sample. Such a method utilizes an enzyme that depolymerizes the 3'-terminus of an oligonucleotide probe hybridized to a nucleic acid target sequence to release one or more identifier nucleotides whose presence can then be determined.

One embodiment of the invention contemplates a method for determining the presence or absence of a predetermined, exogenous nucleic acid target sequence in a nucleic acid sample. More than one such predetermined target sequence can also be present in the sample being assayed, and the presence or absence of more than one predetermined nucleic acid target sequence can be determined. The embodiment comprises the following steps.

A treated sample is provided that may contain a predetermined nucleic acid target sequence hybridized with a nucleic acid probe that includes an identifier nucleotide in the 3'-terminal region. The treated sample is admixed with a depolymerizing amount of an enzyme whose activity is to release one or more nucleotides from the 3'-terminus of a hybridized nucleic acid probe to form a treated reaction mixture. The type of enzyme used for nucleotide release will be further identified and described herein. The treated reaction mixture is maintained under depolymerizing conditions for a time period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output is obtained by various techniques as discussed herein.

It is contemplated that an analytical output of a method of the invention can be obtained in a variety of ways. The analytical output can be ascertained by luminescence spectroscopy. In some preferred embodiments, analysis for released 3'-terminal region indicator nucleotides comprises the detection of ATP, either by a luciferase detection system (luminescence spectroscopy) or an NADH detection system (absorbance or fluorescence spectroscopy). In particularly preferred embodiments, ATP molecules are formed by a phosphate transferring step, for example using an enzyme such as NDPK in the presence of ADP, with the phosphate group originating from the nucleotide triphosphates produced by the depolymerizing step. In other embodiments, the ATP produced is amplified to form a plurality of ATP molecules. In the ATP detection embodiments, the enzyme nucleoside diphosphate kinase (NDPK) is typically present in the depolymerization reaction and functions to convert released nucleotides and added ADP into ATP, and thus reactions where the two enzymes are present together, are denoted as a "one pot" method.

In an alternative embodiment, the analytical output is obtained by fluorescence spectroscopy. Fluorescence can be incorporated or added to a probe in a number of ways known in the art. For example, it is contemplated that an identifier nucleotide includes a fluorescent label. An identifier nucleotide can be fluorescently labeled prior to, or after, release of the identifier nucleotide. It is also contemplated that other than a released identifier nucleotide contains a fluorescent tag. In such an embodiment, the release of nucleotides in a process of the invention is ascertained by a determination of a difference in the length of the polynucleotide probe, for example by capillary electrophoresis imaged by a fluorescent tag at the 5' terminus of the probe or in a region other than the 3' terminal region.

In an alternative embodiment the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescent-labeled identifier nucleotide, the analytical output can also be obtained by mass spectrometry. It is also contemplated that the analysis of released nucleotide be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotide or the remainder of the probe can be analyzed to ascertain the release of the identifier nucleotide in a process of the invention. In another aspect of such a process a label may be incorporated in the analyzed nucleic acid.

In a contemplated embodiment, a sample to be assayed for the presence or absence of an exogenous nucleic acid target sequence is admixed with one or more nucleic acid probes under hybridizing conditions to form a hybridization composition. The 3'-terminal region of the nucleic acid probe hybridizes with partial or total complementarity to the exogenous nucleic acid target sequence when that sequence is present in the sample. The 3'-terminal region of the nucleic acid probe includes an identifier nucleotide. The hybridization composition is maintained under hybridizing conditions for a time period sufficient to form a treated sample that may contain said predetermined nucleic acid target sequence hybridized with a nucleic acid probe. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output may be obtained by various techniques as discussed above.

One method of the invention contemplates interrogating the presence or absence of a specific base in an exogenous nucleic acid target sequence in a sample to be assayed, and comprises the following steps.

A hybridization composition is formed by admixing a sample to be assayed with one or more nucleic acid probes under hybridizing conditions. The sample to be assayed may contain an exogenous nucleic acid target sequence to be interrogated. The nucleic acid target comprises at least one base whose presence or absence is to be identified. The hybridization composition includes at least one nucleic acid probe that is substantially complementary to the nucleic acid target sequence and comprises at least one predetermined nucleotide at an interrogation position, and an identifier nucleotide in the 3' terminal region.

A treated sample is formed by maintaining the hybridization composition under hybridizing conditions for a time period sufficient for base pairing to occur when a probe nucleotide at an interrogation position is aligned with a base to be identified in the target sequence. A treated reaction mixture is formed by admixing the treated sample with an enzyme whose activity is to release one or more identifier nucleotides from the 3' terminus of a hybridized nucleic acid probe to depolymerize the hybrid. The treated reaction mixture is maintained under depolymerizing conditions for a time period sufficient to permit the enzyme to depolymerize the hybridized nucleic acid and release an identifier nucleotide.

An analytical output is obtained by analyzing for the presence or absence of released identifier nucleotides. The analytical output indicates the presence or absence of the specific base or bases to be identified. The analytical output is obtained by various techniques as discussed herein. Preferably, an identifier nucleotide is at the interrogation position.

In one aspect of a method of the invention, the nucleic acid target sequence is selected from the group consisting of deoxyribonucleic acid and ribonucleic acid.

In another aspect of the invention, the sample containing a plurality of target nucleic acid sequences is admixed with a plurality of the nucleic acid probes. Several analytical outputs can be obtained from such multiplexed assays.

In a first embodiment, the analytical output obtained when at least one nucleic acid probe hybridizes with partial complementarity to one target nucleic acid sequence is greater than the analytical output when all of the nucleic acid probes hybridize with total complementarity to their respective nucleic acid target sequences. In a second embodiment, the analytical output obtained when at least one nucleic acid probe hybridizes with partial complementarity to one target nucleic acid sequence is less than the analytical output when all of the nucleic acid probes hybridize with total complementarity to their respective nucleic acid target sequences. In a third embodiment, the analytical output obtained when at least one nucleic acid probe hybridizes with total complementarity to one nucleic acid target sequence is greater than the analytical output when all of the nucleic acid probes hybridize with partial complementarity to their respective nucleic acid target sequences. In a fourth embodiment, the analytical output obtained when at least one nucleic acid probe hybridizes with total complementarity to one target nucleic acid sequence is less than the analytical output when all of the nucleic acid probes hybridize with partial complementarity to their respective nucleic acid target sequences. The depolymerizing enzymes are as described herein.

Yet another embodiment of the invention contemplates a method for determining the presence or absence of a first exogenous nucleic acid target in a nucleic acid sample that may contain that target or may contain a substantially identical second target. For example, the second target may have a base substitution, deletion or addition relative to the first nucleic acid target. This embodiment comprises the following steps.

A sample to be assayed is admixed with one or more nucleic acid probes under hybridizing conditions to form a hybridization composition. The first and second nucleic acid targets each comprise a region of sequence identity except for at least a single nucleotide at a predetermined position that differs between the targets. The nucleic acid probe is substantially complementary to the nucleic acid target region of sequence identity and comprises at least one nucleotide at an interrogation position. An interrogation position of the probe is aligned with the predetermined position of a target when a target and probe are hybridized. The probe also includes an identifier nucleotide in the 3'-terminal region.

The hybridization composition is maintained under hybridizing conditions for a time period sufficient to form a treated sample wherein the nucleotide at the interrogation position of the probe is aligned with the nucleotide at the predetermined position in the region of identity of the target.

A treated reaction mixture is formed by admixing the treated sample with a depolymerizing amount of an enzyme whose activity is to release one or more nucleotides from the 3'-terminus of a hybridized nucleic acid probe. The reaction mixture is maintained under depolymerization conditions for a time period sufficient to permit the enzyme to depolymerize the hybridized nucleic acid and release the identifier nucleotide.

An analytical output is obtained by analyzing for the presence or absence of released identifier nucleotides. The analytical output indicates the presence or absence of the nucleotide at the predetermined region, and; thereby, the presence or absence of a first nucleic acid target.

One aspect of the above method is comprised of a first probe and a second probe. The first probe comprises a nucleotide at an interrogation position that is complementary to a first nucleic acid target at a predetermined position. The second probe comprises a nucleotide at an interrogation position that is complementary to a second nucleic acid target at a predetermined position.

In another aspect of a process of the invention, the depolymerizing enzyme, whose activity is to release nucleotides, is a template-dependent polymerase, whose activity is to depolymerize hybridized nucleic acid, whose 3'-terminal nucleotide is matched, in the 3'→5' direction in the presence of pyrophosphate ions to release one or more nucleotides. Thus, the enzyme's activity is to depolymerize hybridized nucleic acid to release nucleotides under depolymerizing conditions. Preferably, this enzyme depolymerizes hybridized nucleic acids whose bases in the 3'-terminal region of the probe are matched with total complementarity to the corresponding bases of the nucleic acid target.

In an alternative aspect of the process of the invention, the depolymerizing enzyme, whose activity is to release nucleotides, exhibits a 3'→5' exonuclease activity in which hybridized nucleic acids having one or more mismatched bases at the 3'-terminus of the hybridized probe are depolymerized. Thus, the enzyme's activity is to depolymerize hybridized nucleic acid to release nucleotides under depolymerizing conditions. In this embodiment, the hybrid can be separated from the free probe prior to enzyme treatment. In some embodiments, an excess of target may be used so that the concentration of free probe in the enzyme reaction is extremely low.

In still another alternative aspect of a process of the invention, the depolymerizing enzyme exhibits a 3' to 5' exonuclease activity on a double-stranded DNA substrate having one or more matched bases at the 3' terminus of the hybrid. The enzyme's activity is to depolymerize hybridized nucleic acid to release nucleotides containing a 5' phosphate under depolymerizing conditions.

In particularly preferred embodiments, ATP molecules are formed by a phosphate transferring step, (e.g. using the enzyme NDPK in the presence of ADP), from the deoxynucleoside triphosphates (dNTPs) producerd by the depolymerizing step. In some embodiments, the ATP can be amplified to form a plurality of ATP molecules. Thermostable nucleoside diphosphate kinases are particularly preferred when an NDPK enzyme is used.

In one aspect of the invention, the nucleic acid sample to be assayed is obtained from a biological sample that is a solid or liquid.

In one aspect of the method, the predetermined nucleic acid target sequence is present in the sample for the purpose of gene therapy.

In one aspect of the method, the predetermined nucleic acid target sequence is a microbial or viral nucleic acid.

In some preferred embodiments of the invention, the predetermined nucleic acid target sequence is a viral nucleic acid. Viral load, the amount of virus present, can be determined from the magnitude of the analytical output from a predetermined amount of biological sample such as animal fluid or tissue.

In some preferred embodiments, the presence or absence of a mutation in the viral genome can be determined.

In another aspect of the method, the nucleic acid sample is obtained from a food source. In one process of the method, the food source is a plant or is derived from plant material, and the predetermined nucleic acid target sequence is a sequence not native to that plant. In one aspect of the method, the nucleic acid sequence not native to the subject plant is a transcription control sequence. In one preferred embodiment of the invention, the transcription control sequence is the 35S promoter or the NOS terminator, or both.

A still further embodiment of the invention contemplates determining the presence or absence of an exogenous nucleic acid target sequence in a nucleic acid sample with a probe that is hybridized to the target and then modified to be able to form a hairpin structure. This embodiment comprises the following steps.

A treated sample is provided that contains a nucleic acid sample that may include an exogenous nucleic acid target sequence having an interrogation position hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50 nucleotides, and preferably about zero to about 20 nucleotides in length, and comprising a sequence that does not hybridize with either the first or second section, is located between the first and second sections of the probe.

The probe of the treated sample is extended in a template-dependent manner, as by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs. The extended probe/target hybrid is denatured to separate the strands. The extended probe strand is permitted to form a hairpin structure.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the exogenous nucleic acid target sequence.

A still further embodiment of the invention, termed REAPER™, also utilizes hairpin structures. This method contemplates determining the presence or absence of an exogenous nucleic acid target sequence, or a specific base within the target sequence, in a nucleic acid sample, and comprises the following steps. A treated sample is provided that contains a nucleic acid sample that may include an exogenous nucleic acid target sequence hybridized with a first nucleic acid probe strand.

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. An optional third section of the probe, located between the first and second sections of the probe, is zero to about 50 nucleotides, preferably up to about 20 nucleotides, in length and comprises a sequence that does not hybridize to either the first or second section.

The first hybrid in the treated sample is extended at the 3'-end of the first probe, thereby extending the first probe past the interrogation position and forming an extended first hybrid whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000 nucleotides, preferably about 10 to about 200 nucleotides, most preferably about 10 to about 30 nucleotides, in length and is complementary to the extended first probe at a position beginning about 5 to about 2000, preferably about 5 to about 200, nucleotides downstream of the interrogation position in extended first probe, is annealed to the extended first probe, thereby forming the second hybrid. The second hybrid is extended at the 3'-end of the second probe until that extension reaches the 5'-end of the extended first probe, thereby forming a second extended hybrid whose 3'-region includes an identifier nucleotide. In preferred embodiments the extending polymerase for both extensions does not add a nucleotide to the 3' end that does not have a corresponding complementary nucleotide in the template.

An aqueous composition of the extended second hybrid is denatured to separate the two nucleic acid strands. The aqueous composition so formed is cooled to form a "hairpin structure" from the separated extended second probe when the target sequence is present in the original nucleic acid sample.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the exogenous nucleic acid target sequence.

The present invention has many benefits and advantages, several of which are listed below.

One benefit of the invention is that, in some embodiments, nucleic acid hybrids can be detected with very high levels of sensitivity without the need for radiochemicals or electrophoresis.

An advantage of the invention is that the presence or absence of one or more exogenous target nucleic acid(s) can be detected reliably, reproducibly, and with great sensitivity.

A further benefit of the invention is that quantitative information can be obtained about the amount of exogenous target nucleic acid sequence in a sample and a large variety of sample types can be used.

A further advantage of the invention is that very slight differences in exogenous nucleic acid sequence are detectable, including single nucleotide polymorphisms (SNPs).

Yet another benefit of the invention is that the presence or absence of a number of exogenous target nucleic acid sequences can be determined in the same assay.

Yet another advantage of the invention is that the presence or absence of an exogenous target nucleic acid can be determined with a small number of reagents and manipulations.

Another benefit of the invention is that the processes lend themselves to automation.

Still another benefit of the invention is its flexibility of use in many different types of applications and assays including, but not limited to, determination of viral load, determination of viral type, species identification, sample contamination, and analysis of forensic samples.

Still further benefits and advantages of the invention will become apparent to the skilled worker from the disclosure that follows.

BRIEF DESCRIPTION OF THE FIGURES

In the drawings forming a portion of this disclosure,

FIG. 1 illustrates the annealing of the 10865 oligonucleotide (SEQ ID NO:76) to 10870 wild type (SEQ ID NO:77) and 10994 mutant (SEQ ID NO:78) oligonucleotides utilized in rolling circle amplification as FIG. 1A and FIG. 1B, respectively. Also shown are the annealing (hybridization) of oligonucleotide 10866 (SEQ ID NO:81) to oligonucleotide 10865, as well as the hybridization of oligonucleotide probe 10869 (SEQ ID NO:79) to oligonucleotide 10870 and of oligonucleotide probe 10989 (SEQ ID NO:80) to oligonucleotide 10994 as representations of the binding of those probes to the respective amplified sequences. Arcuate lines in oligonucleotide 10865 are used to help illustrate the shape that oligonucleotide 10865 can assume when hybridized with either of oligonucleotides 10870 or 10994.

FIG. 2. illustrates the Reaper™ assay as described in Example 21. FIG. 2A illustrates the first hybrid formed by the annealing of nucleic acid target SEQ ID NO: 67 (286) to first probe SEQ ID NO: 68 (287). An arrow points to an interrogation position in 286.

FIG. 2B illustrates the first extended hybrid formed by the annealing of 286 to the extended 287. Extended 287 is first extended probe SEQ ID NO: 69 (288).

FIG. 2C illustrates the second hybrid formed by annealing of 288 from the denatured nucleic acid molecule shown in FIG. 2B to the second probe denoted SEQ ID NO: 70 (289). An arrow points to the interrogation position in 288.

FIG. 2D illustrates the extended second hybrid formed by the annealing of 288 and the extended 289 strand denoted SEQ ID NO: 71 (290).

FIG. 2E illustrates the 290 strand denatured from FIG. 2D and forming a hairpin structure. An arrow points to the interrogation position at the 3'-terminus of the hybrid.

DEFINITIONS

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "DNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position.

A "single nucleotide polymorphism" or SNP, as used herein, is a variation from the most frequently occurring base at a particular nucleic acid position.

As used herein, the term "exogenous" with reference to a nucleic acid sequence is a nucleic acid that is not native in a sample. For example, a gene that was inserted into a cell is exogenous, or a virus that is present in a host cell is exogenous. It may be exogenous whether or not it is incorporated into the DNA of the host cell.

DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'-ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides may contain a modified linkage such as a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. PCR, $2^{nd}$ Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency.

When used in reference to a single-stranded nucleic acid sequence, the term "substantially homologous", as used herein, refers to a probe that can hybridize to (i.e., is the complement of) the single-stranded nucleic acid template sequence under conditions of low stringency.

The term "interrogation position", as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide", as used herein, refers to a nucleotide whose presence is to be detected in a process of the invention to identify whether a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are "converted" to ATP with an enzyme such as NDPK, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide can be labeled, or the fluorescence level modified, prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

The term "sample" is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection", as used herein, refers to quantitatively or qualitatively identifying a nucleotide or nucleic acid within a sample.

The term "depolymerization", as used herein, refers to the removal of a nucleotide from the 3' end of a nucleic acid.

The term "allele", as used herein, refers to an alternative form of a gene and the term "locus", as used herein, refers to a particular place on a nucleic acid molecule.

DETAILED DESCRIPTION OF THE INVENTION

A contemplated method is utilized to assay for the presence or absence of nucleic acid that is exogenous to the source of the sample. For example, a contemplated method can be used to assay for the presence of viruses such as hepatitis C virus (HCV), cytomegalovirus (CMV), human immunodeficiency virus (HIV), as well as to determine the viral load in an organism with a disease, such as a human or a plant. A contemplated method can also be used to identify the presence of an exogenous nucleic acid sequence in a plant such as maize, soy or rice. A contemplated method can also be used to assay for the presence of microorganisms such as Listeria monocytogenes, Campylobacter spp., Salmonella spp., Shigella spp. or Escherichia coli (including E. coli E0157) in foodstuffs such as meats, dairy products, and fruit juices.

The determination of an appropriate exogenous nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing PCR primers can be used to assist in the design of probes for use in the invention.

A method of this invention is used to determine the presence or absence of at least one predetermined (known) exogenous nucleic acid target sequence in a nucleic acid sample. A nucleic acid target is "predetermined" in that its sequence must be known to design a probe that hybridizes with that target. However, it should be noted that a nucleic acid target sequence, as used with respect to a process of this invention, may merely act as a reporter to signal the presence of a different nucleic acid whose presence is desired to be determined. That other nucleic acid of interest does not have to have a predetermined sequence. Furthermore, a process of the invention is useful in determining the identity of base within a target where only enough of the sequence is known to design a probe that hybridizes to that exogenous target with partial complementarity at the 3'-terminal region of the probe.

Such a method utilizes an enzyme that can depolymerize the 3'-terminus of an oligonucleotide probe hybridized to the nucleic acid target sequence to release one or more identifier nucleotides, under depolymerizing conditions, whose presence or absence can then be determined as an analytical output that indicates the presence or absence of the target sequence.

A nucleic acid target sequence is predetermined (or known) in that a nucleic acid probe is provided to be partially or totally complementary to that nucleic acid target sequence. A nucleic acid target sequence is a portion of nucleic acid sample with which the probe hybridizes if that target sequence is present in the sample.

A first step of the method is admixing a sample to be assayed with one or more nucleic acid probes. The admixing of the first step is typically carried out under low stringency hybridizing conditions to form a hybridization composition. In such a hybridization composition, the 3'-terminal region of the nucleic acid probe(s) (i) hybridizes with partial or total complementarity to an exogenous nucleic acid target sequence that may be present in the sample; and (ii) includes an identifier nucleotide in the 3'-terminal region.

Preferably, the nucleic acid probe is designed to not hybridize with itself to form a hairpin structure in such a way as to interfere with hybridization of the 3'-terminal region of the probe to the target nucleic acid. Parameters guiding probe design are well known in the art.

The hybridization composition is maintained under hybridizing conditions for a time period sufficient to form a treated sample that may contain at least one predetermined nucleic acid target hybridized with a nucleic acid probe.

In the event that the sample to be assayed does not contain a target sequence to which the probe hybridizes, no hybridization takes place. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

The treated sample is admixed with a depolymerizing amount of an enzyme whose activity is to release one or more identifier nucleotides from the 3'-terminal region of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzyme reaction conditions is discussed in detail hereinafter.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of at least the one nucleic acid target sequence.

Hybridization conditions can be empirically ascertained for a control sample for various time periods, pH values, temperatures, nucleic acid probe/target combinations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient, but moderate stringency conditions (e.g. temperatures of 40–60° C.) also permit hybridization and provide acceptable results. This is true for all processes of the invention.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

In an embodiment that uses a 3'→5' exonuclease activity of a polymerase, such as Klenow or T4 DNA polymerase (but not limited to those two enzymes), to depolymerize a nucleic acid probe, an identifier nucleotide is released when the 3'-terminal residue of the nucleic acid probe is mismatched and therefore there is only partial complementarity of the 3'-terminus of the nucleic acid probe to its nucleic acid target sequence. In this embodiment, to minimize background, the hybrid is typically purified from the unannealed nucleic acid prior to the depolymerization enzyme reaction, which may release an identifier nucleotide. A signal confirms the presence of a nucleic acid target sequence that is not totally complementary to the nucleic acid probe.

In an embodiment that uses a 3'→5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide.

It is thus seen that hybridization and depolymerization can lead to the release of an identifier nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires for depolymerization activity.

The magnitude of a contemplated analytical output under defined conditions is dependent upon the amount of released identifier nucleotides. Where an identifier nucleotide is released, an analytical output can be provided that has a value greater than background. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level.

Contemplated methods and kits of the invention are useful for many applications as discussed above. For example, it is desirable to detect exogenous nucleic acid sequences when one would like to detect the presence or amount of viral contamination (or viral load) in a sample, often a biological or medical sample, but also in a food sample. The art provides many sequences that are useful for a wide variety of viral targets, and as more sequences are discovered, they are likewise useful in a process of the present invention. Thus, also contemplated are plant viruses, such as the tobacco mosaic virus. Exemplary viral probes follow.

Cytomegalovirus sequence probes.

5' CGTTGTGCGGGTTCACGTCGATGAG-
CACGTTCATGGGTGTAATATCAAAGTG-
GCATACACGAGCT 3'                    SEQ ID NO:82

5' CACTTTGATATTACACCCATG 3'         SEQ ID NO:35

JH67 5' TCACACAGGAAACAGCTATGACCAT-
G 3'                                  SEQ ID NO:41

Hepatitis C virus probe.

HCV1:5' CTGCTAGCCGAGTAGTGTTGGGTCGC-
GAAAGGCCTTGTGG 3'                    SEQ ID NO:43

Human Immunodeficiency virus probes.

11808 5' CCATTTAGTACTGTCT 3'          SEQ ID NO:52

11810 5' CTAGTTTTCTCCATTT 3'          SEQ ID NO:54

11812 5' TTCTCTGAAATCTACT 3'          SEQ ID NO:56

11814 5' AAAAAAGACAGTACTAAATGGAGAAAAC-
TAGTAGATTTCAGAGAACTTAA 3'            SEQ ID NO:58

Below are provided sequences of probes to various mutated viruses. Such probes are useful for distinguishing the presence of a particular mutated pathogen among other pathogens present.

Probes to a mutated cytomegalovirus sequences.

CV2 5' CACTTTGATATTACACCCGTG 3'      SEQ ID NO:36

5' CGTGTATGCCACTTTGATATTACAC-
CCGTGAACGTGCTCATCGACGTGAAC-
CCGCACAACGAGCT 3'                    SEQ ID NO:83

5' CGTTGTGCGGGTTCACGTCGATGAG-
CACGTTCACGGGTGTAATATCAAAGTG-
GCATACACGAGCT3'                      SEQ ID NO:84 gancyclovir-resistant cytomegalovirus probes:

CV11 5' CGCTTCTACCACGAATGCTCGCAGAC-
CATGCTGCACGAATACGTCAGAAA-
GAACGTGGAGCGTCTGTTGGAGCT 3'         SEQ ID NO:1

CV12 5' CCAACAGACGCTCCACGTTCTTTCT-
GACGTATTCGTGCAGCATGGTCTGCGAG-
CATTCGTGGTAGAAGCGAGCT 3'             SEQ ID NO:2

CV13 5' CGCTTCTACCACGAATGCTCGCAGAT-
CATGCTGCACGAATACGTCAGAAA-
GAACGTGGAGCGTCTGTTGGAGCT 3'         SEQ ID NO:3

CV14 5' CCAACAGACGCTCCACGTTCTTTCT-
GACGTATTCGTGCAGCATGATCTGCGAG-
CATTCGTGGTAGAAGCGAGCT 3'             SEQ ID NO:4

Probes to drug-resistant HIV.

11815 5' AAAAAAAACAGTACTAAATGGAGAAAAC-
TAGTAGATTTCAGAGAACTTAA 3'            SEQ ID NO:59

11816 AAAAAAGACAGTACTAGATGGAGAAAAC-
TAGTAGATTTCAGAGAACTTAA 3'            SEQ ID NO:60

11817 5' AAAAAAGACAGTACTAAATGGAGAAAAC-
TAATAGATTTCAGAGAACTTAA 3'            SEQ ID NO:61

11813 5' TTCTCTGAAATCTATT 3'          SEQ ID NO:57

11811 5' CTAGTTTTCTCCATCT 3'          SEQ ID NO:55

11809 5' CCATTTAGTACTGTTT 3'          SEQ ID NO:53

The presence of other exogenous nucleic acids, such as those stemming from contaminating bacteria are useful in a process of the invention. Examples of bacterial probes follow.

Probes for Listeria iap.

LM1 5' GAAGTAAAACAAACTACACAAGCAACTA-
CACCTGCGCCTAAAGTAGCAGAAAC-
GAAAGAAACTCCAGTAG 3'                 SEQ ID NO:9

LM2 5' CTACTGGAGTTTCTTTCGTTTCTGC-
TACTTTAGGCGCAGGTGTAGTTGCTTGT-
GTAGTTTGTTTTACTTC 3'                 SEQ ID NO:10

LM3 5' GCAACTACACCTGCGCCTAAAGTAG-
CAGAA 3'                              SEQ ID NO:11

LM4 5' TTCTGCTACTTTAGGCGCAGGTGTAG-
TTCG 3'                               SEQ ID NO:12

Probes for Listeria hyl.

LM5 5' CATCGACGGCAACCTCGGAGACTTAC-
GAGATATTTTGAAAAAAGGCGCTACTTT-
TAATCGAGAAACACCA 3'                  SEQ ID NO:13

LM6 5' TGGTGTTTCTCGATTAAAAGTAGCGC-
CTTTTTTCAAAATATCTCGTAAGTCTC-
CGAGGTTGCCGTCGATG 3'                 SEQ ID NO:14

LM7 5' CTCGGAGACTTACGAGATATTTTGAA-
AAAA 3'  SEQ ID NO:15

LM8 5' TTTTTTCAAAATATCTCGTAAGTCTCC-
GAG 3'  SEQ ID NO:16

Probes for Salmonella.

ST3 5' TGTGTAATGAAAGAAATCACCGTCACT-
GAA 3'  SEQ ID NO:19

ST4 5' TTCAGTGACGGTGATTTCTTTCATTAC-
ACA 3'  SEQ ID NO:20

Probes to *Campylobacter jejuni*.

11453 5' CTTGAAGCATAGTTCTTGTTTT-
TAAACTTTGTCCATCTTGAGCCGCT-
TGAGTTGCCTTAGTTTTAATAGT 3'  SEQ ID NO:31

11454 5'ACTATTAAAACTAAGGCAACTCAAGCG-
GCTCAAGATGGACAAAGTTTAAAAACAA-
GAACTATGCTTCAAG 3'  SEQ ID NO:33

11451 5'AGTTCTTGTTTTTAAACTTTGTCCATC-
TTG 3'  SEQ ID NO:32

11450 5' CAAGATGGACAAAGTTTAAAAACAA-
GAACT 3'  SEQ ID NO:34

It is often desirable to detect the presence of exogenous genes, typically incorporated merely as markers for inserted genes. Classic molecular biology techniques include the incorporation of antibiotic resistance to select for clones having the desired inserted exogenous nucleic acid sequence. The antibiotic resistance gene is also an exogenous sequence. The sequences of exogenous "marker" genes are well-known in the art and are easily available to a worker of ordinary skill. Exemplary fragments of such sequences useful as probes in methods and kits of the present invention follow.

Probes for genes conferring kanamycin resistance to bacteria.

| 5'GCAACGCTACCTTTGCCATGTTTC 3' | SEQ ID NO:21 |
| 5'GCAACGCTACCTTTGCCATGTTTG 3' | SEQ ID NO:22 |
| 5'GCAACGCTACCTTTGCCATGTTTA 3' | SEQ ID NO:23 |
| 5'GCAACGCTACCTTTGCCATGTTTT 3' | SEQ ID NO:24 |
| 5'GCAACGCTACCTTTGCCATGTTTC 3' | SEQ ID NO:85 |

Probes to the β-galactosidase gene, commonly used as a biological marker for exogenous genes in the field of biochemistry.

5' CAGTCACGACGTTGTAAAACGACGGCCAG 3' SEQ ID NO:29

5'ACTGGCCGTCGTTTTACAACGTCGTGACTG 3' SEQ ID NO:30

Other exogenous sequences, though not necessarily used as markers, are useful in methods and kits of the present invention. This is discussed further in the examples below, particularly with respect to genetically modified organisms. Some exemplary common exogenous sequences that are often introduced along during genetic engineering of an organism follow.

Probes for the plant 35S promoter commonly used in biotechnology when inserting exogenous plant genes.

11211 5' GCAAGTGGATTGATG 3'  SEQ ID NO:48

11210 5' CCAACCACGTCTTCAAA 3'  SEQ ID NO:49

Probes for the plant NOS terminators commonly used in biotechnology when inserting exogenous genes.

11212 5' TTTATGAGATGGGTTT 3'  SEQ ID NO:50

11213 5' ATGATTAGAGTCCCG 3'  SEQ ID NO:51

In one embodiment of the invention, viral load, the amount of virus present, is determined from the magnitude of the analytical output from a predetermined amount of biological sample such as a animal fluid or tissue. Processes of the invention are quantitative and very sensitive. The sensitivity is enhanced further through use of a process of the invention including a step to enrich the sample in the predetermined exogenous nucleic acid target sequence, by conversion of a signal from the predetermined exogenous nucleic acid target sequence to an amplified predetermined reporter sequence or by amplification of the signal from the released identifier nucleotide. In the viral load example below, the target sequence is enriched in the sample through RT-PCR.

In one aspect of the method, the predetermined nucleic acid target sequence is present in the sample for the purpose of gene therapy. An exemplary gene therapy embodiment would be in the provision of an exogenous gene to an animal, preferably a person or commonly raised animal such as a cow, pig, sheep, dog or chicken, to make up for a missing gene, such as is the case with phenyl ketonuria or persons lacking adenine deaminase.

A worker of ordinary skill in the art recognizes that processes and kits of the invention are useful with any predetermined sequence that is specifically sought for assay. Such a worker need only construct a nucleic acid probe that is complementary to the predetermined sequence. Thus the present invention is useful for determining the success of genetic engineering into a plant, typically a crop, by searching for the introduced gene. Similarly, the success of plant breeding is monitored using a process of the invention when the gene sought to be introduced into the cross-bred generation is a nucleic acid target.

A worker of ordinary skill further recognizes that it is possible to construct any desired probes for the specific methods using the invention disclosed in the parent application, U.S. Ser. No. 09/358,972, filed on Jul. 21, 1999.

In one embodiment, the identity of a specific base located at an interrogation position within a nucleic acid target sequence is determined. This is useful for determination of the presence or absence of certain mutations within a gene. Examples of such mutated genes were listed above, such as the resistant HIV, or the gancyclovir resistant CMV.

Depolymerization

Depolymerization reactions and enzymes useful in such reactions are discussed below. Nucleic acid polymerases generally catalyze the elongation of nucleic acid chains. The reaction is driven by the cleavage of a pyrophosphate released as each nucleotide is added. Each nucleoside-5'-triphosphate has three phosphate groups linked to carbon five of the ribose or deoxyribose sugar. The addition of a nucleotide to a growing nucleic acid results in formation of an internucleoside phosphodiester bond. This bond is characterized in having a 3' linkage to carbon 3 of ribose or deoxyribose and a 5' linkage to carbon 5 of ribose or deoxyribose. Each nucleotide is added through formation of a new 3' to 5' linkage, so the nucleic acid strand grows in a 5' to 3' direction.

Depolymerization in its strictest sense means the reverse of polymerization so that in the present context, an internucleotide phosphodiester bond is broken between the two 3'-terminal bases in the presence of pyrophosphate and a polymerase enzyme to form a nucleic acid that is one nucleotide shorter and a nucleoside triphosphate. A some-what more encompassing definition is contemplated here. In accordance with that definition, the 3'-terminal nucleotide is removed from a nucleic acid in a reaction catalyzed by an enzyme, but the nucleotide formed can be a monophosphate and pyrophosphate is not always required.

The former reactions (i.e. reverse of polymerization) are referred to herein as pyrophosphorolysis reactions whereas the latter, more encompassing definition, reactions are referred to as exonuclease reactions. It is to be understood that the depolymerization reaction of interest in the invention is that depolymerization occurring in the 3'-terminal region of the nucleic acid probe. This depolymerization reaction releases identifier nucleotides under appropriate depolymerizing conditions, as discussed herein.

Depolymerization reactions and enzymes useful in such reactions are discussed in parental U.S. patent application Ser. No. 09/358,972, filed on Jul. 21, 1999, which disclosure is incorporated herein by reference.

A. Pyrophosphorolysis

In some embodiments of the present invention, a method comprises depolymerizing the nucleic acid (NA) at a 3'-terminal nucleotide by enzymatically cleaving the terminal internucleoside phosphodiester bond in the presence of pyrophosphate, or an analogue thereof, to form an XTP (e.g. NTPs or dNTPs) as illustrated by the following reaction on double-stranded DNA having a 5' overhang:

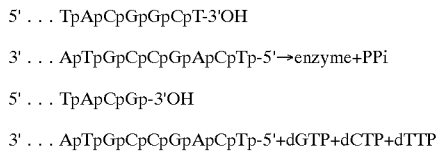

Template-dependent nucleic acid polymerases capable of pyrophosphorolysis include, but are not limited to, DNA polymerase α, DNA polymerase β, T4 DNA polymerase, Taq polymerase, Tne polymerase, Tne triple mutant polymerase, Tth polymerase, Tvu polymerase, Ath polymerase, Bst polymerase, *E. coli* DNA polymerase I, Klenow fragment, Klenow exo minus (exo–), AMV reverse transcriptase, RNA polymerase and MMLV reverse transcriptase, and poly(A) polymerase.

Most preferably, Klenow exo minus (Klenow exo–) or Tne triple mutant polymerase is utilized for DNA pyrophosphorolysis reactions because of their efficient utilization of 5' overhanging DNA ends.

In a preferred embodiment in the case of the reverse of polymerase activity (pyrophosphorolysis), a preferred substrate is a DNA probe hybridized to an exogenous nucleic acid target sequence with total complementarity at its 3'-terminus, including an identifier residue in the 3'-terminal region. In an example of this preferred embodiment, when the nucleic acid probe is hybridized to an exogenous nucleic acid target sequence such that there is one base mismatch at the 3'-terminal nucleotide of the nucleic acid probe, the nucleic acid probe is inefficiently depolymerized through the reverse polymerization reaction. Thus, such a substrate is not an ideal substrate for depolymerization.

The non-ideality of the substrate for depolymerization via a reverse of the polymerization reaction is recognized with a single base mismatch as far in as about 10 residues from the 3'-terminus of the nucleic acid probe. With a single base mismatch 12 residues from the 3'-terminus of the probe, the depolymerization reaction can occur to approximately the same extent as when there is no mismatch and the nucleic acid probe is totally complementary to the nucleic acid target sequence.

It is thus contemplated that the reactivity of the depolymerization reaction is a continuum that is related to the efficiency of the substrate. A partially complementary hybrid is a less efficient depolymerization substrate than a totally complementary hybrid for the reverse of a polymerization reaction. It is contemplated that this differential reactivity be used to enhance the discrimination between matches and mismatches at certain positions (e.g. an interrogation position). When a substrate hybrid is totally complementary, it will give a fairly high analytical output. A mismatch can be intentionally introduced to destabilize the substrate hybrid. Such a destabilization can increase the difference in analytical output between bases substituted at an interrogation position that is different from the destabilizing base position.

Several chemical compounds are known in the art to be substitutable for pyrophosphate in pyrophosphorolysis reactions. Rozovskaya, et al., *Biochem. J.*, 224:645–650 (1984).

Preferred reaction mixtures and times (depolymerization conditions) for depolymerization by pyrophosphorolysis, including suitable buffers for each nucleic acid polymerase analyzed, are described in greater detail in the Examples. Typically, under these conditions, sufficient NTP or dNTP is released to accurately detect or assay extremely low amounts of nucleic acids (e.g., about 5–1000 picograms). ATP can be produced by conversion from XTP by an enzyme such as NDPK (in the presence of ADP) prior to analysis or the ATP can be further amplified prior to analysis.

The high efficiency of the pyrophosphorolysis reaction was unexpected, and appears to be associated with extremely low levels of DNA substrate, in contrast to previous DNA pyrophosphorolysis studies conducted using much greater amounts of DNA.

The pyrophosphorolysis activity of different nucleic acid polymerases also varies. For example, T4 polymerase and Tne DNA polymerase possess very high pyrophosphorolysis activity as measured by a luciferase assay for ATP produced by pyrophosphorolysis. Pyrophosphorolysis using T4 polymerase resulted in about a 10 fold increase in light production as compared to MMLV-RT and a 4-fold increase in light production as compared to Taq polymerase.

The type of DNA end resulting from restriction enzyme digestion also affects the pyrophosphorolysis activity of different nucleic acid polymerases. For example, Klenow exo–, MMLV-RT and Taq polymerase catalyze pyrophosphorolysis of DNA fragments with 5'-overhangs and with blunt-ends, but have little or no pyrophosphorolysis activity with 3'-overhangs. In contrast, T4 DNA polymerase catalyzes both 3'- and 5'-end overhang and blunt-end mediated pyrophosphorolysis. Thus, T4 DNA polymerase is a preferred enzyme for pyrophosphorolysis of a hybrid with a 3'-overhang. When other nucleic acid polymerases are utilized for pyrophosphorolysis of restriction enzyme treated DNA, it is contemplated that care is taken to match the end specificity of the polymerase with the type of end created by the restriction endonuclease. Such care is well within the skill of those in the art.

Further, it is contemplated that the type of polymerase used in the pyrophosphorolysis reaction is matched to the correct nucleic acid substrate in order to produce the best results. In general, DNA polymerases and reverse transcriptases are preferred for depolymerizing DNA, whereas RNA polymerases are preferred for depolymerizing RNA. Reverse transcriptases or DNA polymerases with reverse transcriptase activity are preferred for depolymerizing RNA-DNA hybrids.

In the grandparent application, it was surprisingly demonstrated that poly(A) polymerase can catalyze pyrophosphorolysis, even though no such reaction had been previously reported. Indeed, poly(A) polymerase has been widely reported to not catalyze pyrophosphorolysis. (See e.g., Sippel, *Eur. J. Biochem.*, 37:31–40 (1973) and Sano and Feix, *Eur. J. Biochem.*, 71:577–83 (1976)). However there are many differences between the conditions used in the grandparent application disclosure and those reported in the references. In these preferred embodiments of the invention disclosed in the grandparent application, the manganese chloride present in the previously reported buffers is omitted, the concentration of sodium chloride is decreased, and the pH value is lowered from about 8.0 to about 7.5. Furthermore, the poly(A) polymerase pyrophosphorolysis reaction buffer contains about 50 mM Tris-Cl pH 7.5, 10 mM $MgCl_2$, 50 mM NaCl, and 2 mM $NaPP_i$ (sodium pyrophosphate).

It is important to note that the depolymerization reaction is the reverse of the polymerization reaction. Therefore, as increasing amounts of free nucleoside triphosphates are produced by depolymerization, a state of equilibrium can theoretically be attained in which polymerization and depolymerization reactions are balanced. Alternatively, where small amounts of nucleic acid are detected, the reaction can go essentially to completion without reaching equilibrium, (i.e., the nucleic acid target is depolymerized into its constituent subunit nucleotides by greater than 50%). This factor is important in quantitative assays because the total amount of nucleotides released is proportional to the amount of signal generated in the detection assay.

When used for qualitative detection of nucleic acid, as long as a threshold level of nucleotides is produced, it is not necessary that the reaction reach equilibrium or go essentially to completion. In preferred embodiments, the mixture of nucleoside triphosphate molecules produced by depolymerization is preferably converted to ATP as described below. For either quantitative or qualitative detection, a detectable threshold ATP concentration of approximately $1 \times 10^{-12}$ molar in 100 µl of sample is preferably provided for detection of light in a typical luciferase assay.

In some preferred embodiments, oligonucleotide probes are typically utilized at about 100 ng to about 1 µg per 20 µL depolymerization reaction. That amount provides a probe to target weight ratio of about 200:1 to about 1,000:1.

In a preferred embodiment of the present invention, nucleic acid polymerase and pyrophosphate ($PP_i$) or an analogue thereof, are added to a hybridized sample containing from less than about 100 µg of target nucleic acid, to less than about 10 pg of nucleic acid. Typical target nucleic acids are present at about 1 to about 5 ng in the sample to be assayed, with a target nucleic acid length of about 30 to about 1000 bp being preferred.

When using enzymes that utilize 5' overhang substrates, it is preferred that the 3' end of the target nucleic acid extends beyond the 5' end of the nucleic acid probe. In this way, the only 5' overhang substrate is that where the 5' end of the target nucleic acid overhangs the 3' terminal region of the nucleic acid probe. An alternative method of limiting depolymerization to the nucleic acid probe is chemical modification of the ends of other nucleic acids in the sample, such as, for example, making a phosphorothioate linkage at the 3'-terminus of the target nucleic acid.

A depolymerizing enzyme is preferably present in an amount sufficient to depolymerize a hybridized target:probe. That amount can vary with the enzyme used, the depolymerization temperature, the buffer, and the like, as are well-known in the art. For a typical reaction carried out in a 20 µL volume, about 0.25 to about 1 unit (U) of an enzyme such as Klenow exo– is used. About 1 to about 5 U of the thermostable enzymes are used for depolymerization at elevated temperatures.

Luciferase, which is part of the preferred ATP detection system, is inhibited by $PP_i$. In preferred embodiments, care is taken to avoid transferring a highly inhibiting amount of PPi to the ATP detection reaction. Preferably, the amount of $PP_i$ carried over to the ATP detection reaction results in a concentration of $PP_i$ in the luciferase detection reaction of less than about 100 µM, although less than about 10 µM is desirable. Therefore, the amount of $PP_i$ utilized in the pyrophosphorolysis reaction is determined by the size of the aliquot that is taken for use in the luciferase detection system. It is contemplated that the aliquot size can vary depending upon the test system used, but the amount of $PP_i$ transferred or carried over to the luciferase detection reaction corresponds to the $PP_i$ concentration parameters described above, so that the concentration of $PP_i$ is at least below about 100 µM, and preferably below about 10 µM.

In one preferred embodiment of the invention, the enzyme whose activity is to depolymerize is a template-dependent polymerase. The depolymerization reaction is a reverse of the polymerization reaction. In a contemplated embodiment, the polymerization reaction is reversed in the presence of pyrophosphate in a reaction referred to as pyrophosphorolysis.

In some preferred embodiments, the reaction conditions are preferably adjusted to further favor depolymerization of a nucleic acid probe that is hybridized with its target nucleic acid sequence by providing a higher concentration of nucleic acid probe than its target nucleic acid sequence.

One strategy to favor the depolymerization of a probe-:target hybrid is that the probe be in molar excess over the nucleic acid target in the hybridization step after denaturing of duplex target nucleic acid.

Another strategy to favor the depolymerization of a probe:target hybrid is to isolate only the strand of nucleic acid target to which the probe is complementary. There are several techniques that can be used to achieve this end.

In one such technique, phosphorothioate linkages are utilized at the 5'-terminus of a target nucleic acid amplifying primer sequence, e.g., at the 1 to about 10 5'-most residues. Upon PCR amplification of the target, the phosphorothioate linkages of the primer become incorporated into the amplified target nucleic acid as part of one of a pair of complementary strands. Treatment of the double-stranded resulting molecule with T7 polymerase exonuclease 6 removes the non-phosphorothioate-containing strand.

In another technique, strand isolation can be accomplished by amplifying the target nucleic acid using PCR primers incorporated into the extended nucleic acid strand (with which a nucleic acid probe useful herein is designed to hybridize) that are not labeled, whereas primers for the complementary strand are labeled, such as with biotin. Then, the amplified nucleic acid is denatured and added to streptavidin linked to a solid support. A useful material is Streptavidin MagneSphere® paramagnetic particles (Promega, Z548A), where a magnet can be used to separate the desired target nucleic acid strand from its biotinylated complementary strand. Further discussion pertaining to pyrophosphorolysis is found in the parent cases cited above and incorporated herein by reference.

B. Exonuclease Digestion

In other embodiments of the present invention, a method comprises depolymerizing the nucleic acid at a 3'-terminal nucleotide by enzymatically cleaving the terminal internucleoside phosphodiester bond to form an XMP as illustrated by the following reaction on double-stranded DNA having a 5'-overhang:

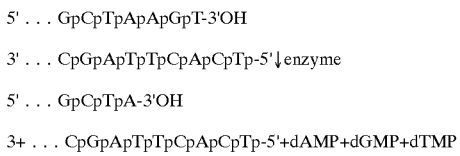

For example, such a hydrolysis reaction can be catalyzed by Klenow or Exonuclease III.

In some embodiments (e.g., quantitative assays for nucleic acids), the depolymerizing step is repeated essentially to completion or equilibrium to obtain at least two nucleotide molecules from a strand of minimally three nucleotides in order to increase detection sensitivity. In alternative embodiments, (e.g., qualitative detection of DNA), the depolymerizing step need not be repeated if there are sufficient nucleic acid molecules present to generate a signal.

In another embodiment of the present invention, terminally mismatched hybridized nucleic acid probes are first depolymerized into NMP or dNMP by exonuclease digestion according to the following reaction:

$$NA_n + H_2O \rightarrow NA_{n-1} + XMP \qquad \text{Reaction 1}$$

wherein $NA_n$ is a nucleic acid, XMP is either a dNMP or NMP, and n is the number of nucleotides in the nucleic acid.

This depolymerization reaction is shown more specifically below in the following reaction on double-stranded DNA having a 5'-overhang and mismatched bases at the 3'-terminus:

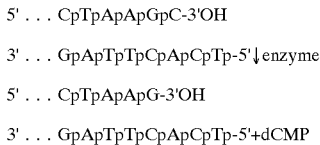

For example, such a depolymerization reaction can be catalyzed by bacteriophage T4 polymerase in the absence of NTPs. In preferred embodiments, the released nucleotides, XMPs, are produced by nuclease digestion.

Nuclease digestion can be accomplished by a variety of nucleases that release a nucleotide with a 5' phosphate, including S1 nuclease, nuclease Bal 31, mung bean nuclease, exonuclease III and ribonuclease H. Nuclease digestion conditions and buffers are known in the art. Nucleases and buffers for their use are available from commercial sources.

In the biosynthesis of purine and pyrimidine mononucleotides, phosphoribosyl-1-pyrophosphate (PRPP) is the obligatory ribose-5'-phosphate donor. PRPP itself is formed in a reaction catalyzed by PRPP synthetase through the transfer of pyrophosphate from ATP to ribose-5'-phosphate. This reaction is known to be reversible as described in Sabina et al., Science, 223:1193–95 (1984).

In some embodiments of the present invention, the NMP or DNMP produced by nuclease digestion is preferably converted directly to NTP or dNTP by the enzyme PRPP synthetase in the following reaction:

$$XMP + PRPP \rightarrow XTP + \text{ribose-5'-}PO_4 \qquad \text{Reaction 2}$$

wherein XMP is either AMP or dAMP, and XTP is either ATP or dATP. Preferably, this reaction produces a threshold ATP concentration of approximately $1 \times 10^{-12}$ M in 100 µl of sample.

In this reaction, the pyrophosphate group of PRPP is enzymatically transferred to XMP molecules, forming XTP molecules. Examples of suitable reaction conditions and buffers are set forth elsewhere herein.

Utilization of the PRPP reaction in the nucleic acid detection system of the present invention has advantages over previously reported methods. For example, only one step is necessary to convert an AMP or dAMP to ATP or dATP, thereby simplifying the detection system. In addition, contamination of the detection reaction with exogenous ATP, ADP, or AMP is less likely using methods of the present invention, as compared to previously reported methods.

In an embodiment wherein the depolymerizing enzyme exhibits 3'→5' exonuclease activity, the substrate is a double-stranded or single-stranded nucleic acid having a 3'-hydroxyl terminus. Enzymes having 3'→5' exonuclease activity that are useful in a process of the invention include E. coli DNA polymerase I, Klenow fragment and bacteriophage T4 DNA polymerase. E. coli DNA polymerase I holoenzyme is not preferred in a process of the invention because it is preferable to avoid the 5'→3' exonuclease activity that degrades probe:target hybrids regardless of the degree of hybridization at the 3'-terminus. Bacteriophage λ exonuclease has only 5'→3' exonuclease activity, so it is not a contemplated enzyme. Similarly, Taq DNA polymerase has a very low level of 3'→5' exonuclease activity. Exonuclease III (Exo III) has 3' exonuclease activity on blunt-ended substrates or those having 5'-overhangs or nicks with 3'-hydroxyl groups, and is thus useful in a process of the invention for depolymerizing hybrids with matched 3' terminal nucleotides. However, Exo III is not limited to hybrids having only partially complementary 3'-termini, it requires a double stranded end, i.e. a matched terminal nucleotide.

In an embodiment of the invention where the enzyme's activity is a 3'→5' exonuclease activity, the hybridized nucleic acid probe is depolymerized from its 3'-terminal nucleotide. In a preferred embodiment in the case of a 3'→5' exonuclease activity of a polymerase, the preferred substrate is a nucleic acid probe hybridized to an exogenous nucleic acid target sequence with partial complementarity at its 3'-terminal region, most preferably with a mismatch at its 3'-terminal residue that is an identifier nucleotide.

A contemplated method is particularly useful in a multiplex assay environment in which a plurality of probes is utilized to determine whether one or more of a plurality of predetermined exogenous nucleic acid sequences is present or absent in a sample. A particularly useful area for such multiplex assays is in screening assays where the usual analytical output indicates that the sought-after exogenous gene is absent.

In one illustrative embodiment, a nucleic acid sample is screened for the presence of a plurality of predetermined exogenous genes, e.g. viruses in a biological sample. In this embodiment, the viruses usually are not present and the analytical output is, for example, at about background levels except where a virus with its exogenous nucleic acid is present.

In another embodiment, a plurality of samples is examined for the presence or absence of microbe-specific genes. Here, again, where a population of healthy individuals, animals, or presumably sterile food is sampled, the absence of the sought-after exogenous genes provides an analytical output that is about background levels, and only in the rare instance of microbial contamination does a greater than the background output appear.

In a multiplexed embodiment of the above process, the sample is admixed with a plurality of different exogenous nucleic acid probes, in some embodiments after amplification of the multiple nucleic acid targets as needed. In this embodiment of the invention, the analytical output for a certain result with one of the probes is distinguishable from the analytical output from the opposite result with all of the probes.

In preferred embodiments, the ATP produced via NDPK conversion of released nucleotides in the presence of ADP is detected by a luciferase detection system or an NADH detection system. In still another embodiment of the present invention, the pyrophosphate transferring step and the phosphate transferring step are performed in a single pot reaction. In other preferred embodiments, if increased sensitivity is required, the ATP molecules can be amplified.

Analytical Output

The analytical output is obtained by detection of the released identifier products, either the released nucleotides or the remainder of the probe. Exemplary detection systems include the light emitting luciferase detection system, the NADH light adsorption detection system (NADH detection system), fluorescence emissions and mass spectrometry. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods. Mass spectrometry of oligonucleotides is also becoming more common.

A. Luminescence Spectroscopy

Luciferase detection systems are particularly useful for detecting ATP. In the presence of ATP and oxygen, luciferase catalyzes the oxidation of luciferin, producing light that can then be quantified using a luminometer. Additional products of the reaction are AMP, pyrophosphate and oxyluciferin.

In particularly preferred embodiments, ATP detection buffer referred to as L/L reagent (Promega, FF2021) is utilized. Preferably, about 5 to 10 ng of luciferase are used in the reaction. Although it is not intended that the present invention be limited to a specific concentration of luciferase, greater amounts of luciferase have a tendency to increase non-specific background.

It is contemplated that in some embodiments, the dNTPs or NTPs produced by pyrophosphorolysis or nuclease digestion are converted to XTP, which can then be used directly as substrate for luciferase, permitting detection of the nucleic acid. However, the preferred substrate for luciferase is ATP, as demonstrated by Moyer and Henderson, *Anal. Biochem.*, 131:187–89 (1983). When DNA is the initial substrate, NDPK is conveniently utilized to catalyze the conversion of dNTPs to ATP by the following general reaction:

dNTP*+ADP→dNDP+ATP*                Reaction 3 wherein dNTP is a mixture of deoxyribonucleoside triphosphates and dNDP is the corresponding deoxyribonucleoside diphosphate. In Reaction 3, the terminal 5'-triphosphate (P*) of the DNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPK, see Parks and Agarwal, in *The Enzymes*, Volume 8, P. Boyer Ed. (1973).

The conversion of NTPs or dNTPs to ATP by NDPK is preferably accomplished by adding NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice.

The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A, D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

A reaction containing NDPK contains about 0.01 to 0.50 $\mu$M ADP, preferably about 0.05 $\mu$M ADP. Various useful buffers and other reaction components are set forth elsewhere. NDPK is itself present in an amount sufficient to catalyze the desired conversion of ADP to ATP. In a typical assay starting from a 20 $\mu$L depolymerization reaction, about 0.1 U of NDPK are used.

Where larger volumes of reactants are used, with the target and probe concentrations being approximately proportionately larger, the amount of NDPK or the other enzymes discussed herein can be used in a similar larger proportion relative to the amount discussed for the 20 $\mu$L reaction. Indeed, a 20 $\mu$L reaction has been successfully scaled down about two fold and scaled upwardly by a factor of about 20.

B. Mass Spectrometric Analysis

In one method of the invention, the presence of released nucleotides is analyzed via mass spectrometry. In an embodiment of a method using mass spectrometry, the treated reaction mixture is ionized in a manner such that all components of the treated reaction mixture in the molecular weight range of the released identifier nucleotides are measured. Very small differences in molecular weight can be detected using mass spectrographic methods (different isotopes of the same atom are detectable), so any variation from a natural nucleic acid, including a single atom substitution (e.g. a fluorine in place of a hydrogen atom or a replacement of a hydrogen by a deuterium atom) in the identifier nucleotide gives rise to a detectable difference. Nucleic acid analogs used in methods of the invention should not interfere with either the hybridization of the nucleic acid probe or depolymerization of the hybridized probe.

Additionally, mass spectrometry can discriminate between individual nucleotides or nucleosides. For example, if the 3'-identifier nucleotide used in the instant invention was a G nucleotide, mass spectrometry can be used to detect the release of that G nucleotide in a method of the present invention. Similarly, mass spectrometry can detect the release of an A, T or C nucleotide, based on the differences in atomic weight of these compounds. Thus, in a multiplexing embodiment of the present invention, mass spectrometry can be used to resolve the presence of one or more of these 3'-identifier nucleotides.

In a particularly useful aspect of this embodiment, a mass spectral technique referred to as DIOS (desorption/ionization on silicon) was recently reported by Wei et al., *Nature,* 399:243(1999) that can accurately perform one or multiple assays on picogram or attagram amounts using commercially available mass spectrographs adapted with a specialized porous silicon sample well. The older, well known, MALDI mass spectrographic assay techniques can also be utilized.

In an embodiment of a multiplex method using mass spectrometry, multiple different identifier nucleotides can be used in the various nucleic acid probes. Using such a technique the presence of the different identifier nucleotides is direct evidence of the presence of the nucleic acid target sequences.

C. Fluorescence Spectroscopic Analysis

In some contemplated embodiments, the identifier nucleotide emits fluorescence. For example, in one embodiment when the nucleotide has a fluorescent label, the analytical output is obtained by fluorescence spectroscopy. In an alternative embodiment when the nucleotide has a fluorescent label, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN™ Life Science Products (Boston, Mass.), who offer dideoxy-, deoxy-, and ribonucleotide analogs a labeled with fluorescein, coumarin, tetramethylrhodamine, naphthofluorescein, pyrene, Texas Red™, and Lissamine™. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels. Such different labels would be particularly useful in a multiplex embodiment of the invention. Different fluorescent labels would be used in different probes, so that the detection of a particular fluorescently-labeled nucleotide analog as a released identifier nucleotide could be used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a released identifier nucleotide could be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include Nature, 193:167 (1962), Methods *Enzymol.* 26:28 (1972), *Anal. Biochem.,* 57:227 (1974), *Proc. Natl. Acad. Sci., U.S.,* 72:459 (1975).

It is contemplated that for many embodiments of the invention, it is useful to separate released fluorescent identifier nucleotides from those bound to an oligonucleotide, such as a probe. Thus, the separation techniques well known in the art and discussed above are useful with such an embodiment, including HPLC fitted with a fluorescence detector. The enhanced sensitivity of fluorescence relative to other spectroscopic techniques can be used to increase the sensitivity of a detection or quantification process of the invention.

In an alternative embodiment wherein the analytical output is determined using fluorescence spectroscopy, an NADH detection system is used. In the NADH detection system, a combination of two enzymes, phosphoglycerate kinase and glyceraldehyde phosphate dehydrogenase, is used to catalyze the formation of NAD from NADH in the presence of ATP. Thus, this is in effect an ATP detection system, and much of the discussion herein relating to the detection of ATP with respect to the luciferase/luciferin system applies here. Because NADH is fluorescent whereas NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB 2,055,200, all of which are herein incorporated by reference.

D. Absorbance Spectroscopic Analysis

An absorbance spectrographic analysis step is contemplated to provide an analytical output, thereby provide for the determination of the presence or absence released identifier nucleotide, and indicate the presence or absence of said nucleic acid target sequence. This embodiment contemplates the chromatographic separation of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo–, releasing the labeled nucleotides and other nucleotides from the 3'-termini of probes hybridized to target sequences when the 3' terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80T$_M$ or ODS-120T TSK-GEL by Toso-Haas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 65 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., *J. Chromatography*, 317:283–300 (1984), and Perrone & Brown, *J. Chromatography*, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions (as determined by continually monitoring the absorbance of the column effluent) can be determined by other standard analytical methods, such as nuclear magnetic resonance or atomic analysis (H,C,N).

In this illustrative example using depolymerization with Klenow exo–, the presence of a released identifier nucleotide from a particular probe indicates the presence of the target sequence that hybridize with that probe.

In an alternative embodiment, the released nucleotides from a depolymerization reaction mixture are separated on a gas chromatograph fitted with an absorbance detector to monitor column effluent.

Probe-mediated Specific Nucleic Acid Detection

In yet another preferred embodiment, the probe-mediated specific nucleic acid detection method of the present invention can be used to simply identify or detect a nucleic acid of interest. For this method, a nucleic acid probe (e.g., DNA or RNA) is utilized which is substantially complementary to the target nucleic acid, which can be RNA or DNA. In a particularly preferred embodiment, the nucleic acid probe is entirely complementary to the exogenous target nucleic acid. The nucleic acid probe comprises single-stranded nucleic acid (e.g., DNA or RNA). The probe can be of varying lengths, preferably from about 10 to about 1000 bases, most preferably about 10 to 100 bases. Detection is carried out as described above. The nucleic acid probe-nucleic acid target/probe hybrid (complex) is exposed to conditions permitting depolymerization of the probe, which results in the production of XTPs. Detection of the nucleic acid of interest is characterized by a difference in the signal generated by the XTPs produced. Preferably, the XTPs are converted to ATP as described above and the ATP detected by a luciferase or NADH detection system.

Preferred conditions for depolymerization (depolymerization conditions) are described elsewhere herein. The nucleotides are then detected. In some preferred embodiments, the nucleotides are converted to ATP equivalents as described hereinabove and in the Examples. In preferred embodiments, the ATP is detected by luciferase (luminescence spectroscopy) or NADH (fluorescence spectroscopy) detection systems.

As mentioned before, the determination of an appropriate nucleic acid target sequence useful for designing nucleic acid probes for use in a method of the invention is within the skill of the art.

Depolymerization reactions can also be used to interrogate the identity of a specific base in a nucleic acid. For example, the identity of single base point mutations, deletions, or insertions in a nucleic acid can be determined as follows.

In one embodiment, a nucleic acid probe is synthesized that is substantially complementary to a target nucleic acid containing or suspected of containing a point mutation. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid.

The nucleic acid probe comprises single-stranded nucleic acid (e.g., DNA or RNA). The probe can be of varying lengths, preferably from about 10 to 100 bases, most preferably about 10 to 30 bases. In particularly preferred embodiments, the probe is complementary to the target at all bases between an interrogation position and 3' end of the nucleic acid probe.

In preferred embodiments, the probe is designed to have a predetermined nucleotide at an interrogation position. When the complementary probe base pairs or hybridizes to the target nucleic acid, the base at an interrogation position aligns with the base in the nucleic acid target whose identity is to be determined under conditions such that base pairing can occur. It is contemplated that an interrogation position can be varied within the probe. For example, in some preferred embodiments, an interrogation position is preferably within 10 bases of the 3' end of the nucleic acid probe. In still other preferred embodiments, an interrogation position is within 6 bases of the 3' end of the nucleic acid probe. In particularly preferred embodiments, an interrogation position is at the next to last or last base at the 3' end of the nucleic acid probe.

In some preferred embodiments, four different probes of equal length are synthesized, each having a different nucleotide at an interrogation position. Accordingly, it is contemplated that in some embodiments, a set of DNA probes includes a first probe with a deoxyadenosine residue at an interrogation position, a second probe with a deoxythymidine residue at an interrogation position, a third probe with a deoxyguanosine residue at an interrogation position, and a fourth probe with a deoxycytosine residue at an interrogation position. Likewise, it is also contemplated that a set of RNA probes includes a first probe with an adenosine residue at an interrogation position, a second probe with a uridine residue at an interrogation position, a third probe with a guanosine residue at an interrogation position, and a fourth probe with a cytosine residue at an interrogation position.

In the next step of some embodiments, the probe or probes are hybridized to the exogenous target nucleic acid in separate reactions so that a probe nucleic acid-target nucleic acid complex is formed. It is contemplated that hybridization conditions can vary depending on the length and base composition of the probe.

In the probe-target nucleic acid complex, the nucleotide at an interrogation position is aligned with the specific base to be identified in the nucleic acid. In embodiments in which a set of probes is utilized, a different reaction is performed with each probe. In a multiplex embodiment, the set of probes can be used simultaneously. Because the probes differ at an interrogation position only one of the probes is complementary to the specific base in the target nucleic acid that is aligned with an interrogation position.

In the next step of some embodiments, the nucleic acid probe-target nucleic acid complexes are individually reacted under conditions permitting depolymerization of the hybridized probe. The preferred reaction conditions for depolymerization are described before and in the following Examples. The nucleotides are then detected.

In preferred embodiments, the reaction mixture also contains reagents necessary to catalyze the conversion of XTP to ATP equivalents as described in reaction 3 and in the following Examples. In some preferred embodiments, the nucleotides and/or ATP produced by the depolymerization reaction are then detected by either a luciferase or NADH detection system. Complementarity of the base at an interrogation position of the nucleic acid probe to the corresponding base in the nucleic acid target is characterized by detection of a signal generated from ATP following depolymerization.

In particularly preferred embodiments, the identity of the specific base is determined by comparing the amount of ATP produced in each reaction. Depolymerization of the probe proceeds from its 3' end. When the base at an interrogation position is not complementary to the specific base in the nucleic acid, very little or no ATP is produced, and thus no signal results. In alternative embodiments, this method can be practiced with from one to four probes. It is contemplated that utilizing multiple probes, (e.g., each with a different base at an interrogation position), may prove unnecessary if a positive signal is produced (e.g., with the first probe tested).

Assays Using Hairpin Structures

Although it is preferred that the probes be constructed to be free of hairpin structures, assays in which hairpin structures are constructed are also useful. An embodiment of the invention, such as demonstrated in Example 20, contemplates use of a hairpin structure for determining the presence or absence of a nucleic acid target sequence in a nucleic acid sample with a probe that is hybridized to the exogenous target and then modified to be able to form a hairpin structure. This embodiment comprises the following steps.

A treated sample is provided that contains a nucleic acid sample that may include an exogenous nucleic acid target sequence having an interrogation position. The target sequence, if present in the nucleic acid sample is hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This same sequence, therefore, exists in both the target and the probe in the same 5' to 3' orientation. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, preferably from zero to about 20, nucleotides in length and comprising a sequence that does not hybridize with either the first or second section, is located between the first and second sections of the probe.

The probe of the treated sample is extended in a template-dependent manner, by admixture with dNTPs and a template-dependent polymerase, at least through the interrogation position, thereby forming an extended probe/target hybrid that contains a sequence complementary to that at the interrogation position. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs; i.e., purified at least to the degree needed to use the extended probe strand to determine the presence or absence of the interrogation region in the sample or the identity of the base at the interrogation position. The extended probe/target hybrid is denatured to separate the strands. The extended probe strand is permitted to form a hairpin structure.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the exogenous nucleic acid target sequence. That analytical output can be determined as discussed elsewhere herein.

A still further embodiment of the invention, such as that termed REAPER™ and demonstrated in Example 21 and FIG. 2, also contemplates use of hairpin structures in determining the presence or absence of an exogenous nucleic acid target sequence, or a specific base within the target sequence, in a nucleic acid sample, and comprises the following steps. A treated sample is provided that contains a nucleic acid sample that may include an exogenous nucleic acid target sequence hybridized with a first nucleic acid probe strand (FIG. 2A).

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. That is, the second sequence is a repeat of the region in the exogenous target sequence from the interrogation position downstream to the position where the 3'-terminal nucleotide of the first probe aligns with the target. An optional third section of the probe, located between the first and second sections of the probe, is zero to about 50, preferably to about 20, nucleotides in length and comprises a sequence that does not hybridize to either the first or second section.

The first hybrid in the treated sample is extended at the 3'-end of the first probe, thereby extending the first probe past the interrogation position and forming an extended first hybrid (FIG. 2B) whose sequence includes an interrogation position and a sequence complementary to the exogenous target sequence and the exogenous target sequence interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000, more preferably about 10 to about 200, most preferably about 10 to about 30 nucleotides in length and is complementary to the extended first probe at a position beginning about 5 to about 2000, preferably about 5 to about 200, nucleotides downstream of the interrogation position in extended first probe, is annealed to the extended first probe, thereby forming the second hybrid (FIG. 2C). The second hybrid is extended at the 3'-end of the second probe until that extension reaches the 5'-end of the extended first probe, thereby forming a second extended hybrid (FIG. 2D) whose 3'-region includes an identifier nucleotide.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

An aqueous composition of the extended second hybrid is denatured to separate the two nucleic acid strands; i.e., the extended second probe and the extended first probe. The aqueous composition so formed is cooled to form a "hairpin structure" from the separated extended second probe (FIG. 2E) when the target sequence is present in the original nucleic acid sample. Thus, when the exogenous target sequence is present in the original nucleic acid sample, the 3'-terminal sequence of the second extended probe in the second extended hybrid hybridizes with the sequence of the second extended probe from a region comprising the interrogation position and nucleotides downstream from the interrogation position of second extended probe to the nucleotide position where the 3'-terminal nucleotide of the original (first-named) probe annealed to the original target.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the exogenous nucleic acid target sequence. Again, the analytical output can be determined by one of the several methods discussed elsewhere herein.

As was the case in the previous embodiment, dNTPs are utilized in the extension reactions. It is preferred that the hairpin structures be separated from the dNTPs prior to depolymerization to enhance the analysis for the identifier nucleotide.

Kits

Other embodiments of the invention contemplate kits for determining the presence or absence of a predetermined exogenous nucleic acid target sequence in a nucleic acid sample. Such a kit comprises an enzyme whose activity is to release one or more nucleotides from the 3' terminus of a hybridized nucleic acid probe and at least one nucleic acid probe, said nucleic acid probe being complementary to the predetermined exogenous nucleic acid target sequence.

The kit optionally further comprises a nucleoside diphosphate kinase. Preferably, the nucleoside diphosphate kinase is that encoded by Pyrococcus furiosis. The kit optionally further comprises instructions for detecting the nucleic acid by depolymerization.

Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. Alternatively, the enzyme whose activity is to release nucleotides in the kit exhibits a 3' to 5' exonuclease activity, depolymerizing hybridized nucleic acids having one or more mismatched bases at the $_{3'}$ terminus of the hybridized probe.

It is to be understood that such a kit is useful for any of the methods of the present invention. The choice of particular components is dependent upon the particular method the kit is designed to carry out. Additional components can be provided for detection of the analytical output, as measured by the release of identifier nucleotide, or by detection of the remaining probe after depolymerization. For example, luciferase assay reagent can be provided in the kits of the invention for detection of an identifier nucleotide released from the 3'-terminal region of a probe.

The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In another embodiment, the invention contemplates a kit for determining the presence or absence of at least one predetermined exogenous nucleic acid target sequence in a nucleic acid sample comprising the following components: an enzyme whose activity, under depolymerizing conditions and in the presence of pyrophosphate is to release identifier nucleotide as a nucleoside triphosphate from hybridized nucleic acid probe; adenosine 5' diphosphate; pyrophosphate; a nucleoside diphosphate kinase; and at least one nucleic acid probe, wherein the nucleic acid probe is complementary to the predetermined exogenous nucleic acid target sequence.

Preferably, the enzyme whose activity in the presence of pyrophosphate is to release identifier nucleotides is the Tne triple mutant DNA polymerase, Klenow exo–, Klenow, T4 DNA polymerase, Ath DNA polymerase, Taq DNA polymerase and Tvu DNA polymerase, most preferably Tne triple mutant DNA polymerase, Klenow exo–, or Tvu DNA polymerase. In an alternative embodiment, a thermostable polymerase is preferred, wherein in the thermostable polymerase is preferably the Tne triple mutant DNA polymerase, T4 DNA polymerase, Ath DNA polymerase, Taq DNA polymerase and Tvu DNA polymerase, most preferably Tne triple mutant DNA polymerase, or Tvu DNA polymerase. Preferably, the nucleoside diphosphate kinase is that encoded by *Pyrococcus furiosis*. The kit optionally comprises instructions for use.

In another embodiment, the invention contemplates a kit for determining the presence or absence of a predetermined exogenous nucleic acid target sequence in a nucleic acid sample comprising an enzyme whose activity is to release one or more nucleotides from the 3' terminus of a hybridized nucleic acid probe and instructions for use. Such a kit optionally comprises a nucleoside diphosphate kinase. Preferably, the nucleoside diphosphate kinase is that encoded by *Pyrococcus furiosis*. The kit further optionally comprises a nucleic acid probe complementary to the predetermined exogenous nucleic acid target sequence.

In other embodiments of the present invention, nucleic acid detection test kits are provided for performing a depolymerization method contemplated by this invention, and particularly a depolymerization detection method.

In one embodiment, the kit includes a vessel containing an enzyme capable of catalyzing pyrophosphorolysis, including, but not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase, preferably a thermostable polymerase, most preferably Tne triple mutant polymerase or Tvu polymerase. In another embodiment, the kit contains a vessel that contains an exonuclease such as S1 nuclease, nuclease BAL 31, mung bean nuclease, exonuclease III and ribonuclease H.

Either of the above enzyme types is utilized in a contemplated method in a depolymerizing effective amount. That is, the enzyme is used in an amount that depolymerizes the hybridized probe to release an identifier nucleotide under depolymerizing conditions. This amount can vary with the enzyme used and also with the temperature at which depolymerization is carried out. An enzyme of a kit is typically present in an amount of about 0.1 to 100 U/reaction; in particularly preferred embodiments, the concentration is about 0.5 U/reaction. An amount of enzyme sufficient to carry out at least one assay, with its controls is provided.

As noted elsewhere, the preferred analytical output for determining the presence or absence of identifier nucleotide is luminescence caused by the reaction of ATP with luciferin in the presence of luciferase. A kit containing a pyrophosphorylation enzyme for use in DNA detection using luminescence also preferably includes a vessel containing NDPK and a vessel containing ADP. Similarly, a kit containing an exonuclease enzyme for use in DNA detection using luminescence also preferably includes a vessel containing PRPP synthetase and a vessel containing ADP. The NDPK or PRPP synthetase is provided in concentration of about 0.01 to 100 U/reaction, preferably about 0.1 to about 1.0 U/reaction.

Preferably, these reagents, and all of the reagents utilized in the kits discussed herein, are free of contaminating ATP and adenylate kinase. Some of the contaminants can be removed from the enzymes by dialysis treatment or by heat treatment.

Optionally, the kit contains vessels with reagents for amplification of dNTPs or NTP to ATP. Amplification reagents include, but are not limited to pyruvate kinase, adenylate kinase, NMPK, NDPK, AMP (e.g., as the amplification enzymes and substrate), and dCTP or AMP-CPP (e.g., as high-energy phosphate donors). In particularly preferred embodiments, the kit can be packaged in a single enclosure including instructions for performing the assay methods. In some embodiments, the reagents are provided in containers and are of a strength suitable for direct use or use after dilution. In alternative preferred embodiments, a standard set can also be provided in order to permit quantification of results. In yet other preferred embodiments, test buffers for optimal enzyme activity are included.

In yet other embodiments, a contemplated kit comprises a nuclease, PRPP synthetase, PRPP, NDPK, and ADP together with luciferase and luciferin. In preferred embodiments, the nuclease is provided in a concentration of about 1 to 500 U/reaction; in particularly preferred embodiments at a concentration of about 20 U/reaction. In a particularly preferred embodiment, the PRPP synthetase is provided in concentration of about 0.01 U/reaction to 10 U/reaction, preferably about 0.1 U/reaction. In some preferred embodiments, the kit includes all these reagents with luciferase and luciferin being provided as a single reagent solution.

In other preferred embodiments, these reagents include, but are not limited to, a high energy phosphate donor which cannot be utilized by luciferase, preferably dCTP, and AMP together with luciferase and luciferin. In alternative preferred embodiments, the kit includes all these reagents with luciferase and luciferin being provided in the same solution.

In still further embodiments of the present invention, the kits described above can contain a probe or probes for probe-mediated specific nucleic acid detection. In some embodiments, the kit contains at least one nucleic acid probe for a nucleic acid target of interest. In other embodiments, the kits contain multiple probes, each of which contain a different base at an interrogation position or which are designed to interrogate different target DNA sequences.

The types of nucleic acid probes that can be included in the kits and their uses are described in greater detail herein.

EXAMPLE 1
Reduction of Probe-alone Background Values For Probes Designed to Interrogate a Viral Sequence In this example, the background light values from probe-alone reactions are reduced by alteration of reaction conditions. More specifically, the values from such background reactions are reduced by lowering the Klenow exo– level in the reactions. In addition, the probes are used to assay the relative probe signal strength values for probes that hybridize to the same DNA strand versus probes that hybridize to different strands but that interrogate the same nucleotide polymorphism site.

Oligonucleotides CV11 (SEQ ID NO:1) and CV12 (SEQ ID NO:2) are a pair of single-stranded DNAs that can hybridize together to produce a segment of the genome of cytomegalovirus (CMV) in a form sensitive to the drug gancyclovir. Oligonucleotides CV13 (SEQ ID NO:3) and CV14 (SEQ ID NO:4) are a pair of single-stranded DNAs that can hybridize together to produce the same segment of the CMV genome, but differ from CV11 and CV12 in that they contain a SNP that represents a form of the virus resistant to the drug gancyclovir.

Probe oligonucleotide CV15 (SEQ ID NO:5) can hybridize with exact homology to a segment of CV12. Probe oligonucleotide CV16 (SEQ ID NQ:6) is identical to CV15 except that it contains a one base change from the CV15 sequence at the site of the SNP that confers drug resistance to the virus. Probe oligonucleatide CV17 (SEQ ID NO:7) can hybridize with exact homology to CV11. Probe oligonucleotide CV18 (SEQ ID NO:8) is identical to CV17 except that it contains a one base change from the CV17 sequence at the site of the SNP that confers drug resistance to the virus.

The oligonucleotides above were dissolved in water at a concentration of 1 mg/mnL and the following solutions were assembled.

| Solution | Oligonucleotide | Water |
|---|---|---|
| #1 | — | 20 µL |
| #2 | CV15, 1 µL | 19 µL |
| #3 | CV16, 1 µL | 19 µL |
| #4 | CV17, 1 µL | 19 µL |
| #5 | CV18, 1 µL | 19 µL |

These solutions were heated at 95° C. for 5 minutes, then cooled at room temperature for 10 minutes. The following master mix was assembled and mixed.

| Component | Amount |
|---|---|
| 10X DNA Pol Buffer (Promega, M195A) | 200 µL |
| Klenow exo- (1 U/µL) (Promega M218B) | 12.5 µL |
| 40 mM Sodium Pyrophosphate (Promega C350B) | 25 µL |
| NDPK (1 U/µL) | 10 µL |

-continued

| Component | Amount |
| --- | --- |
| 10 uM ADP (Sigma A5285) | 20 µL |
| Water | 732.5 µL |

Twenty microliters of this solution were added to solutions 1–5 above after they had cooled, and then the resulting mixtures were heated at 37° C. for 15 minutes. After this incubation, 4 µL of each solution were added to 100 µL of L/L reagent (Promega F202A) and the light production of the resulting solution was measured immediately using a Turner® TD 20/20 luminometer. The following results were obtained.

| Solution sampled | Relative light units |
| --- | --- |
| #1 | 13.07 |
| #2 | 14.98 |
| #3 | 14.27 |
| #4 | 28.25 |
| #5 | 583.70 |

These results demonstrate that probes CV15–CV17 provide relatively low probe-alone light signals at 0.25U Klenow exo– per reaction but that probe CV18-alone provides a very high relative light signal. The sequence of the CV18 probe can form a hairpin structure such that the terminal 3' bases hybridize to the sequence 5'TCGTGC 3' further towards the 5' end of the segment. Although probe CV17 could form the same structure, the terminal 3' base of the resulting structure would have a mispaired base.

These data exemplify one of the guiding principles of appropriate probe design for this system: the probes should not be predicted to form stable hairpin structure and, in particular, should not be predicted to give such a structure with the 3' end of the probe producing a structure that forms a blunt end or 5' overhang in the fragment as they may act as a substrate for the depolymerizing enzyme. In addition, the probes used should not be predicted to form probe dimer structures with either blunt ends or 5' overhanging ends because such probes can produce high probe-alone signals in the system and might make them unacceptable for use.

Due to their low background, probes CV15–CV17 were then selected for further study. Equal volumes of oligonucleotides CV11 and CV12 were annealed together, as described earlier in this example, as were CV13 and 14. The annealed solutions of CV11 and CV12, and CV13 and CV14 were labeled CV11+12 and CV13+14, respectively. The following solutions were assembled.

| Solution | CV15 | CV16 | CV17 | CV11 + 12 | CV13 + 14 | CV (11 + 12) + (13 + 14) Heteroxyg Template | Water |
| --- | --- | --- | --- | --- | --- | --- | --- |
| #1 | — | — | — | — | — | — | 20 µL |
| #2 | 1 µL | — | — | — | — | — | 19 µL |
| #3 | — | 1 µL | — | — | — | — | 19 µL |
| #4 | — | — | 1 µL | — | — | — | 19 µL |
| #5 | — | — | — | 1 µL | — | — | 19 µL |
| #6 | — | — | — | — | — | 1 µL | 19 µL |
| #7 | — | — | — | — | 1 µL | — | 19 µL |
| #8 | 1 µL | — | — | 1 µL | — | — | 18 µL |
| #9 | — | 1 µL | — | 1 µL | — | — | 18 µL |
| #10 | 1 µL | — | — | — | — | 1 µL | 18 µL |
| #11 | — | 1 µL | — | — | — | 1 µL | 18 µL |
| #12 | 1 µL | — | — | — | 1 µL | — | 18 µL |
| #13 | — | 1 µL | — | — | 1 µL | — | 18 µL |
| #14 | 1 µL | — | — | 1 µL | — | — | 18 µL |
| #15 | — | — | 1 µL | 1 µL | — | — | 18 µL |
| #16 | 1 µL | — | — | — | — | 1 µL | 18 µL |
| #17 | — | — | 1 µL | — | — | 1 µL | 18 µL |
| #18 | 1 µL | — | — | — | 1 µL | — | 18 µL |
| #19 | — | — | 1 µL | — | 1 µL | — | 18 µL |

These solutions were heated at 95° C. for 5 minutes and then permitted to cool for 10 minutes at room temperature. A master mix solution was assembled as in described in this Example, containing Klenow exo– at a final concentration of 0.25U/20 µL. After solutions 1–19 had cooled, 20 µL of the master mix solution were added and the resulting solution heated at 37° C. for 15 minutes. After this incubation, duplicate 4 µL samples of solutions 2–19 and a single sample of solution 1 were taken, added to 100 µL of L/L reagent (Promega, F202A) and the light production of the mixture measured immediately using a Turner® TD 20/20 luminometer. The following results were obtained.

| | Relative light units | |
| --- | --- | --- |
| Solution | Reading 1 | Reading 2 |
| #1 | 10.53 | — |
| #2 | 11.35 | 12.16 |
| #3 | 10.79 | 12.75 |
| #4 | 17.70 | 16.76 |
| #5 | 12.78 | 11.12 |
| #6 | 11.36 | 11.48 |
| #7 | 12.38 | 12.16 |
| #8 | 348.3 | 369.3 |
| #9 | 73.11 | 74.48 |
| #10 | 289.5 | 283.6 |
| #11 | 509.8 | 364.0 |
| #12 | 120.2 | 108.6 |
| #13 | 785.4 | 595.7 |
| #14 | 764.3 | 763.3 |

-continued

| | Relative light units | |
|---|---|---|
| Solution | Reading 1 | Reading 2 |
| #15 | 77.25 | 73.22 |
| #16 | 530.9 | 541.2 |
| #17 | 476.1 | 419.6 |
| #18 | 339.4 | 262.7 |
| #19 | 943.2 | 964.0 |

The net relative light values for the data above were calculated as follows. The ratios reported in this example were determined by first averaging the results from matching samples, then determining the net light production from the matching and mismatching samples and dividing the net light production from the matching reaction by that seen in the mismatch reaction. The net light production was determined by subtracting the estimated light contribution from the probes and template present in the reactions from the total light produced. The light production from the template reaction was considered to be the total of that contributed from the template specifically and that contributed by contaminating ATP from various components. The net increase from the probes alone was calculated by subtracting the average "No DNA" values from the probe values since this subtracts the contributions from contaminating ATP from the probe values. Thus, the formula used to determine the net light production from the reactions was:

Net Light=Total light−[(target alone)+(probe alone−No DNA)]

These values were used to determine the signal ratio by dividing the signal from the "C" allele probe by the signal from the "T" allele probe.

The results of these calculations are presented in the tables below, wherein "WT" indicates the wild type genotype.

| Probes Interrogate the Same DNA Strand Template Genotype | | | Probes Interrogate Different DNA Strands Template Genotype | | | |
|---|---|---|---|---|---|---|
| Probe | C/C | C/T | T/T | | C/C | C/T | T/T |
| WT Probe (CV15) | 345.5 | 274.0 | 100.8 | WT Probe (CV15) | 745.1 | 518.0 | 282.1 |
| Mutant Probe (CV16) | 60.5 | 424.3 | 677 | Mutant Probe (CV17) | 61.9 | 435.0 | 940 |
| Ratio | 5.7 | 1.5 | 0.15 | Ratio | 12 | 1.2 | 0.33 |

These data demonstrate that, for this particular SNP, probes that detect the polymorphism that bind to different strands provide the signal ratio closest to 1.0 when both nucleic acid targets are present in the reaction (as occurs for samples heterozygous for a particular allele). However either set of probes give clearly different signals depending upon the genotype of the sample DNA.

CV11 5'CGCTTCTACCACGAATGCTCGCAGAC-
CATGCTGCACGAATACGTCAGAAA-
GAACGTGGAGCGTCTGTTGGAGCT 3'    SEQ ID NO:1

CV12 5'CCAACAGACGCTCCACGTTCTTTCT-
GACGTATTCGTGCAGCATGGTCTGCGAG-
CATTCGTGGTAGAAGCGAGCT 3'    SEQ ID NO:2

CV13 5'CGCTTCTACCACGAATGCTCGCAGAT-
CATGCTGCACGAATACGTCAGAAA-
GAACGTGGAGCGTCTGTTGGAGCT 3'    SEQ ID NO:3

CV14 5' CCAACAGACGCTCCACGTTCTTTCT-
GACGTATTCGTGCAGCATGATCTGCGAG-
CATTCGTGGTAGAAGCGAGCT 3'    SEQ ID NO:4

CV15 5' CTACCACGAATGCTCGCAGAC 3'    SEQ ID NO:5

CV16 5' CTACCACGAATGCTCGCAGAT 3'    SEQ ID NO:6

CV17 5' TGACGTATTCGTGCAGCATGG 3'    SEQ ID NO:7

CV18 5' TGACGTATTCGTGCAGCATGA 3'    SEQ ID NO:8

EXAMPLE 2

Detection of DNA Sequences in the Genome of Listeria Species

This example provides an assay for the presence of DNA sequences present in the genome of Listeria in a gene known as the lap gene. Oligonucleotides LM1 (SEQ ID NO:9) and LM2 (SEQ ID NO:10) encode a segment of the lap gene and are exactly complementary to each other. Oligonucleotide probe LM3 (SEQ ID NO:11) was designed to hybridize exactly with a region of target LM2, and probe LM4 (SEQ ID NQ:12) was designed to hybridize exactly to target LM1.

Oligonucleotides LM1–LM4 were dissolved in TE buffer (10 mM Tris, 1 mM EDTA, pH8.0) at a concentration of 500 µg/mL and then were diluted 25-fold in TE buffer to obtain solutions at a DNA concentration of 20 ng/µL. The following solutions were assembled.

| Solution | Oligonucleotides | 1X TE Buffer |
|---|---|---|
| #1 | LM1, 10 µL | 10 µL |
| #2 | LM2, 10 µL | 10 µL |
| #3 | LM3, 10 µL | 10 µL |
| #4 | LM4, 10 µL | 10 µL |
| #5 | LM1, 10 µL; LM3, 10 µL | — |
| #6 | LM1, 10 µL; LM4, 10 µL | — |
| #7 | LM2, 10 µL; LM3, 10 µL | — |
| #8 | LM2, 10 µL; LM4, 10 µL | — |
| #9 | — | 20 µL |

These solutions were heated at 95° C. for 3 minutes, then permitted to cool at room temperature for 15 minutes. The following master mix was assembled.

| Component | Volume/reaction |
|---|---|
| Nanopure water (Promega AA399) | 12.75 µL |
| 10X DNA Polymerase Buffer (Promega M195A) | 2 µL |
| 40 mM Sodium Pyrophosphate (Promega C113) | 0.25 µL |
| ADP, 2 µM* | 1 µL |
| NDPK, 0.1 U/µL)** | 1 µL |
| Klenow Exo- 10 U/µL) (Promega M218) | 1 µL |

*Made by dissolving Sigma A5285 in water.
**Made by dissolving Sigma N0379 in water.

After solutions 1–9 had cooled, 2 µL samples of the solution were added to 18 µL of the master mix, in triplicate, the resulting solutions were mixed and incubated at 37° C. for 15 minutes. After this incubation, the tubes were placed on ice. Once all the incubations were on ice, 20 µL of the contents of the tubes were added to 100 µL of L/L reagent (Promega, F202A) and the light production of the resulting reaction was measured immediately using a Turners® TD 20/20 luminometer. The following data were obtained.

| | | Relative light units | | | | |
|---|---|---|---|---|---|---|
| Solution | Target | Probe | Reading 1 | Reading 2 | Reading 3 | Avg. |
| #1 | LM1 | — | 70.3 | 69.7 | 69.0 | 69.7 |
| #2 | LM2 | — | 39.6 | 40.8 | 45.3 | 41.9 |
| #3 | — | LM3 | 12.2 | 12.4 | 13.2 | 12.6 |
| #4 | — | LM4 | 16.9 | 17.3 | 17.4 | 17.2 |
| #5 | LM1 | LM3 | 57.7 | 76.5 | 72.7 | 69.0 |
| #6 | LM1 | LM4 | 1814 | 1815 | 1761 | 1797 |
| #7 | LM2 | LM3 | 56.72 | 61.1 | 57.59 | 58.5 |
| #8 | LM2 | LM4 | 67.5 | 72.4 | 79.3 | 73.1 |

These data show that LM4 produces a strong signal in the reaction with LM1 and thus can be used to detect this DNA sequence.

Oligonucleotides LM1 and LM2 were diluted to 2 ng/μL in 1× TE buffer. These materials were also used to create the following solutions in triplicate.

| Solution | LM1 | LM2 | LM3 | LM4 | 1X TE |
|---|---|---|---|---|---|
| #1 | 5 μL | 5 μL | — | — | 10 μL |
| #2 | 5 μL | 5 μL | 10 μL | — | — |
| #3 | 5 μL | 5 μL | — | 10 μL | — |

These solutions were heated to 95° C. for 10 minutes, then permitted to cool for 15 minutes at room temperature.

A master mix was made as described earlier in this example. After cooling at room temperature, 2 μL of each solution were added to an 18 μL sample of this master mix, and the resulting solutions were incubated at 37° C. for 15 minutes. After this incubation, 2 μL of the solution were added to 100 μL of L/L reagent (Promega, F202A) and the light produced was immediately read using a Turner® TD 20/20 luminometer. The following results were obtained.

| | Relative light units | | | | |
|---|---|---|---|---|---|
| Solution | Reading 1 | Reading 2 | Reading 3 | Avg. | NLU* |
| #1 | 754.4 | 727.8 | 752.7 | 745.0 | — |
| #2 | 857.4 | 801.0 | 852.3 | 836.9 | 91.9 |
| #3 | 1185 | 1211 | 1192 | 1196 | 451 |

*Net light units (NLU) were calculated by subtracting the no probe reaction average (#1) from the specific probe reaction values.

With both DNA template strands present, both probes provide signals above background.

The sequences used were as follows:

LM1 5' GAAGTAAAACAAACTACACAAGCAACTA-
CACCTGCGCCTAAAGTAGCAGAAAC-
GAAAGAAACTCCAGTAG 3'      SEQ ID NO:9

LM2 5' CTACTGGAGTTTCTTTCGTTTCTGC-
TACTTTAGGCGCAGGTGTAGTTGCTTGT-
GTAGTTTGTTTTACTTC 3'      SEQ ID NO:10

LM3 5' GCAACTACACCTGCGCCTAAAGTAG-
CAGAA 3'      SEQ ID NO:11

LM4 5' TTCTGCTACTTTAGGCGCAGGTGTAG-
TTCG 3'      SEQ ID NO:12

EXAMPLE 3

Detection of Segments of the Listeria hyl Gene

In this example, a method is described for the detection of a segment of the hyl gene from *Listeria mnonocyotogenes*.

Oligonucleotides LM5 (SEQ ID NO:13) and LM6 (SEQ ID NO:14) anneal exactly to create a region of the hyl gene. LM7 (SEQ ID NO:15) and LM8 (SEQ ID NO:16) oligonucleotides are used as interrogation probes with LM7 completely complementary to LM6 and LM8 completely complementary to LM5.

Oligonucleotides LM5–8 were dissolved in 1× TE buffer at a concentration of 500 μg/mL and then were diluted 25 fold in TE buffer to obtain solutions at a DNA concentration of 20 ng/μL. The following solutions were assembled.

| Solution | Oligonucleotides | 1X TE Buffer |
|---|---|---|
| #1 | LM5, 10 μL | 10 μL |
| #2 | LM6, 10 μL | 10 μL |
| #3 | LM7, 10 μL | 10 μL |
| #4 | LM8, 10 μL | 10 μL |
| #5 | LM5, 10 μL; LM7, 10 μL | — |
| #6 | LM5, 10 μL; LM8, 10 μL | — |
| #7 | LM6, 10 μL; LM7, 10 μL | — |
| #8 | LM6, 10 μL; LM8, 10 μL | — |
| #9 | — | 20 μL |

These solutions were heated at 95° C. for 3 minutes, then permitted to cool at room temperature for 15 minutes. The following master mix was assembled.

| | Volume/Reaction |
|---|---|
| Nanopure water (Promega AA399) | 12.75 μL |
| 10X DNA Polymerase Buffer (Promega M195) | 2 μL |
| 40 mM Sodium Pyrophosphate (Promega C113) | 0.25 μL |
| ADP, 2 μM* | 1 μL |
| NDPK, 0.1 U/μL)** | 1 μL |
| Klenow Exo- 10 U/μL) (Promega M128) | 1 μL |

*Made by dissolving Sigma A5285 in water.
**Made by dissolving Sigma N0379 in water.

After solutions 1–9 had cooled, triplicate 2 μL samples of the solution were added to 18 μL master mix and the resulting solutions were mixed and incubated at 37° C. for 15 minutes. After this incubation, the tubes were placed on ice. Once all the incubations were on ice, 20 μL of the contents of the tubes were added to 100 μL of L/L reagent (Promega F202A) and the light production of the resulting reaction was measured immediately using a Turner® TD 20/20 luminometer. The following data were obtained.

| | Relative light units | | | | |
|---|---|---|---|---|---|
| Solution | Reading 1 | Reading 2 | Reading 3 | Avg. | Net Ave |
| #1 | 28.53 | 29.62 | 30.0 | 29.41 | — |
| #2 | 81.30 | 75.12 | 74.68 | 77.03 | — |
| #3 | 19.88 | 13.12 | 12.80 | 15.26 | — |
| #4 | 1326 | 1273 | 1216 | 1271 | — |
| #5 | 37.24 | 36.40 | 36.77 | 36.80 | 3.78 |
| #6 | 2582 | 2336 | 2169 | 2362 | 1089 |
| #7 | 90.74 | 90.83 | 90.64 | 90.64 | 9.97 |
| #8 | 1596 | 1671 | 1787 | 1684 | 347.6 |
| #9 | 12.33 | 11.16 | 11.48 | 11.66 | — |

The above data indicate that at least oligonucleotide LM8 can be used to detect the target gene sequence represented in LM6.

Oligonucleotides LM5 and LM6 were diluted to 2 ng/μL in 1× TE buffer (10 mM Tris, 1 mM EDTA, pH 8.0). These materials were also used to create the following solutions in triplicate.

| Solution | LM5 | LM6 | LM7 | LM8 | 1X TE |
|---|---|---|---|---|---|
| #1 | 5 μL | 5 μL | — | — | 10 μL |
| #2 | 5 μL | 5 μL | 10 μL | — | — |
| #3 | 5 μL | 5 μL | — | 10 μL | — |

These solutions were heated to 95° C. for 10 minutes, and then cooled for 15 minutes at room temperature.

Then 2 μL of the solutions were added to triplicate 18 μL samples of the master mix and then the resulting solutions were incubated at 37° C. for 15 minutes. After this incubation, 2 μL of the solution were added to 100 μL of L/L reagent (Promega, F202A) and the light produced was immediately read using a Turner® TD 20/20 luminometer. The following results were obtained.

| | Relative light units | | | | |
|---|---|---|---|---|---|
| Solution | Reading 1 | Reading 2 | Reading 3 | Avg. | NLU* |
| #1 | 442.5 | 431.8 | 432.2 | 435.5 | — |
| #2 | 576.1 | 544.6 | 580.1 | 566.9 | 115.7 |
| #3 | 1779 | 1837 | 1908 | 1841 | 1405 |

*Net light units (NLU) determined by subtraction of probe alone values (see table above) and solution #1 values from the average light units measured.

These results demonstrate that specific detection of the segment of the hyl gene sequence from Listeria can be performed using the components described above. Because this gene sequence is specific for Listeria, this indicates that the components can be used for specific detection of Listeria DNA.

LM5 5' CATCGACGGCAACCTCGGAGACTTAC-
GAGATATTTTGAAAAAAGGCGCTACTTT-
TAATCGAGAAACACCA 3'  SEQ ID NO:13

LM6 5' TGGTGTTTCTCGATTAAAAGTAGCGC-
CTTTTTTCAAAATATCTCGTAAGTCTC-
CGAGGTTGCCGTCGATG 3+  SEQ ID NO:14

LM7 5' CTCGGAGACTTACGAGATATTTTGAA-
AAAA 3'  SEQ ID NO:15

LM8 5' TTTTTTCAAAATATCTCGTAAGTCTCC-
GAG 3'  SEQ ID NO:16

EXAMPLE 4

Detection of a DNA Sequence from Salmonella

In this example, a method for detection of a gene sequence from Salmonella is provided.

Oligonucleotides ST1 (SEQ ID NO:17), ST2 (SEQ ID NO:18), ST3 (SEQ ID NO:19), and ST4 (SEQ ID NO:20) were dissolved in 1× TE buffer to 500 μg/μL and then were diluted 25 fold in 1× TE buffer to obtain solutions at a DNA concentration of 20 ng/μL. The following solutions were prepared.

| Solution | Oligonucleotides | 1X TE Buffer |
|---|---|---|
| #1 | ST1, 10 μL | 10 μL |
| #2 | ST2, 10 μL | 10 μL |
| #3 | ST3, 10 μL | 10 μL |

-continued

| Solution | Oligonucleotides | 1X TE Buffer |
|---|---|---|
| #4 | ST4, 10 μL | 10 μL |
| #5 | ST1, 10 μL; ST3, 10 μL | — |
| #6 | ST1, 10 μL; ST4, 10 μL | — |
| #7 | ST2, 10 μL; ST3, 10 μL | — |
| #8 | ST2, 10 μL; ST4, 10 μL | — |
| #9 | — | 20 μL |

These solutions were heated at 95° C. for 3 minutes, then permitted to cool at room temperature for 15 minutes.
The following master mix was assembled.

| Component | Volume/reaction |
|---|---|
| Nanopure water (Promega AA399) | 12.75 μL |
| 10X DNA Polymerase Buffer (Promega M195) | 2 μL |
| 40 mM Sodium Pyrophosphate (Promega C113) | 0.25 μL |
| ADP, 2 μM* | 1 μL |
| NDPK, 0.1 U/μL** | 1 μL |
| Klenow Exo- 10 U/μL) (Promega M128) | 1 μL |

*Made by dissolving Sigma A5285 in water.
**Made by dissolving Sigma N0379 in water.

After solutions 1–9 had cooled, three 2 μL samples of the solution were added to 18 μL of the master mix and the resulting solution was mixed and incubated at 37° C. for 15 minutes. After this incubation, the tubes were placed on ice. Once all the incubations were on ice, 20 μL of the contents of the tubes were added to 100 μL of L/L reagent, and the light production of the resulting reaction was measured immediately using a Turner® TD 20/20 luminometer. The following data were obtained.

| | Relative light units | | | | |
|---|---|---|---|---|---|
| Solution | Reading 1 | Reading 2 | Reading 3 | Avg. | Net Avg. |
| #1 | 18.28 | 18.27 | 17.97 | 18.17 | — |
| #2 | 231.9 | 211.4 | 226.3 | 223.2 | — |
| #3 | 11.58 | 12.56 | 11.34 | 11.83 | — |
| #4 | 14.00 | 14.48 | 14.88 | 14.45 | — |
| #5 | 21.31 | 21.20 | 19.44 | 20.65 | 2.18 |
| #6 | 3003 | 2943 | 2918 | 2955 | 2933 |
| #7 | 2780 | 2782 | 2641 | 2734 | 2510 |
| #8 | 256.4 | 269.9 | 271.1 | 265.8 | 39.67 |
| #9 | 11.63 | 11.39 | 11.56 | 11.52 | — |

These data indicate that both oligonucleotide probes ST3 and ST4 can give a very strong specific light signals with single strand target DNA sequence from Salmonella.

Oligonucleotides ST1 and ST2 were diluted to 2 ng/μL in 1× TE buffer (10 mM Tris, 1 mM EDTA, pH 8.0). These materials were also used to create the following solutions in triplicate.

| Solution | ST1 | ST2 | ST3 | ST4 | 1X TE |
|---|---|---|---|---|---|
| #1 | 5 μL | 5 μL | — | — | 10 μl |
| #2 | 5 μL | 5 μL | 10 μL | — | — |
| #3 | 5 μL | 5 μL | — | 10 μL | — |

These solutions were heated to 95° C. for 10 minutes, then permitted to cool for 15 minutes at room temperature.

A master mix was made as described earlier in this example. After cooling at room temperature, 2 µL of each solution were added to an 18 µL sample of this master mix, and then the resulting solutions were incubated at 37° C. for 15 minutes. After this incubation, 2 µl of the solution were added to 100 µL of L/L reagent and the light produced was immediately read using a Turner® TD 20/20 luminometer. The following results were obtained.

| | Relative light units | | | | |
|---|---|---|---|---|---|
| Solution | Reading 1 | Reading 2 | Reading 3 | Avg. | NLU* |
| #1 | 692.5 | 728.9 | 678.3 | 699.9 | — |
| #2 | 2448 | 2389 | 2311 | 2382 | 1683 |
| #3 | 1742 | 1778 | 1738 | 1752 | 1053 |

*Net light units (NLU) were determined by subtraction of probe alone values (see table above) and solution #1 values from the average light units measured.

These data demonstrate that oligonucleotide probes ST3 and ST4 provide specific detection of the DNA target sequence from Salmonella even if both DNA strands are present.

Sequences used were as follows:

ST1 5' TTTAATTCCGGAGCCTGTGTAATGAAA-
GAAATCACCGTCACTGAACCTGCCTTTG-
TCACC 3'  SEQ ID NO:17

ST2 5' GGTGACAAAGGCAGGTTCAGTGACGGT-
GATTTCTTTCATTACACAGGCTCCGGAAT-
TAAA 3'  SEQ ID NO:18

ST3 5' TGTGTAATGAAAGAAATCACCGTCAC-
TGAA 3'  SEQ ID NO:19

ST4 5' TTCAGTGACGGTGATTTCTTTCATTAC-
ACA 3'  SEQ ID NO:20

EXAMPLE 5
Detection of a Specific Message by Use of a DNA Probe Exactly Matching the Message Sequence and Lack of a Signal When the DNA Probe Is Mismatched at Its 3' End In this Example, a luciferase light signal is generated from pyrophosphorylation of a DNA probe that complements the sequence of a target RNA species. In addition, evidence is presented to demonstrate that this signal is not generated if the 3'-terminal base of the probe does not complement the RNA base in the target sequence. These data demonstrate that probe pyrophosphorylation can be used to detect the presence of specific target RNA sequences and that mutations at specific bases in the target sequence can be detected by use of probes that should match the base but that do not give a signal with the message.

A master mix was assembled that contained:
Capped Kanamycin RNA (0.62 mg/mL) 1.25 µL
5x MMLV Reaction Buffer 50 µL
40 mM Sodium Pyrophosphate 2.5 µL
10 µM ADP 2.5 µL
NDPK (1 U/µL) 5 µL
MMLV-RT (200 U/µL)(Promega, M1701) 12.5 µL
Nanopure water 163.75 µL Probes one through four were dissolved at a concentration of 1 mg/mL in 1x TE buffer.

Probe 1 (SEQ ID NO:21) was designed to exactly complement a segment of the coding region of the Kanamycin RNA. Probe 2 (SEQ ID NO:22), Probe 3 (SEQ ID NO:23)and Probe 4 (SEQ ID NO:24) were designed to match the sequence of Probe 1 except that the 3'-terminal base of the probe was altered to one of each of the other three DNA bases at this position.

Nineteen microliters of the master reaction mix were placed in 10 labeled 0.5 mL microfuge tubes and the following additions were made to the tubes: Tubes 1 and 2, 1 µL 1x TE buffer; Tubes 3 and 4, 1 µL Probe 1; Tubes 5 and 6, 1 µL Probe 2; Tubes 7 and 8, 1 µL Probe 3; and Tubes 9 and 10, 1 µL Probe 4. The 10 0.5 mL microfuge tubes were incubated at 37° C. for 20 minutes to hybridize and form treated samples. Thereafter, 2 µL of the contents of the tubes were added to 100 µL L/L reagent (Promega, F202A) and the light output of the reagent was measured using a luminometer. The following data were collected.

| Solution | Relative Light Units |
|---|---|
| 1 | 3.989 |
| 2 | 3.458 |
| 3 | 49.95 |
| 4 | 52.24 |
| 5 | 3.779 |
| 6 | 3.727 |
| 7 | 4.394 |
| 8 | 4.163 |
| 9 | 7.879 |
| 10 | 7.811 |

These data show that MMLV-RT is able to pyrophosphorylate a DNA probe that hybridized to a target RNA sequence and that the free nucleoside triphosphates that are formed are converted to ATP equivalents that can be measured using luciferase. In addition, the data show that this signal is either absent or much weaker (solutions 1,2,5,6,7,8,9,10) when a probe with a 3' mismatch to the expected base is used in the reaction (compare to tubes 3 and 4).

Probe 1  SEQ ID NO:21  5'GCAACGCTACCTTTGCCATGTTTC 3'

Probe 2  SEQ ID NO:22  5'GCAACGCTACCTTTGCCATGTTTG 3'

Probe 3  SEQ ID NO:23  5'GCAACGCTACCTTTGCCATGTTTA 3'

Probe 4  SEQ ID NO:24  5'GCAACGCTACCTTTGCCATGTTTT 3'

EXAMPLE 6
Detection of a Specific RNA: Globin mRNA

In this Example, the light signal produced from pyrophosphorylation of DNA probes that are complementary to two regions of globin mRNA is compared to the signals from two DNA probes that are the exact sequence of the same regions. Once again, probes that totally complement the target RNA are shown to give a signal above background, whereas those that do not complement the target RNA give little or no signal.

Probe 5 (SEQ ID NO:25), Probe 6 (SEQ ID NO:26), Probe 7 (SEQ ID NO:27), and Probe 8 (SEQ ID NO:28) were diluted to a concentration of 0.5 mg/mL in 1x TE buffer (10 mM Tris, 1 mM EDTA). Purified globin mRNA (Gibco BRL, 18103-028) as target was dissolved in 1x TE buffer (10 mM Tris, 1 mM EDTA) to a concentration of 20 ng/µL.

Hybridization solutions were assembled as follows:
Solution 1: 10 µL Probe 5 and 10 µL Globin MRNA
Solution 2: 10 µL Probe 6 and 10 µL Globin mRNA
Solution 3: 10 µL Probe 7 and 10 µL Globin mRNA
Solution 4: 10 µL Probe 8 and 10 µL Globin mRNA
Solution 5: 10 µL Probe 5 and 10 µL 1x TE buffer
Solution 6: 10 µL Probe 6 and 10 µL 1x TE buffer
Solution 7: 10 µL Probe 7 and 10 µL 1x TE buffer
Solution 8: 10 µL Probe 8 and 10 µL 1x TE buffer
Solution 9: 10 µL 1x TE buffer, 10 µL Globin MRNA These solutions were assembled in 0.5 mL tubes, heated to 50° C. for 15 minutes and permitted to cool to room temperature for 15 minutes.

The following master reaction mixture was assembled:

| | |
|---|---|
| Nanopure water | 346.5 µL |
| MMLV-RT 5X Reaction Buffer (Promega M195A) | 132 µL |
| Sodium pyrophosphate (Promega M531) | 16.5 µL |
| NDPK (1 U/µL) | 33 µL |
| ADP (2 µM) | 33 µL |
| MMLV-RT (adjusted to 100 U/µL) (Promega, M1701) | 33 µL |

The solution above was mixed and 18 µL placed into 27 tubes. Three two-microliter samples of each of the hybridization solutions above were added in three of the tubes containing the master reaction mix and the tubes were then incubated at 37° C. for 15 minutes and permitted to cool to room temperature to hybridize and form treated samples. The contents of the tubes were then added to 100 µL of L/L reagent and the light production of the resulting reaction was measured immediately using a luminometer (Turner® TD20/20). The following results were obtained:

| Hybridization Solution | Light Values | | | Average |
|---|---|---|---|---|
| Probe 5 + RNA | 6.555 | 6.303 | 6.187 | 6.348 |
| Probe 5 + TE Buffer | 6.335 | 5.923 | 6.046 | 6.101 |
| Probe 6 + RNA | 137.8 | 128.5 | 169.2 | 145.2 |
| Probe 6 + TE Buffer | 10.24 | 9.429 | 9.858 | 9.842 |
| Probe 7 + RNA | 6.235 | 6.763 | 6.375 | 6.458 |
| Probe 7 + TE Buffer | 6.436 | 6.545 | 6.138 | 6.388 |
| Probe 8 + RNA | 90.34 | 95.42 | 54.7 | 80.15 |
| Probe 8 + TE Buffer | 10.21 | 12.55 | 9.372 | 10.71 |
| TE Buffer + RNA | 5.579 | 6.509 | 6.388 | 6.159 |

These data show that a strong light signal is seen when the reaction mixes containing probes 6 or 8 and target RNA were added to the L/L reagent but little signal was seen when the probes were incubated without target RNA, or when the target RNA was incubated without these probes. In addition, probes 5 and 7 provided very low signals in the presence or absence of added target RNA. Probes 6 and 8 were designed to complement two different regions in the coding region of globin mRNA. Probes 5 and 7 were made to exactly mimic the sequence of these same target RNA regions. Thus, these data provide a second example of how the pyrophosphorylation of a probe can be used to detect a specific RNA.

EXAMPLE 7

Specific Detection of RNA: Comparison of Signals From RNA Species that Match Probe Sequences in Reactions With and Without Added Extraneous Target RNA For the pyrophosphorylation reaction described in Example 8 to be used to detect specific target sequences, another requirement of the system is that the probes should give a very similar signal in the presence and absence of extraneous RNA. In this example, the strength of the signal of probes designed to detect target globin mRNA in the presence of a large amount of yeast RNA is compared to the signal seen in the absence of added yeast RNA. Hybridization solutions containing various levels of yeast RNA, Probe 6 (SEQ ID NO:26) or Probe 8 (SEQ ID NO:28) and target globin MRNA (Gibco BRL, 18103-028) were assembled by adding 5 µL 500 ng/µL either probe 6 or probe 8 to 5µL 40 ng/µL of target globin mRNA and 10 µL yeast RNA (Sigma Chemical Co. R3629) in 1× TE buffer (10 mM Tris, 1 mM EDTA) to produce solutions containing total amounts of yeast RNA of 0, 2, 20, 200, 400, and 800 ng. The solutions were heated at 50° C. for 15 minutes and then permitted to cool to room temperature for 15.

Reaction master mix was assembled as in Example 2 above and 18 µL of the mix were placed in 18 tubes. After cooling 15 minutes, 2 µL of the various hybridization solutions containing probe 6 were added to the tubes and the tubes were placed in a 37° C. heating block.

After 15 minutes of incubation of the hybridization mixture with the reaction master mix, 20 µL of the solution were added to 100 µL of L/L reagent (Promega, F202A) and the light output of the resulting reaction was measured using a Turner® TD-20/20 luminometer.

After the probe 6 data were collected, an identical set of reactions was performed using the hybridization solutions containing probe 8. The following data were obtained:

| | Probe 6 Reactions | | | |
|---|---|---|---|---|
| Yeast RNA | relative light units | | | Average |
| None | 96 | 109 | 111 | 105.3 |
| 2 ng | 98.4 | 85.0 | 118.5 | 100.7 |
| 20 ng | 117.9 | 110.9 | 82.7 | 103.65 |
| 200 ng | 56.4 | 110.1 | 93.2 | 86.6 |
| 400 ng | 115.7 | 110.7 | 124.6 | 117 |
| 800 ng | 127.6 | 128.7 | 143.1 | 133.1 |

| | | |
|---|---|---|
| Probe 5 | SEQ ID NO: 25 | 5'ATGGTGCATCTGTCCAGTGAGGAGAAGTCT3' |
| Probe 6 | SEQ ID NO: 26 | 5'AGACTTCTCCTCACTGGACAGATGCACCAT3' |
| Probe 7 | SEQ ID NO: 27 | 5'GCTGCTGGTTGTCTACCCATGGACCC3' |
| Probe 8 | SEQ ID NO: 28 | 5'GGGTCCATGGGTAGACAACCAGCAGC3' |

Probe 8 Reactions

| Yeast RNA | relative light units | | | Average |
|---|---|---|---|---|
| None | 105.8 | 97.0 | 82.3 | 95.0 |
| 2 ng | 84.5 | 84.6 | 93.7 | 87.6 |
| 20 ng | 99.6 | 111.7 | 104.9 | 105.4 |
| 200 ng | 83.6 | 75.9 | 95.6 | 85.1 |
| 400 ng | 94.7 | 97.2 | 81.9 | 91.2 |
| 800 ng | 50.7 | 89.0 | 82.1 | 73.9 |

These data indicate that addition of very large amounts of yeast RNA to the hybridization reaction does not greatly lower the signal from hybridized probes for specific target RNA species.

| | | |
|---|---|---|
| Probe 6 | SEQ ID NO: 26 | 5'AGACTTCTCCTCACTGGACAGATGCACCAT3' |
| Probe 8 | SEQ ID NO: 28 | 5'GGGTCCATGGGTAGACAACCAGCAGC3' |

EXAMPLE 8
Initial Detection Limit For Plasmid Target DNA By Use of Probe Pyrophosphorylation In the previous two examples, plasmid target DNA was specifically detected using probes that hybridized to a target sequence in the DNA. In this example, a titration of target DNA is carried out in the pyrophosphorylation reaction to determine the level of DNA needed to obtain a signal from this reaction.

The Sph I cut target pKAN DNA (40,000 pg/μL) was serially diluted using nuclease-free water to obtain concentrations of 10,000, 2,500, 625, 156 and 39 pg/μL. Duplicate solutions containing 1 μL each of these DNA target solutions, 1 μL Probe 1 (SEQ ID NO:21) and 18 μL nuclease-free water were assembled as were a pair of solutions containing 1 μL Probe 1 and 19 μL of nuclease-free water. All of these solutions were heated at 95° C. for 3 minutes and then cooled for 10 minutes to room temperature to permit hybridization and form a treated sample.

A 2× Master Mix was assembled as follows:
40 μL 10× DNA Polymerase buffer (Promega, M195A)
10 μL 40 mM Sodium Pyrophosphate
10 μL (10 U/μL) Klenow exo minus DNA Polymerase (Promega, M128B)
2 μL NDPK at a concentration of 1 U/μL
4 μL 10 μM ADP
134 μL nuclease-free water The Master Mix components were mixed and 20 μL 2× Master Mix were added to each of the solutions and incubated at 37° C. for 20 minutes. A sample containing 4 μL of the solution was then added to 100 μL of L/L reagent (Promega, F202A) and the light produced by the reaction was immediately measured using a Turner® 20/20 luminometer. The following data were obtained.

Data Table

| Reaction | DNA Assayed* | Light Units |
|---|---|---|
| #1 | 4000 pg | 168.4 |
| #2 | 4000 pg | 169.4 |
| #3 | 1000 pg | 57.7 |
| #4 | 1000 pg | 77.9 |
| #5 | 250 pg | 19.3 |
| #6 | 250 pg | 21.1 |
| #7 | 62.5 pg | 6.3 |
| #8 | 62.5 pg | 6.4 |
| #9 | 15.6 pg | 2.4 |
| #10 | 15.6 pg | 2.3 |
| #11 | 3.9 pg | 1.4 |
| #12 | 3.9 pg | 1.4 |
| #13 | 0 pg | 1.1 |
| #14 | 0 pg | 1.4 |

*This number reflects that relative amount of DNA transferred to L/L solution.

These data demonstrate that the detection limit for DNA by this reaction under these conditions is at least about 62.5 pg of DNA and is more likely about 15.6 pg of DNA or less.

| | | |
|---|---|---|
| Probe 1 | SEQ ID NO: 21 | 5'GCAACGCTACCTTTGCCATGTTTC3' |

EXAMPLE 9
Detection of β-galactosidase Target Sequences in Plasmids

In this example, two probes are used that complement each other exactly. One of the probes matches the sequence of the β-galactosidase gene exactly (sense orientation) and the other probe exactly matches the complementary strand (antisense orientation) of that gene. This example demonstrates that, whereas both probes can be used to detect the presence of the target β-galactosidase gene in plasmid DNA, the level of background signal given by reactions containing only probe DNA can be very different.

Probe 23 (SEQ ID NO:29) and Probe 24 (SEQ ID NO:30) were dissolved as described above to a concentration of 500 ng/μL and then diluted in nuclease-free water to 100 and 20 ng/μL. Plasmid pGEM7zf+ (Promega) was digested with Sac I (Promega) as the target and diluted to give a solution containing 20 ng of plasmid target DNA/μL of solution.

The following solutions were assembled:

| Solution | Plasmid DNA (μL) | Probe, Concentration | H₂O (μL) |
|---|---|---|---|
| #1 | 1 | (none, 1 μL of 1 X TE buffer added) | 18 |
| #2 | 0 | 1 μL Probe 23, 500 ng/μL | 19 |
| #3 | 0 | 1 μL Probe 23, 100 ng/μL | 19 |
| #4 | 0 | 1 μL Probe 23, 20 ng/μL | 19 |

-continued

| Solution | Plasmid DNA (μL) | Probe, Concentration | H₂O (μL) |
|---|---|---|---|
| #5 | 1 | 1 μl Probe 23, 500 ng/μL | 18 |
| #6 | 1 | 1 μL Probe 23, 100 ng/μL | 18 |
| #7 | 1 | 1 μL Probe 23, 20 ng/μL | 18 |
| #8 | 0 | 1 μL Probe 24, 500 ng/μL | 19 |
| #9 | 0 | 1 μL Probe 24, 100 ng/μL | 19 |
| #10 | 0 | 1 μL Probe 24, 20 ng/μL | 19 |
| #11 | 1 | 1 μL Probe 24, 500 ng/μL | 18 |
| #12 | 1 | 1 μL Probe 24, 100 ng/μL | 18 |
| #13 | 1 | 1 μL Probe 24, 20 ng/μL | 18 |

These solutions were heated at 95° C. for 3 minutes, and cooled to room temperature to form hybrids and treated samples. Then, 20 μL of 2× Master Mix made as described in Example 8 were added and the solutions incubated for another 20 minutes at 37° C. Four microliters of each solution were then added to 100 μL of L/L reagent (Promega, F202A) and the light output of the reaction immediately measured using a Turner® TD20/20 luminometer. The following data were obtained.

| Reaction | Light Output | Net Light Output* |
|---|---|---|
| #1 | 2.8 | |
| #2 | 4.0 | |
| #3 | 1.9 | |
| #4 | 1.3 | |
| #5 | 52.4 | 45.6 |
| #6 | 13.6 | 8.9 |
| #7 | 4.1 | 0 |
| #8 | 34.3 | |
| #9 | 6.6 | |

-continued

| Reaction | Light Output | Net Light Output* |
|---|---|---|
| #10 | 1.7 | |
| #11 | 59.8 | 22.7 |
| #12 | 19.3 | 9.9 |
| #13 | 6.0 | 1.5 |

*Net light output is calculated by subtracting the probe alone and DNA alone values from that obtained with both components present.

These data indicate that both probes can be used to generate a signal indicating the presence of the target region encoding the β-galactosidase gene matching the probes is present in the plasmid. They also demonstrate that the level of signal produced with a probe in the absence of target DNA can vary and that the signal from a probe and the complement of that probe are not necessarily equal.

| Probe 23 | SEQ ID NO: 29 | 5'CAGTCACGACGTTGTAAAACGACGGCCAGT3' |
| Probe 24 | SEQ ID NO: 30 | 5'ACTGGCCGTCGTTTTACAACGTCGTGACTG3' |

EXAMPLE 10
Detection of Specific Target DNA Sequences on Lambda DNA

In this example, detection of the target β-galactosidase gene in the DNA of a recombinant Lambda phage is demonstrated.

Duplicate solutions were made that contained: Solution 1 and 2, 1 μL 300 ng/μL of Lambda gt11 DNA and 19 μL of nuclease-free water; Solution 3 and 4, 1 μL 500 ng/μL Probe 23 (SEQ ID NO:29) and 19 μL nuclease-free water; Solution 5 and 6, 1 μL 300 ng/μL Lambda gt11 DNA, 1 μl 500 ng/μL Probe 23, and 18 μL of nuclease-free water. All of these solutions were heated at 95° C. for 3 minutes and then cooled to room temperature for 10 minutes to permit hybridization to occur between complementary strands and form treated samples. At this point, 20 μl of 2× master mix made as described in above in this example were added and the solutions incubated for another 20 minutes at 37° C. A 4 μL sample of each pyrophosphorolysis reaction was then taken and added to 100 μL of L/L reagent (Promega, F202A) and the light production of the solution immediately measured with a Turner® TD20/20 luminometer. The following data were obtained.

| Reaction | DNA Components | Light Units |
|---|---|---|
| #1 | Target Lambda DNA | 16.5 |
| #2 | Target Lambda DNA | 7.4 |
| #3 | Probe 23 | 2.9 |
| #4 | Probe 23 | 2.9 |
| #5 | Target Lambda DNA and Probe 23 | 88.1 |
| #6 | Target Lambda DNA and Probe 23 | 70.4 |

These data indicate that the pyrophosphorylation system can be used to detect a probe hybridized to specific target sequences on lambda gt11 DNA.

| Probe 23 | SEQ ID NO: 29 | 5'CAGTCACGACGTTGTAAAACGACGGCCAGT3' |

EXAMPLE 11

Detection of DNA Sequences in the Genome of *Campylobacter jejuni*

Oligonucleotides 11453 (SEQ ID NO:31) and 11454 (SEQ ID NO:33) are exactly complementary and can be annealed, thereby forming a synthetic target representing a 70 bp segment of *Canipylobacter jejuni*. These two oligonucleotides were diluted in nanopure water to a final concentration of 10 μg/mL. Four microliters of each were then mixed with 232 μL 10 mM Tris pH7.3 to yield a target solution of 0.3 μg/mL of DNA. Oligonucleotides 11451 (SEQ ID NO:32) and 11450 (SEQ ID NO:34) are *Camrpy*- lobacter jejuni interrogation probes that bind to opposite strands of the bacterial genome represented in the synthetic target. Oligonucleotide 11451 anneals to oligonucleotide 11454. Oligonucleotide 11450 anneals to oligo 11453.

The following solutions were assembled in triplicate and nanopure water added to a final volume of 20 μL.

| Solution | 0.3 ng Target | 1 μg Probe | rlu |
|---|---|---|---|
| 1. | + | 11451 | 391 |
| 2. | + | 11450 | 241 |
| 3. | + | none | 28 |
| 4. | − | 11451 | 248 |
| 5. | − | 11450 | 30 |
| 6. | − | none | 24 |

The assembled solutions were incubated at 92° C. for 5 minutes, then cooled at room temperature for 10 minutes. Master mix was prepared as in Example 1 using 10 units Klenow exo– polymerase and 4 units NDPK. Twenty microliters of master mix were added to each tube and incubated at 37° C. for 15 minutes. Five microliters of each solution were then combined with 100 μL of L/L reagent (Promega F202A) and light output measured immediately on a Turner® TD20/20 luminometer. The average relative light units (rlu) are recorded in the table above Using each of the interrogation probes with the target appears to give strong net signal. The top probe (11451) however, gives very strong signal alone, possibly due to hairpin formation, and is less suitable for interrogation. The bottom interrogation probe (11450) is the better for interrogation.

11453 5' TTGAAGCATAGTTCTTGTTTT-
TAAACTTTGTCCATCTTGAGCCGCT-
TGAGTTGCCTTAGTTTTAATAGT 3'        SEQ ID NO:31
11454 5' ACTATTAAAACTAAGGCAACTCAAGCG-
GCTCAAGATGGACAAAGTTTAAAAACAA-
GAACTATGCTTCAAG 3'                SEQ ID NO:33
11451 5' AGTTCTTGTTTTTAAACTTTGTCCAT-
CTTG 3'                           SEQ ID NO:32
11450 5' CAAGATGGACAAAGTTTAAAAACAAG-
AACT 3'                           SEQ ID NO:34

EXAMPLE 12
Interrogation For Loss of Heterozygosity—CMV

The use of an interrogation assay to determine loss of heterozygosity with a synthetic cytomegalovirus (CMV) target is demonstrated in this example.

The CMV target was chosen because the interrogating probe oligonucleotides 9211 (SEQ ID NO:35) and 9212 (SEQ ID NO:36) had been previously used and well characterized. Oligonucleotides 10800 (SEQ ID NO:37) and 10801 (SEQ ID NO:38) were annealed to produce a synthetic target, "A", representing a fragment of the CMV genome. Likewise, oligonucleotides 10803 (SEQ ID NO:39) and 10805 (SEQ ID NO:40) were annealed to produce a synthetic target, "G" representing a fragment of the CMV genome. Targets A and G are identical except at one nucleotide position where they have the nucleotide resulting in their name. Both targets have SacI overhangs.

The targets were cloned into the SacI restriction site of pZERO-2 plasmid (Invitrogen) and transformed into TOP10 E. coli cells (Invitrogen). The presence of the correct nucleotide sequence in the A and G clones was confirmed by sequencing. However, the G clone was found to contain an unintended mutation at the nucleotide position three bases in from the 5' end of the region that anneals to the interrogation probes. Because this mismatch is near the 5' end of the interrogation probe annealing sequence, it should not affect the interrogation results.

The following five target solutions were created with the A and G clones:

1. Hetero: 125 pg A and 125 pg G/microliter
2. LOH A: 125 pg A and no G/microliter
3. LOH G: no A and 125 pg G/microliter
4. Mix Ag: 125 pg A and 62 pg G/microliter
5. Mix Ga: 62 pg A and 125 pg G/microliter These target solutions were PCR amplified with the JH67 (SEQ ID NO:41) and 11077 (SEQ ID NO: 42) probes in the following reaction:

2 μL Target solution
1 μL Probes JH67 and 11077 (50 pmol each)
1 μL 10 mM dNTPs
5 μL 10× Taq buffer
1 μL Taq DNA polymerase
40 μL water The PCR cycling parameters were: 96° C., 1 minute; (94° C., 15 seconds; 60° C., 30 seconds; 72° C., 45 seconds)×15; 72° C., 45 seconds. The entire PCR reaction was then purified with 500 μL Wizard™ PCR purification resin (Promega, A7170) according to manufacturer's instructions. The DNA was eluted with 30 μL TE buffer. A standard interrogation reaction with 6 μL target and 1 μg interrogation probe, was performed with the exception that 2 units of Klenow exo– were used per reaction. Four microliters of the final reaction were combined with 100 μL of L/L reagent and the relative light units measured.

|  | Heterozygote |  | LOH A |  | LOH G |  | Mix Ag |  | Mix Ga |  | Oligo Alone |
|---|---|---|---|---|---|---|---|---|---|---|---|
| No oligo | 30 | 40 | 65 | 29 | 34 | 51 | 19 | 59 | 26 | 41 | — |
| A oligo | 279 | 340 | 74 | 329 | 27 | 27 | 258 | 309 | 50 | 164 | 5.2 |
|  | 308 | 372 | 76 | 339 | 20 | 26 | 351 | 330 | 83 | 167 | 5.2 |
| G oligo | 302 | 324 | 37 | 91 | 285 | 272 | 127 | 106 | 245 | 302 | 6.3 |
|  | 278 | 325 | 30 | 87 | 256 | 187 | 113 | 124 | 215 | 357 | 6.3 |
| A:G ratio | 1.01 | 1.10 | 2.26 | 3.76 | 0.09 | 0.11 | 2.54 | 2.78 | 0.29 | 0.50 |  |
| G:A ratio | 0.99 | 0.91 | 0.44 | 0.27 | 11.59 | 8.71 | 0.39 | 0.36 | 3.46 | 1.99 |  |

These data illustrate that LOH can be determined using this method with appropriate interrogation probes.

10800 5' CGTGTATGCCACTTTGATATTACAC-
CCATGAACGTGCTCATCGACGTGAAC-
CCGCACAACGAGCT 3'                 SEQ ID NO:37
10801 5' CGTTGTGCGGGTTCACGTCGATGAG-
CACGTTCATGGGTGTAATATCAAAGTG-
GCATACACGAGCT 3'                  SEQ ID NO:38

10803 5' CGTGTATGCCACTTTGATATTACAC-
CCGTGAACGTGCTCATCGACGTGAAC-
CCGCACAACGAGCT 3'  SEQ ID NO:39

10805 5' CGTTGTGCGGGTTCACGTCGATGAG-
CACGTTCACGGGTGTAATATCAAAGTG-
GCATACACGAGCT 3'  SEQ ID NO:40

JH67 5' TCACACAGGAAACAGCTATGAC-
CATG 3'  SEQ ID NO:41

11077 5' GCAAGGCGATTAAGTTGGGTAACG 3' (M13 forward probe)  SEQ ID NO:42

9211 5' CACTTTGATATTACACCCATG 3'  SEQ ID NO:35

9212 5' CACTTTGATATTACACCCGTG 3'  SEQ ID NO:36

EXAMPLE 13
Determination of Viral Load

This example illustrates that the presence of viral nucleic acid in serum samples can be determined to a detection level of ten copies of viral nucleic acid per sample.

Hepatitis C Virus (HCV) RNA was isolated from infected or uninfected human serum samples. A two-step RT-PCR was performed using HCV-specific probes and about 1000 viral equivalents of RNA, and samples were interrogated using the interrogation probe HCV1 (SEQ ID NO:43).

Two HCV positive samples, one HCV negative sample, and a water control were analyzed in duplicate. The interrogation reaction was added to 100 µL of L/L reagent (Promega F202A) and the light output measured immediately on a Turner® TD20/20 luminometer. The average relative light unit values were as follows.

| | |
|---|---|
| Water control | 38.6 |
| HCV minus | 239.0 |
| HCV positive (1) | 1261.0 |
| HCV positive (2) | 1390.0 |

To determine the sensitivity of viral detection using this technology, RT-PCR was performed on HCV positive and HCV negative controls as well as samples estimated to contain 1000, 100, and 10 viral RNA copies. Twenty five microliters of each amplification reaction were purified using magnetic silica as follows, and eluted in 100 µL water.

1. 200 µL of a slurry containing 15 µL MagneSil™ paramagnetic particles (Promega) in solution containing 0.4 M guanidine thiocyanate and 0.08 M potassium acetate were added to each sample.
2. The MagneSil™ paramagnetic particles were mixed in the solutions and held against the side of the tube with a magnet.
3. The particles were washed twice with 200 µL of 70% ethanol by addition of the solution to the tubes, resuspension of the particles in the solution, recapture of the particles against the tube walls with the magnet and removal of the particle-free solution.
4. The particles were resuspended in fifty microliters of water.
5. 200 µL 0.4 M GTC and 0.08 M potassium acetate were added to each.
6. Step 2 was repeated as described above except that three washes with 70% ethanol were performed.
7. The particles were resuspended in 100 µL water, the particles were captured against the side of the tube, and the solution containing the purified DNA was transferred to a new tube.

Four microliters of the eluted DNA were interrogated using 1 microliter of the interrogation probe diluted to a total of twenty microliters with water. The nucleic acid solutions were heated to 95° C. for three minutes, then placed in a 37° C. incubator for 10 minutes. The following master mix was assembled:

| | |
|---|---|
| 10X DNA Polymerase Buffer (Promega M195) | 20 µL |
| 40 mM Sodium Pyrophosphate (Promega C113) | 5 µL |
| 10 U/µl Klenow Exo Minus (Promega M218) | 5 µL |
| NDPK (Sigma, NO379 at 10 U/µL in water) | 1 µL |
| ADP (Sigma A5285, 10 µM in water) | 2 µL |
| Water | 67 µL |
| | 100 µL |

Twenty microliters of master mix were added to each of the heated nucleotide mixes after incubation at 37° C. for 10 minutes. The resulting reactions were incubated for 15 minutes at 37° C. and then added to 100 µL L/L reagent (Promega, F202A) and the light produced was immediately read using a Turner® TD20/20 luminometer. The interrogation reaction was added to 100 µL of L/L reagent and the light output measured on a Turner® TD 20/20 luminometer. Ten copies of HCV are readily detected in this assay. The average relative light unit (rlu) values were as follows.

| Sample | rlu |
|---|---|
| Water | 49.0 |
| Water | 54.2 |
| HCV neg control | 59.4 |
| HCV neg control | 62.1 |
| HCV pos control | 653.7 |
| HCV pos control | 743.1 |
| HCV 1000 copies | 460.7 |
| HCV 1000 copies | 429.5 |
| HCV 100 copies | 405.1 |
| HCV 100 copies | 404.3 |
| HCV 10 copies | 184.9 |
| HCV 10 copies | 179.5 |

HCV1: 5' CTGCTAGCCGAGTAGTGTTGGGTCGC-
GAAAGGCCTTGTGG 3'  SEQ ID NO:43

EXAMPLE 14
Interrogation of DNA Sequences From Genetically Modified Organisms According to European Union (EU) Regulation on Novel Foods and Novel Food Ingredients, adopted in 1997, genetically modified foods must be labeled as such if they are "no longer equivalent" to their conventional counterparts. This includes when the foods have a different composition, use or nutritional value from the conventional food. The EU subsequently decided that the presence of just a fragment of genetically modified protein or DNA is enough to make the product "no longer equivalent" to conventional products for soya and maize and, therefore, such products require labeling.

Genetically modified organisms (GMO), particularly plants, are often genetically modified to include the exogenous specific DNA of interest along with an exogenous transcription sequence such as the 35S promoter and the NOS terminator. In this example, the DNA of soya and maize samples are analyzed for the presence or absence of the 35S promoter and NOS terminator. The PCR Primers 35S-1 (SEQ ID NO:44) and 35S-2 (SEQ ID NO:45) were used to prepare a 235 bp PCR product. The Primers NOS-1 (SEQ ID NO:46) and NOS-2 (SEQ ID NO:47) were used to prepare a 220 bp PCR product.

GMO positive and negative control DNA (20 ng) were PCR amplified using 50 pmol of the 35S promoter and NOS terminator PCR primer pairs. The PCR cycling profile was 94° C., 3 minutes; (94° C., 30 seconds; 54° C., 40 seconds; 72° C., 1 minute)×40; 72° C., 3 minutes. The resulting PCR products (25 µL) were purified using magnetic silica and eluted in 100 µL water as described in Example 13. Four microliters of the eluted PCR products were used in a standard interrogation assay as described in Example 13 and the relative light unit (rlu) results are detailed in the following table. The 35S interrogation probes used were 11211 (SEQ ID NO:48) and 11210 (SEQ ID NO:49). The NOS interrogation probes used were 11212 (SEQ ID NO:50) and 11213 (SEQ ID NO:51).

| DNA | PCR Oligos | Interrogation Oligos | rlu |
| --- | --- | --- | --- |
| GMO minus, soy | 35S | 11210 | 166.6 |
| GMO minus, soy | 35S | 11210 | 172.0 |
| GMO minus, soy | 35S | 11211 | 206.8 |
| GMO minus, soy | 35S | 11211 | 205.8 |
| GMO minus, soy | 35S | none | 95.7 |
| GMO minus, maize | 35S | 11210 | 245.0 |
| GMO minus, maize | 35S | 11210 | 254.3 |
| GMO minus, maize | 35S | 11211 | 271.3 |
| GMO minus, maize | 35S | 11211 | 275.7 |
| GMO minus, maize | 35S | none | 116.0 |
| GMO positive, soy | 35S | 11210 | 1456.0 |
| GMO positive, soy | 35S | 11210 | 1442.0 |
| GMO positive, soy | 35S | 11211 | 1546.0 |
| GMO positive, soy | 35S | 11211 | 1529.0 |
| GMO positive, soy | 35S | none | 865.0 |
| GMO positive, maize | 35S | 11210 | 1252.0 |
| GMO positive, maize | 35S | 11210 | 1299.0 |
| GMO positive, maize | 35S | 11211 | 1358.0 |
| GMO positive, maize | 35S | 11211 | 1361.0 |
| GMC positive, maize | 35S | none | 705.6 |
| GMO minus, soy | NOS | 11212 | 73.9 |
| GMO minus, soy | NOS | 11213 | 75.8 |
| GMO minus, soy | NOS | none | 76.1 |
| GMO positive, soy | NOS | 11212 | 615.0 |
| GMO positive, soy | NOS | 11213 | 616.6 |
| GMO positive, soy | NOS | none | 98.0 |

The above data demonstrate that the interrogation reaction works for the identification of presence or absence of GMO DNA in DNA samples isolated from soy and maize products. The 35S PCR product gave high background values by itself, which can be reduced by using a primer with phosphorothioate linkages near the 5'-terminus for the PCR reaction followed by exo6 treatment to remove one strand of the PCR product as described in Example 13 and below. The PCR primers 35S1 and NOS1 were resynthesized to have phosphorothioate linkages between the first five bases at the 5' end. The PCR reaction was repeated and the resulting PCR product treated with Exo6 and purified as described in Example 13.

Four microliters of the purified DNA were used for the standard interrogation assay using the NOS primer 11212 and the 35S primer 11211 with 5 units of Klenow exo-. The rlu data obtained are in the table below.

| DNA | PCR oligos | Interrogation oligo | rlu |
| --- | --- | --- | --- |
| GMO minus, soy | NOS | 11212 | 52.3 |
| GMO minus, soy | NOS | 11211 | 60.2 |
| GMO minus, soy | NOS | none | 53.3 |
| GMO positive, soy | NOS | 11212 | 277.1 |
| GMO positive, soy | NOS | 11211 | 84.4 |
| GMO positive, soy | NOS | none | 75.7 |
| GMO minus, soy | 35S | 11212 | 57.8 |
| GMO minus, soy | 35S | 11211 | 66.9 |
| GMO minus, soy | 35S | none | 54.6 |
| GMO positive, soy | 35S | 11212 | 99.7 |
| GMO positive, soy | 35S | 11211 | 397.6 |
| GMO positive, soy | 35S | none | 86.0 |
| GMO positive, soy | 35S + NOS | 11212 | 249.4 |
| GMO positive, soy | 35S + NOS | 11211 | 290.1 |
| GMO positive, soy | 35S + NOS | 11211 + 11212 | 482.5 |
| GMO positive, soy | 35S + NOS | none | 70.5 |

This method greatly reduced the background from the 35S PCR product and permitted better discrimination between the GMO positive and GMO minus DNA samples. Also, this example again demonstrates the utility of the technology for multiplexing both the PCR reaction and the interrogation reaction. As seen in the last four reactions above, the data show that the use of multiple PCR probes and/or multiple interrogation probes leads to identification of GMO organisms.

35S promoter PCR primers:

35S-1 5' GATAGTGGGATTGTGCGTCA 3'    SEQ ID NO:44

35S-2 5' GCTCCTACAAATGCCATCA 3'    SEQ ID NO:45

NOS terminator PCR primers

NOS-1 5' TTATCCTAGTTTGCGCGCTA 3'    SEQ ID NO:46

NOS-2 5' GAATCCTGCTGCCGGTCTTG 3'    SEQ ID NO:47

35S Interrogation oligonucleotide probes:

11211 5' GCAAGTGGATTGATG 3'    SEQ ID NO:48

11210 5' CCAACCACGTCTTCAAA 3'    SEQ ID NO:49

NOS Interrogation oligonucleotide probes 11212 5' TTTATGAGATGGGTTT 3'    SEQ ID NO:50

11213 5' ATGATTAGAGTCCCG 3'    SEQ ID NO:51

EXAMPLE 15
HPLC Separation of dNTPs After Interrogation Assay, but Prior to Phosphate Transfer and Light Production Large-volume pyrophosphorylation assays were performed on matched and mismatched probe/target hybrids. The released nucleotides were separated by high performance liquid chromatography (HPLC) and their fractions collected. NDPK terminal phosphate transfer reactions were performed on these concentrated fractions and luciferase assays conducted to illustrate discrimination between the original matched and mismatched hybrid treated samples.

Target/probe hybrids were formed by combining 315 ng of the synthetic wild type CMV target oligonucleotide with either 10.5 µg wild type CMV probe for a matched hybrid, or 10.5 µg mutant CMV probe for a mismatched hybrid, and adding water to a final volume of 200 µL. The oligonucleotides were CV 12 (SEQ ID NO:2), CV 15 (SEQ ID NO:5), and CV 16 (SEQ ID NO:6), as previously described in Example 1. These solutions were heated to 95° C. for at least 5 minutes, then cooled at room temperature for at least 10 minutes.

The following master mix was prepared.
337.5 μL Nanopure water (Promega, AA399)
90.0 μL 10× DNA Polymerase buffer (Promega, M195A)
11.25 μL 40 mM NaPPi (Promega, C113)

Master mix (210 μL) was added to each of the above hybrid solutions and 5.8 units of Klenow exo– (Promega, M218A) were added to each. The solutions were then incubated at 37° C. for 15 minutes and stored on ice. HPLC separation of the dNTPs was performed.

HPLC separation of DATP, dCTP, dGTP and TTP was performed on a 100×4.6 mm, 3μ Luna C18 column [Perrone and Brown, *J. Chromatography,* 317:301–310 (1984)] from Phenomenex. The column was eluted with a linear gradient of 97 percent buffer A (100 mM triethylammonium acetate, pH 7) to 92 percent buffer A over a period of 12 minutes. The composition of buffer B is 80:20 acetonitrile:35 mM triethylammonium acetate. Detection was monitored by absorbance at 250, 260 and 280 nm. Under these conditions, dCTP was found to elute between 4 and 4.5 minutes, TTP and dGTP eluted as two peaks between 7 and 7.5 minutes, and dATP eluted from 9 to 9.5 minutes.

The fractions containing the free dNTPs were collected and lyophilized. Fraction one contained dCTP, fraction two contained dGTP and TTP, and fraction three contained dATP.

Each fraction was reconstituted in 100 μL of nanopure water. Ten microliters of each fraction, or 10 μL of water as a control, were added to a 10 μL mixture of water, 10× DNA Polymerase Buffer, and ADP so that the final concentration was 1× DNA pol buffer and 0.1 μM ADP. NDPK (0.005 units) was added to each tube in one set of the tubes and an equal amount of water was added to each tube in the other set of tubes. Samples and controls were incubated at 37° C. for 15 minutes, 10 μL added to 100 μL of L/L reagent and the light output was measured on a Turner® TD10/20 luminometer. The relative light units (rlu) results obtained are shown below:

| Sample | Trial 1 | Trial 2 | Trial 3 | Avg rlu |
|---|---|---|---|---|
| Matched hybrid with NDPK | | | | |
| Fraction 1 | 206.6 | 200.6 | 205.9 | 204.4 |
| Fraction 2 | 839.4 | 851.6 | 833.9 | 841.6 |
| Fraction 3 | 1149.0 | 1150.0 | 1169.0 | 1156 |
| Mismatched hybrid with NDPK | | | | |
| Fraction 1 | 101.8 | 97.0 | 98.9 | 99.9 |
| Fraction 2 | 386.1 | 387.3 | 382.2 | 385.2 |
| Fraction 3 | 412.4 | 409.9 | 416.5 | 412.9 |
| Match hybrid without NDPK | | | | |
| Fraction 1 | 6.8 | 6.5 | — | 6.6 |
| Fraction 2 | 10.9 | 11.5 | — | 11.2 |
| Fraction 3 | 33.0 | 37.8 | — | 35.4 |
| Mismatched hybrid without NDPK | | | | |
| Fraction 1 | 6.2 | 6.7 | — | 6.4 |
| Fraction 2 | 8.3 | 8.4 | — | 8.4 |
| Fraction 3 | 13.4 | 13.5 | — | 13.4 |
| No dNTP | 7.9 | 7.5 | — | 7.7 |

As is seen from the above data, the fraction one match:mismatch ratio is 2.1, fraction 2 match:mismatch ratio is 2.2 and fraction 3 match:mismatch ratio is 2.8. The data therefore demonstrate the utility of using HPLC separation of individual nucleotides followed by NDPK conversion to ATP, the preferred substrate of luciferase. Fraction 3 provides a slightly higher match:mismatch ratio owing to the presence of DATP in the nucleotide HPLC fraction. Nevertheless, HPLC separation of identifier nucleotides is useful in the interrogation assays of the present invention.

| | |
|---|---|
| CV12 5' CAACAGACGCTCCACGTTCTTTCTGACG-TATTCGTGCAGCATGGTCTGCGAGCAT-TCGTGGTAGAAGCGAGCT 3' | SEQ ID NO:2 |
| CV15 5' CTACCACGAATGCTCGCAGAC 3' | SEQ ID NO:5 |
| CV16 5' CTACCACGAATGCTCGCAGAT 3' | SEQ ID NO:6 |

EXAMPLE 16
Mass Spectrometry For Nucleotide Detection

The mass spectrometer uses the ratio of molecular mass to charge of various molecules to identify them. Nucleic acids are made up of four different base molecules, each with a different mass to charge ratio. In this example, the capability to use mass spectrometry for separation of the nucleotides that make up DNA is demonstrated.

The ESIMS (Electro Spray Ion Mass spectrometry) spectra of 1 μM and 0.1 μM NTP molecules were determined (Fisons Instruments, VG Platform). The samples were prepared by diluting 1:1 with acetonitrile/water/1% $NH_4OH$. A 20 μL injection was made for each sample. Therefore, 10 picomoles of each DNTP are in the 1 μM sample injection, and 1 picomole of each DNTP is in the 0.1 μM sample injection.

Each of the dNTPs is observed in the 1 μM sample along with the dNTP+$Na^+$ peaks. There was a 485 peak also present, which is an impurity in the system or samples. The peaks for each of the dNTPs are significantly diminished in the 0.1 μM sample; only the DATP peak is above the noise level. Therefore, the difference between the 1 and 0.1 μM samples can be qualitatively determined, which indicates the ability to determine the difference between interrogation samples in which the probe and target are matched and mismatched at the 3'-terminal region of the probe.

EXAMPLE 17
Detection of Human Immunodeficiency Virus (HIV) Drug-resistant Mutants Chemotherapeutic selection pressure in vivo often results in mutations within the genome of the infectious agent that the drug is intended to destroy. This demonstration of evolutionary adaptation is widely reported for human immunodeficiency virus (HIV) under the selective pressure of protease inhibitors or reverse transcriptase inhibitors (Martinez-Picado, *J. Virology,* 73:3744–3752, 1999; Back, *EMBO J.,* 15:4040–4049, 1996).

The first viral mutants to be selected during therapy are typically those with single-amino-acid substitutions. Some of the nucleotides of the HIV reverse transcriptase (RT) and protease genes are known in the art to be "hotspots" for developing such point mutations. Additional mutations accumulate with ongoing therapy. After about 6 months to 1 year of treatment with AZT, HIV typically mutates the RT gene and so becomes resistant to treatment.

The ability to detect and identify such viral mutant genomes in a reliable and sensitive assay would assist with understanding the progression of the infection and with developing the best treatment regimens for infected individuals. Switching to a different treatment course before or as soon as a resistant mutant virus takes hold is important in prolonging patient life.

This example demonstrates that drug resistant mutations that occur within the HIV-1 reverse transcriptase gene, when under the selective pressure of reverse transcriptase inhibitors, such as the nucleoside analog drugs AZT and ddI, can be detected using the process of the invention. Three specific "hotspot" sites of RT mutation were chosen for study. These three mutations all exist within a short region of the RT gene, spanning about 10 amino acids, from codon 65 to 75 of the protein.

Codon 67 (Site 1) of RT changes from GAC to AAC in the presence of the drug AZT, codon 70 (Site 2) changes from AAA to AGA in the presence of AZT, and codon 75 (Site 3) changes from GTA to ATA in the presence of the combination of drugs AZT and ddI. Target oligonucleotides were synthesized to span codons 65 through 81 of the RT genome of HIV-1 strain HXB2 wild type genome as well as oligonucleotides that vary only at one position as defined above for Site 1, Site 2, and Site 3 point mutations. Probe oligonucleotides exactly complementary to the wild type target and to the mutant targets at these three sites were also synthesized. The sequence and names of these oligonucleotides are listed below.

The probe oligonucleotides were dissolved in TE Buffer to a final concentration of 0.5 μg/μL. The target oligonucleotides were dissolved in TE Buffer to a final concentration of 5 μg/mL. One microliter of target was combined with 1 μL of probe and 18 μL of water; and for the controls, 1 μL of each oligonucleotide was combined with 19 μL of water. These solutions were then heated at 95° C. for 3 minutes and cooled at room temperature for 10 minutes. Twenty microliters of master mix were then added to each tube. The master mix is described below.

| Master Mix: | |
| --- | --- |
| 10X DNA Polymerase buffer (Promega M195A) | 120 μL |
| 40 mM Sodium pyrophosphate | 15 μL |
| Klenow exo- enzyme (1 U/μL; Promega M218A) | 15 μL |
| NDPK (1 U/μL) | 6 μL |
| ADP (10 μM) | 12 μL |
| Nanopure water | 432 μL |

The tubes with the master mix added were then incubated for 15 minutes at 37° C. Five microliters of the solutions were then combined with L/L reagent (Promega, F202A) and the light output was measured on a Turner® TD20/20 luminometer. The relative light unit (rlu) data obtained are listed below.

| Solution | Target | Probe | Reading 1 | Reading 2 | Reading 3 |
| --- | --- | --- | --- | --- | --- |
| 1) | 11814 (wt*) | — | 2.55 | 3.82 | 10.78 |
| 2) | 11815 (mut1*) | — | 2.54 | 2.57 | 2.99 |
| 3) | — | 11808 (wt1) | 162.8 | 207.2 | 165.5 |
| 4) | — | 11809 (mut1) | 2.81 | 2.17 | 2.20 |
| 5) | 11816 (mut2) | — | 3.84 | 3.98 | 3.81 |
| 6) | — | 11810 (wt2) | 4.57 | 4.77 | 5.29 |
| 7) | — | 11811 (mut2) | 3.84 | 3.98 | 3.81 |
| 8) | 11817 (mut3) | — | 2.04 | 1.64 | 1.44 |
| 9) | — | 11812 (wt3) | 2.36 | 2.57 | 2.41 |
| 10) | — | 11813 (mut3) | 4.05 | 2.06 | 1.77 |
| 11) | 11814 (wt) | 11808 (wt1) | 418.7 | 711.6 | 682.1 |
| 12) | 11814 (wt) | 11809 (mut1) | 20.69 | 29.05 | 21.25 |
| 13) | 11815 (mut1) | 11808 (wt1) | 218.4 | 185.6 | 118.1 |
| 14) | 11815 (mut1) | 11809 (mut1) | 682.6 | 737.8 | 599.7 |
| 15) | 11814 (wt) | 11810 (wt2) | 1055.0 | 920.2 | 744.7 |
| 16) | 11814 (wt) | 11811 (mut2) | 175.3 | 188.1 | 171.1 |
| 17) | 11815 (mut2) | 11810 (wt2) | 136.9 | 121.0 | 114.4 |
| 18) | 11815 (mut2) | 11811 (mut2) | 822.3 | 865.9 | 729.0 |
| 19) | 11814 (wt) | 11812 (wt3) | 31.49 | 33.22 | 43.83 |
| 20) | 11814 (wt) | 11813 (mut3) | 2.55 | 3.79 | 2.49 |
| 21) | 11815 (mut2) | 11812 (wt3) | 5.26 | 6.00 | 6.33 |
| 22) | 11815 (mut2) | 11813 (mut3) | 77.58 | 78.46 | 82.85 |
| 23) | no DNA | | 2.18 | 2.48 | 1.37 |

*wt = wild type; mut = mutant. wt and mut a, 2, and 3 are defined hereinafter.

All three HIV RT drug-resistance mutations were detectable with discrimination of mutant:wild type rlu ratios ranging from about 3 to about 7. Probe 11808, which is directed to site one and is completely complementary to wild type target, had high background values when tested alone. The other oligonucleotides all had acceptably low levels of background.

Target and Probe Sequences 11808 5' CCATTTAGTACTGTCT 3'   SEQ ID NO:52

HIV WT Probe Site 1

11809 5' CCATTTAGTACTGTTT 3'   SEQ ID NO:53

HIV Mutant Probe Site 1

11810 5' CTAGTTTTCTCCATTT 3'   SEQ ID NO:54

HIV WT Probe Site 2

11811 5' CTAGTTTTCTCCATCT 3'   SEQ ID NO:55

HIV Mutant Probe Site 2

11812 5' TTCTCTGAAATCTACT 3'   SEQ ID NO:56

HIV WT Probe Site 3

11813 5' TTCTCTGAAATCTATT 3'   SEQ ID NO:57

HIV Mutant Probe Site 3

11814 5' AAAAAAGACAGTACTAAATGGAGAAAAC-
TAGTAGATTTCAGAGAACTTAA 3'   SEQ ID NO:58

HIV WT Target 11815 5' AAAAAAAACAGTACTAAATGGAGAAAAC-
TAGTAGATTTCAGAGAACTTAA 3'   SEQ ID NO:59

HIV Mutant Target Site 1

11816 AAAAAAGACAGTACTAGATGGAGAAAAC-
TAGTAGATTTCAGAGAACTTAA 3'  SEQ ID NO:60

HIV Mutant Target Site 2 5'

11817 5'AAAAAAGACAGTACTAAATGGAGAAAAC-
TAATAGATTTCAGAGAACTTAA 3'  SEQ ID NO:61

HIV Mutant Target Site 3

EXAMPLE 18

Detection of E. coli Repetitive Sequence Without Nucleic Acid Amplification

In this example repetitive sequence in E. coli is detected without the need for amplification of the target sequence prior to pyrophosphorylation. This target sequence is denoted as 'colirep'.

Oligonucleotide 11707 (SEQ ID NO:62) is totally complementary to a segment of colirep DNA sequence. Twelve microliters of oligonucleotide 11707 solution (1 mg/mL) were combined with 204 µL of water to make solution A. Another solution was prepared by combining 4 µL of 11707 (1 mg/mL) with 204 µL water and 8 µL 10 mM Tris, pH 8.0 to make solution B. The E. coli is Sigma cat#D4889, E. coli Strain B ultra pure.

Four nanograms (2 µL) E. coli DNA were combined with 18 µL solution A and with 18 µL solution B in separate tubes. Similarly, 40 ng E. coli DNA was combined with 18 µL solution A and with 18 µL solution B in separate tubes. These solutions were then incubated at 92° C. for 3 minutes and cooled at room temperature for 15 minutes. The following master mix was assembled:

| 10X DNA polymerase buffer | 240 µL |
|---|---|
| 40 mM NaPPI | 30 µL |
| Klenow exc- (10 U/µL) | 30 µL |
| NDPK (1 U/µL) | 12 µL |
| 10 µM ADP (Sigma) | 24 µL |
| water | 864 µL |

Twenty microliters of master mix were added to each reaction and they were then incubated at 37° C. for 15 minutes. One hundred microliters of L/L Reagent were then added and the relative light output (rlu) immediately measured with a Turner® TD 20/20 luminometer. The rlu were:

| Solution | rlu-1 | rlu-2 | rlu-3 | Average |
|---|---|---|---|---|
| Tris | 2.85 | 3.562 | 3.059 | 3.157 |
| 11707 (A) | 13.69 | 12.13 | 13.67 | 13.16 |
| 11707 (B) | 7.473 | 7.234 | 6.981 | 7.259 |
| 40 ng DNA + Tris | 75.62 | 75.52 | 73.24 | 74.79 |
| 40 ng DNA + 11707 (A) | 97.71 | 134.2 | 105.1 | 112.3 |
| 40 ng DNA + 11707 (B) | 81.46 | 87.56 | 76.28 | 81.77 |
| 4 ng DNA + Tris | 6.719 | 8.084 | 5.882 | 6.895 |
| 4 ng DNA + 11707 (A) | 24.50 | 25.97 | 25.17 | 25.21 |
| 4 ng DNA + 11707 (B) | 15.69 | 17.22 | 16.99 | 16.63 |

The data reflect that oligonucleotide probe 11707 can detect E. coli DNA without amplification by a process of the invention.

Interrogation oligonucleotide:

11707 5' AGTGACTGGGG 3'  SEQ ID NO:62

EXAMPLE 19

Digestion of PhiX 174 HinF1 Fragments

Polynucleotides encountered in nature are often double stranded. The DNA fragments generated by digestion of PhiX 174 DNA using endonuclease HinFI are double-stranded DNA fragments of various sizes. In order to test whether double stranded DNA could be detected, PhiX 174 DNA was directly used as a target nucleic acid substrate or digested with nucleases to produce nucleotides that could be converted to nucleoside triphosphates as in previous examples.

The following conditions were used to digest DNA fragments from bacteriophage PhiX 174. The following materials were placed in three 1.5 mL polypropylene tubes: 50 µL of PhiX 174 HinFI fragments (Promega G175A, Lot #773603); 40 µL 5 mM MgSO$_4$; 5 µL Exo III buffer (10×) (Promega E577B, 4853216), and 5 µL Nanopure water. Fifty microliters TE buffer and 40 µL 5 mM MgSO$_4$; 5 µL ExoIII buffer (10×) and 5 µL Nanopure water were added to one sample. Two of the samples containing PhiX 174 DNA were further treated with 2 µL Exo III (Promega M181A, 5512708) and the tubes placed in a 37° C. water bath for 60 minutes. ExoIII was also added to the sample without DNA and the sample incubated at 37° C. 60 minutes.

At this time, 800 µL Nanopure water and 100 µL (10×) S1 Nuclease Buffer (Promega, M577A, Lot #6748605) were added to all samples. Three microliters S1 nuclease (Promega, E576B, Lot #789881) were then added to all samples. All samples were incubated at 37° C. for 30 minutes.

Two hundred microliters from each of the three tubes containing DNA were diluted with 300 µL 1× TE Buffer and the absorbance read at 260 nm using a Beckman DU 650 spectrophotometer. The readings recorded were: tube one (no nuclease addition), 0.3073; tube two (treatment with Exo III), 0.5495; tube three (treatment with Exo III and S1), 0.5190. The increased absorbance values of the tubes treated with nuclease indicate that the polymer was digested. These digests were subsequently used in other studies (see Example 22, below).

EXAMPLE 20

Self-annealing Interrogation Probe

This example illustrates use of a different type of oligonucleotide probe that is used to form a hairpin structure in the interrogation technology of this invention. This study demonstrates a method for eliminating the need for adding a probe specific to the interrogation site to the interrogation reaction.

Here, the oligonucleotide probe anneals to the target strand downstream of (3' to) the interrogation position in the target strand. The oligonucleotide has at its 5' end an unannealed region of nucleotides followed by about 5 to about 20 nucleotides that are identical to the interrogation region on the target strand. The annealed 3' end of the oligonucleotide is then extended through the interrogation position of the target strand creating what is referred to as extended probe. The hybrid is denatured and a hairpin structure formed between the extended probe strand and the 5' end of the oligonucleotide probe. This region is then assayed in a standard interrogation reaction to determine if a mismatch is present or not.

Four probes were designed to represent different types of hairpin formations that an extended probe strands may assume. These probes are 10207 (SEQ ID NO:63), 10208 (SEQ ID NO:64), 10209 (SEQ ID NO:65), and 10212 (SEQ ID NO:66).

These probes are predicted to form the following self-hybridized secondary structures when allowed to self-anneal:

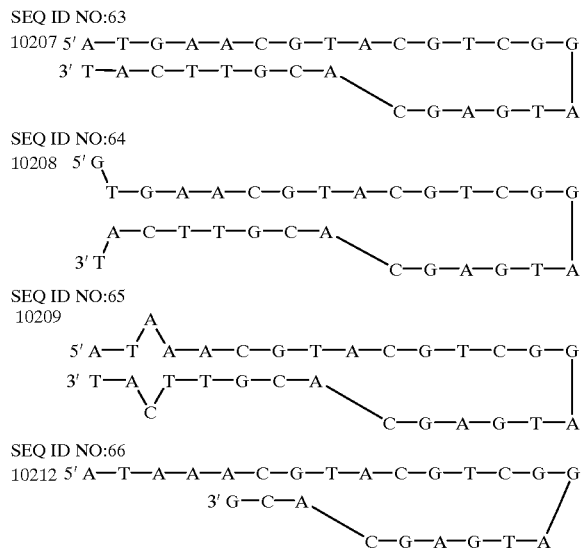

A 5 µL (5 µg) aliquot of each of the four probes was diluted to 100 µL with nanopure water. They were then sequentially diluted 1:10 to a final dilution factor of 1:100,000. Twenty microliters of the diluted probes were heated, in separate tubes, at 95° C. for 3 minutes and cooled to room temperature for 10 minutes to permit self-annealing. Twenty microliters of Master Mix, as described in Example 1, were then added to each tube and the tubes were incubated at 37° C. for 15 minutes. Ten microliters of the solutions were added to 100 µL of L/L reagent (Promega, F202A) and relative light units measured immediately with a Turner® TD20/20 luminometer. The no-probe control resulted in 57.24 relative light units and the remaining probe results are reported below in relative light units (rlu).

| Log dilution | Probe | | | |
|---|---|---|---|---|
| | 10207 | 10208 | 10209 | 10212 |
| −5 | 44.89 | 56.22 | 57.57 | 57.80 |
| −4 | 85.21 | 64.56 | 58.26 | 63.15 |
| −3 | 297.7 | 70.53 | 79.12 | 82.65 |
| −2 | 970.5 | 108.4 | 80.06 | 106.7 |

Probe 10207 worked as an efficient target for interrogation as expected, with probe 10208 providing the anticipated negative results. Probe 10212 has only a three base match so it may be unextended, thus resulting in the low values. Probe 10209 likely has the 3' terminal nucleotide unannealed when the hairpin forms due to the mismatch at the third nucleotide in from the 3' end. Such an unannealed 3' terminal nucleotide would account for the low rlu values.

10207 5' ATGAACGTACGTCGGATGAGCACG-
TTCAT 3'  SEQ ID NO:63

10208 5' GTGAACGTACGTCGGATGAGCACG-
TTCAT 3'  SEQ ID NO:64

10209 5' ATAAACGTACGTCGGATGAGCACG-
TTCAT 3'  SEQ ID NO:65

10212 5' ATAAACGTACGTCGGATGAGCACG 3' SEQ ID NO:66

EXAMPLE 21

Interrogation With a Self-annealing Primer

This example and FIG. 2 illustrate use of a different type of oligonucleotide probe, a "REAPER™" probe in a process of this invention. This example demonstrates a method for eliminating the need for adding a probe specific to the interrogation site to the interrogation reaction.

Here, the oligonucleotide first probe (SEQ ID NO:68), at its 3'-end, anneals to the target strand (SEQ ID NO:67) at a position downstream of (3' to) the interrogation position in the target strand (FIG. 2A). The probe has at its 5'-end an unannealed region of nucleotides including about 5 to about 20 nucleotides that are identical to a region on the target strand including the interrogation position. This region of identity is present in the same orientation on both the target and the probe strands.

The annealed 3'-end of the probe is then extended through the interrogation position of the target strand forming what is referred to as a first extended probe and an extended first hybrid as is illustrated in FIG. 2B (SEQ ID NO:69). The extended first hybrid is denatured and a second probe (SEQ ID NO:70) is annealed to the first extended probe to form a second hybrid. This second probe is complementary to the first extended probe strand at a region downstream of the interrogation position on the first extended probe strand (FIG. 2C).

The second probe is then extended and a second extended hybrid is formed as illustrated in FIG. 2D. The second extended hybrid is comprised of the first extended probe and second extended probe (SEQ ID NO:71).

The strands of the second extended hybrid are denatured and permitted to renature to form a hairpin structure. Upon hairpin formation, the first extended probe forms a hairpin structure that has a 3'-overhang, whereas the second extended probe forms a hairpin structure that contains a 5'-overhang that provides a substrate for depolymerization. The second extended probe strand is then depolymerized and the analytical output obtained as described elsewhere herein. The analytical output determines the presence or absence of the original target strand or of a particular base in the original target strand as is also discussed elsewhere herein.

SEQ ID NO:67 oligonucleotide is diluted to 1 mg/mL in water. SEQ ID NO:70 oligonucleotide is diluted to 1 mg/mL in water. One microliter of each solution is combined with 18 µL water. The solution is heated to 95° C. for 5 minutes then is cooled at room temperature for 10 minutes to permit oligonucleotides of SEQ ID NOs:67 and 70 to anneal.

To this solution are added dNTP mixture to a final concentration of 0.25 mM for each dNTP, 10x Klenow buffer to a final concentration of 1x, and 5 U of Klenow enzyme. The tube with these components is incubated at 37° C. for 30 minutes. The extended first hybrid DNA so formed (containing SEQ ID NO: 69) is purified (Qiagen, Mermaid system) and eluted into 50 µl of water.

To this solution of the purified extended first hybrid is added 1 µl SEQ ID NO: 70 oligonucleotide (1 mg/mL) as second probe. The solution is then heated to 95° C. for 5 minutes and is cooled at room temperature to permit 69 and 70 to anneal as illustrated in FIG. 2C to form the second hybrid. To this solution are added a dNTP mixture to a final concentration of 0.25 mM for each DNTP, 10x Klenow buffer to a final concentration of 1x, and 5 U of Klenow enzyme. The tube with these components is incubated at 37° C. for 30 minutes to form a second extended hybrid that contains a second extended probe (oligonucleotide SEQ ID NO: 71).

The SEQ ID NO: 71/69 second extended hybrid DNA (FIG. 2D) formed is purified (Qiagen, Mermaid system) to separate the extended hybrid from the unreacted dNTPs and eluted into 50 μl water. (Alternatively, the original 68 oligo is biotinylated at it's 5'-end and this biotin is then also present in strand of SEQ ID NO: 69. This biotinylated strand 69 is then denatured from strand 71 and removed from the solution with streptavidin coated paramagnetic particles according to the manufacturer's instructions (Promega, Z5481) and the 71 hairpin structure is allowed to form as below).

This hybrid solution is then heated to 95° C. for 5 minutes diluted to 100 μl with water and is cooled on ice for 10 minutes to permit hairpin structure formation.

The following master mix is assembled and mixed.

| Component | Amount |
|---|---|
| 10X DNA Pol Buffer (Promega, M195A) | 200 μL |
| Klenow exo- (1 U/μL) (Promega M218B) | 12.5 μL |
| 40 mM Sodium Pyrophosphate (Promega C350B) | 25 μL |
| NDPK (1 U/μL) | 10 μL |
| 10 uM ADP (Sigma A5285) | 20 μL |
| Water | 732.5 μL |

Twenty microliters of this master mix are added to 20 μL of the above hairpin-containing solutions after cooling, and the resulting mixtures are heated at 37° C. for 15 minutes. After this incubation, duplicate 4 μL samples of the solution are removed, added to 100 μL of L/L Reagent (Promega, F202A) and the light produced by the reaction is measured immediately using a Turner® TD20/20 luminometer. A positive analytical output at levels over background (no enzyme) indicates that a matched base was present at the 3'-terminus of the hairpin structure and this further indicates the presence of the target strand, and for this particular example, it also indicates the presence of a G base at the interrogation position of the target.

5' CCGGAGAGACCTCCTTAAGGGGCCATAT-
TATTTCGTCGATTCCAGTGTTGGCCAAA-
CGGAT 3'  SEQ ID NO: 67

5' GGGGCCATATTATTTCGCCGTTTGGC-
CAACACTGGAATCGA 3'  SEQ ID NO: 68

5' GGGGCCATATTATTTCGCCGTTTGGC-
CAACACTGGAATCGACGAAATAATATG-
GCCCCTTAAGGAGGTCTCTCCGGG 3'  SEQ ID NO: 69

5' CCGGAGAGACCTCCT 3'  SEQ ID NO: 70

5' CCGGAGAGACCTCCTTAAGGGGCCATAT-
TATTTCGTCGATTCCAGTGTTGGC-
CAAACGGCGAAATAATATGGCCCC 3'  SEQ ID NO: 71

EXAMPLE 22

Detection of PhiX 174 HinF1 Fragments Using Nucleases, PRPP Synthetase, NDPK

This example demonstrates the detection of DNA by digestion of the polymer to nucleoside monophosphates using nucleases, transformation of the nucleoside monophosphates to nucleoside triphosphates using PRPP Synthetase and PRPP along with transformation of ADP to ATP using the nucleoside triphosphates generated by the action of PRPP Synthetase, and detection of the ATP using luciferase. A sample of deoxynucleotide (Poly (dA)) was prepared as described in Example 19. Different amounts of deoxynucleotide were used in the reactions as presented in Table 30.

The following additions were made to each reaction: 2 μL PRPP, 2 μL PRPP Synthetase, and 20 μL PRPP Synthetase buffer. The reactions proceeded at 37° C. for 28 minutes, at which time the reactions were transferred to 100 μl LAR Buffer containing 2 μL ADP and 2 μL NDPK. This second reaction was permitted to proceed at at room temperature for 20 minutes. The amount of ATP produced was measured by the addition of 10 ng of luciferase followed by measuring light output with a luminometer. The data are presented in table below. These data show that this combination of enzymes permitted detection of DNA.

| Reaction | Nucleotide | Amount in Reaction | Light Units |
|---|---|---|---|
| 1 | dAMP | 200 ng, 600 pmoles | 1018 |
| 2 | dAMP | 20 ng, 60 pmoles | 636 |
| 3 | dAMP | 2 ng, 6 pmoles | 178 |
| 4 | dAMP | 200 pg, 600 fmoles | 83 |
| 5 | none | zero ng | 69 |
| 6 | PhiX 174 only | 100 ng (= 300 pmoles dNMP; about 75 pmoles dAMP) | 46 |
| 7 | PhiX 174 + ExoIII | 100 ng | 472 |
| 8 | PhiX 174 + Exo + S1 | 100 ng | 448 |
| 9 | No DNA + Exo + S1 | zero ng | 55 |

EXAMPLE 23

Comparison of Thermophilic DNA Polymerases in a One-step 70° C. Interrogation Reaction In this example, four different thermophilic DNA polymerases were used along with the thermophilic NDPK from Pfu in an interrogation reaction. The polymerases used were Taq (Promega, M166F), Pfu (*Pyrococcus furiosus* strain Vcl DSM3638, Promega, M774A), Tvu (*Thermoactinomyces vulgaris*, purified at Promega), and Ath (*Anaeocellum thermophilum*, purified at Promega).

Cytomegalovirus (CMV) synthetic targets were generated by combining wild type oligonucleotide primers 9162 (SEQ ID NO:72) and 9165 (SEQ ID NO:73) or mutant oligonucleotide primers 9163 (SEQ ID NO:74) and 9166 (SEQ ID NO:75). The interrogation oligonucleotides used were wild type sequence 9211 (SEQ ID NO:35) and mutant sequence 9212 (SEQ ID NO:36).

Five nanograms of either the wild type or the mutant target (2.5 ng each of 9162 and 9165 for wild type or 9163 and 9166 for mutant) were combined with 1 μg of either the wild type probe, the mutant probe, or no probe, and water to a final volume of 20 μL. The solutions were heated for 5 minutes at 95° C. then cooled for 10 minutes at room temperature. Twenty microliters of 2× master mix were then added to each solution, and each was further incubated at 70° C. for 10 minutes. Four microliters of each solution were added to 100 μL of L/L Reagent (Promega F202A) and the relative light units (rlu) measured on a Turner® TD20/20 luminometer. The various combinations of target and probe assayed and their average resulting rlu values, corrected for background values, from duplicate solutions are listed below.

2× Master Mix

| | |
|---|---|
| 100 μL | 10X Thermophilic DNA polymerase buffer (Promega, M190A) |
| 100 μL | 15 mM MgCl₂ (Promega, A351B) |
| 25 μL | 40 mM NaPPi (Promega, E350B) |
| 10 μL | 10 μM ADP (Sigma, A-5285) |
| 5 μL | Thermophilic polymerase (1 U enzyme/reaction) |
| 5 μl | Pfu NDPK (0.5 U/μL) (see Example 25 for enzyme purification; 0.1 U/rxn)) |
| 275 μL | water |

| Polymerase | Target | Probe | rlu | match:mismatch ratio |
|---|---|---|---|---|
| Taq | wild type | wild type | 129 | 128:1 |
| | wild type | mutant | −2 | |
| | mutant | mutant | 62 | 95:1 |
| | mutant | wild type | 0.65 | |
| Pfu | wild type | wild type | 121 | 20:1 |
| | wild type | mutant | 6 | |
| | mutant | mutant | 34 | 1:2 |
| | mutant | wild type | 54 | |
| Tvu | wild type | wild type | 898 | 89:1 |
| | wild type | mutant | 10 | |
| | mutant | mutant | 1075 | 66:1 |
| | mutant | wild type | 16 | |
| Ath | wild type | wild type | 327 | 327:1 |
| | wild type | mutant | 0 | |
| | mutant | mutant | 244 | 136:1 |
| | mutant | wild type | 1.8 | |

9162 5' GTGTATGCCACTTTGATATTACACCCAT-
GAACGTGCTCATCGACGTCAACCCGCAC-
AACGAGCT 3'                                    SEQ ID NO:72

9165 5' GTTGTGCGGGTTCACGTCGATGAG-
CACGTTCATGGGTGTAATATCAAAGTG-
GCATACACGAGCT 3'                               SEQ ID NO:73

9163 5' GTGTATGCCACTTTGATATTACACCCGT-
GAACGTGCTCATCGACGTCAACCCGCACA-
ACGAGCT 3'                                     SEQ ID NO:74

9166 5' GTTGTGCGGGTTCACGTCGATGAG-
CACGTTCACGGGTGTAATATCAAAGTG-
GCATACACGAGCT 3'                               SEQ ID NO:75

9211 5' ACTTTGATATTACACCCA-
TG 3' (wild type primer)                       SEQ ID NO:35

9212 5' ACTTTGATATTACACCC-
GTG 3' (mutant primer)                         SEQ ID NO:36

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for determining the presence or absence of a predetermined exogenous nucleic acid target sequence in a nucleic acid sample that comprises the steps of:
   (A) providing a treated sample that may contain said predetermined exogenous nucleic acid target sequence hybridized with a nucleic acid probe that includes an identifier nucleotide in the 3'-terminal region;
   (B) admixing the treated sample with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;
   (C) maintaining the treated reaction mixture for a time period sufficient to permit the enzyme to depolymerize hybridized nucleic acid and release identifier nucleotides therefrom; and
   (D) analyzing for the presence of released identifier nucleotides to obtain an analytical output, the analytical output indicating the presence or absence of said exogenous nucleic acid target sequence.

2. The method according to claim 1 wherein said identifier nucleotide is a nucleoside triphosphate.

3. The method according to claim 1 wherein said analytical output is obtained by luminescence spectroscopy.

4. The method according to claim 1 wherein said analytical output is obtained by fluorescence spectroscopy.

5. The method according to claim 1 wherein said analytical output is obtained by mass spectrometry.

6. The method according to claim 1 wherein said analytical output is obtained by absorbance spectroscopy.

7. The method according to claim 1 including the further steps of forming said treated sample by
   (A) admixing a sample to be assayed with one or more nucleic acid probes to form a hybridization composition, wherein the 3'-terminal region of said nucleic acid probes (i) hybridize with partial or total complementarity to said exogenous nucleic acid target sequence when that sequence is present in the sample and (ii) include an identifier nucleotide;
   (B) maintaining said hybridization composition for a time period sufficient to form a treated sample that may contain said one predetermined exogenous nucleic acid target sequence hybridized with a nucleic acid probe.

8. The method according to claim 1 wherein said nucleic acid sample is obtained from a biological sample.

9. The method according to claim 8 wherein said predetermined exogenous nucleic acid target sequence is a microbial or viral nucleic acid.

10. The method according to claim 9 wherein said predetermined exogenous nucleic acid target sequence is a viral nucleic acid and the magnitude of the analytical output from a predetermined amount of said biological fluid provides a measure of the viral load in the biological sample.

11. The method according to claim 1 wherein said nucleic acid sample is obtained from a food source.

12. The method according to claim 11 wherein said food source is a plant.

13. The method according to claim 12 wherein said predetermined exogenous nucleic acid target sequence is a sequence non-native to the genome of said plant.

14. The method according to claim 13 wherein said sequence non-native to the genome of said plant is a transcription control sequence.

15. The method according to claim 14 wherein said transcription control sequence is that of the 35S promoter or the NOS terminator.

16. The method according to claim 7 including the further steps of preparing a nucleic acid sample to be assayed by amplifying an exogenous nucleic acid sequence from a crude nucleic acid sample.

17. A method for determining the presence or absence of at least one predetermined exogenous nucleic acid target sequence in a nucleic acid sample that comprises the steps of:
   (A) admixing a sample to be assayed with one or more nucleic acid probes to form a hybridization composition, wherein the 3'-terminal region of said nucleic acid probes (i) hybridizes with partial or total complementarity to at least one said predetermined exogenous nucleic acid target sequence when that sequence is present in the sample and (ii) includes an identifier nucleotide;
   (B) maintaining said hybridization composition for a time period sufficient to form a treated sample that may contain said predetermined exogenous nucleic acid target sequence hybridized with a nucleic acid probe;
   (C) admixing the treated sample with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;
   (D) maintaining the treated reaction mixture for a time period sufficient to permit the enzyme to depolymerize hybridized nucleic acid and release identifier nucleotides therefrom; and
   (E) analyzing for the presence of released identifier nucleotides to obtain an analytical output, the analytical output indicating the presence or absence of at least one said exogenous nucleic acid target sequence.

18. The method according to claim 17 wherein said identifier nucleotide is a nucleoside triphosphate.

19. The method according to claim 17 wherein said analytical output is obtained by luminescence spectroscopy.

20. The method according to claim 17 wherein said analytical output is obtained by fluorescence spectroscopy.

21. The method according to claim 17 wherein said analytical output is obtained by mass spectrometry.

22. The method according to claim 17 wherein said analytical output is obtained by absorbance spectroscopy.

23. A method for determining the presence or absence of an exogenous nucleic acid target sequence containing an interrogation position in a nucleic acid sample that comprises the steps of:
   (A) providing a treated sample that contains a nucleic acid sample that may include said exogenous nucleic acid target sequence hybridized with a nucleic acid probe that is comprised of three sections, (i) a first section that contains the probe 3'-terminal about 10 to about 30 nucleotides that are complementary to the exogenous nucleic acid target sequence at positions beginning about 1 to about 30 nucleic acids downstream of said interrogation position of the target sequence, (ii) a 5'-terminal region of about 10 to about 200 nucleic acids in length and having the identical sequence of said exogenous nucleic acid target sequence, and (iii) an optional third section that contains zero to about 50 nucleic acids that are not complementary to said nucleic acid sample, and;
   (B) extending said nucleic acid probe in a 3' direction to form a second probe hybridized to the nucleic acid sample as a second hybrid;

(D) denaturing said second hybrid to separate said second probe from said exogenous nucleic acid target sequence;

(E) renaturing said aqueous composition to form hairpin structures from said second probe;

(F) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes pyrophosphorolysis;

(G) maintaining the treated reaction mixture for a time period sufficient to permit the enzyme to depolymerize hybridized nucleic acid and release one or more nucleotides from the 3'-terminus therefrom; and (H) analyzing for the presence of released identifier nucleotide to obtain an analytical output, the analytical output indicating the presence or absence of said exogenous nucleic acid target sequence.

24. A method for determining the presence or absence of an exogenous nucleic acid target sequence, or a specific base within the said target sequence, in a nucleic acid sample, that comprises the steps of:

(A) providing a treated sample that contains a nucleic acid sample that may include an exogenous nucleic acid target sequence hybridized with a first nucleic acid probe as a first hybrid, said first probe being comprised of at least two sections, a first section containing the probe 3'-terminal about 10 to about 30 nucleotides that are complementary to the target nucleic acid sequence at a position beginning about 5 to about 30 nucleotides downstream of the target interrogation position, a second section of the first probe containing about 5 to about 30 nucleotides that are a repeat of the target sequence from the interrogation position to about 10 to about 30 nucleotides downstream of the interrogation position that does not hybridize to said first section of the probe, and an optional third section of the probe located between the first and second sections of the probe that is zero to about 50 nucleotides in length and comprises a sequence that does not hybridize to either the first or second section of the probe;

(B) extending the first hybrid in the treated sample at the 3'-end of the first probe, thereby extending the first probe past the interrogation position and forming an extended first hybrid that includes an interrogation position;

(C) denaturing an aqueous composition of the extended first hybrid to separate the two nucleic acid strands and form an aqueous composition containing a separated target nucleic acid and a separated extended first probe;

(D) annealing to the extended first probe a second probe that is about 10 to about 30 nucleotides in length and is complementary to the extended first probe at a position beginning about 5 to about 2000 nucleotides downstream of the interrogation position in the extended first probe, thereby forming a second hybrid;

(E) extending the second hybrid at the 3'-end of the second probe until that extension reaches the 5'-end of the extended first probe, thereby forming a second extended hybrid containing a second extended probe whose 3'-region includes an identifier nucleotide;

(F) denaturing an aqueous composition of the extended second hybrid to separate the two nucleic acid strands and form an aqueous composition containing separated extended first and second probes;

(G) cooling the aqueous composition to form a hairpin structure from the separated extended second probe to form a hairpin structure-containing composition;

(H) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes pyrophosphorolysis;

(I) maintaining the reaction mixture for a time period sufficient to release 3'-terminal region identifier nucleotides; and (J) analyzing for the presence of released identifier nucleotide to obtain an analytical output, the analytical output indicating the presence or absence of said predetermined exogenous nucleic acid target sequence or a specific base within the target sequence.

25. The method according to claim 24 wherein said analytical output is obtained by luminescence spectroscopy.

26. The method according to claim 24 wherein said analytical output is obtained by fluorescence spectroscopy.

27. The method according to claim 24 wherein said analytical output is obtained by mass spectrometry.

28. The method according to claim 24 wherein said analytical output is obtained by absorbance spectroscopy.

29. A method for determining the presence or absence of a specific base in an exogenous nucleic acid target sequence in a sample to be assayed that comprises the steps of:

(A) admixing a sample to be assayed with one or more nucleic acid probes to form a hybridization composition, wherein the 3'-terminal region of at least one of said nucleic acid probes (i) is substantially complementary to said nucleic acid target sequence and comprises at least one predetermined nucleotide at an interrogation position, and (ii) includes an identifier nucleotide, and wherein said nucleic acid target sequence comprises at least one specific base whose presence or absence is to be determined;

(B) maintaining said hybridization composition for a time period sufficient to form a treated sample, wherein said interrogation position of the probe is a nucleotide that is aligned with said specific base to be identified in said target sequence, when present, so that base pairing can occur;

(C) admixing the treated sample with an enzyme whose activity is to release one or more nucleotides from the 3'-terminus of a hybridized nucleic acid probe to depolymerize the hybrid and form a treated reaction mixture, wherein said enzyme catalyzes pyrophosphorolysis;

(D) maintaining the treated reaction mixture for a time period sufficient to release an identifier nucleotide therefrom; and (E) analyzing for the presence or absence of released identifier nucleotide to obtain an analytical output that indicates the presence or absence of said specific base to be identified.

30. The method according to claim 29 wherein the identifier nucleotide is at the interrogation position.

31. The method according to claim 29 wherein said analytical output is obtained by fluorescence spectroscopy.

32. The method according to claim 29 wherein said analytical output is obtained by mass spectrometry.

33. The method according to claim 29, wherein said nucleic acid target sequence is selected from the group consisting of deoxyribonucleic acid and ribonucleic acid.

34. The method according to claim 33, further comprising a first probe, a second probe, a third probe and a fourth probe.

35. A one-pot method for determining the presence or absence of at least one predetermined exogenous nucleic acid target sequence in a nucleic acid sample that comprises the steps of:
- (A) admixing a treated sample that may contain said predetermined nucleic acid target sequence hybridized to a nucleic acid probe whose 3'-terminal region is completely complementary to said predetermined nucleic acid target sequence and includes an identifier nucleotide with (i) a depolymerizing amount of an enzyme whose activity in the presence of pyrophosphate is to release identifier nucleotide as a nucleoside triphosphate from the hybridized nucleic acid probe, (ii) adenosine 5' diphosphate, (iii) pyrophosphate and (iv) NDPK to form a treated reaction mixture;
- (B) maintaining the treated reaction mixture at a temperature of about 25 to about 80 degrees C. for a time period sufficient to permit the enzyme to depolymerize hybridized nucleic acid probe, release an identifier nucleotide in the 3'-terminal region as a nucleoside triphosphate and to convert said nucleoside triphosphate and said adenosine 5' diphosphate to adenosine 5' triphosphate; and
- (C) analyzing for the presence of adenosine 5' triphosphate to obtain an analytical output, the analytical output indicating the presence or absence of at least one said nucleic acid target sequence.

36. The method according to claim 35 wherein said analytical output is obtained by luminescence spectroscopy.

37. The method according to claim 35 including the further steps of forming said treated sample by (A) admixing a sample to be assayed with one or more nucleic acid probes to form a hybridization composition, wherein the 3'-terminal region of said nucleic acid probe (i) hybridizes with partial or total complementarity to a nucleic acid target sequence when that sequence is present in the sample and (ii) includes an identifier nucleotide;
- (B) maintaining said hybridization composition for a time period sufficient to form a treated sample that may contain said one predetermined nucleic acid target sequence hybridized with a nucleic acid probe.

38. The method according to claim 35 wherein said depolymerizing enzyme maintains activity at 60–90° C.

39. The method according to claim 38 wherein said depolymerizing enzyme is a thermostable polymerase.

40. The method according to claim 35 wherein said NDPK is that encoded by *Pyrococcus furiosis*.

41. A method for determining the presence or absence of a first exogenous nucleic acid target in a nucleic acid sample containing that target or a substantially identical second exogenous target that comprises the steps of:
- (A) admixing said sample to be assayed with one or more nucleic acid probes to form a hybridization composition, wherein said first and second exogenous nucleic acid targets comprise a region of sequence identity except for at least a single nucleotide at a predetermined position that differs between the targets, and wherein said nucleic acid probe (i) is substantially complementary to said nucleic acid target region of sequence identity and comprises at least one nucleotide at an interrogation position, said interrogation position of the probe being aligned with said predetermined position of a target when a target and probe are hybridized and (ii) includes an identifier nucleotide in the 3'-terminal region;
- (B) maintaining said hybridization composition for a time period sufficient to form a treated sample wherein the nucleotide at said interrogation position of said probe is aligned with the nucleotide at said predetermined position of said target in said region of identity;
- (C) admixing the treated sample with a depolymerizing amount an enzyme whose activity is to release one or more nucleotides from the 3'-terminus of a hybridized nucleic acid probe to form a treated reaction mixture, wherein said enzyme catalyzes pyrophosphorolysis;
- (D) maintaining the treated reaction mixture for a time period sufficient to release identifier nucleotide and depolymerize said hybridized nucleic acid probe; and
- (E) analyzing for the presence of released identifier nucleotide to obtain an analytical output, said analytical output indicating the presence or absence of said nucleotide at said predetermined region and thereby the presence or absence of a first or second exogenous nucleic acid target.

42. The method according to claim 41 wherein said analytical output is obtained by fluorescence spectroscopy.

43. The method according to claim 41 wherein said analytical output is obtained by mass spectrometry.

44. The method according to claim 41 wherein said analytical output is obtained by luminescence spectroscopy.

45. The method according to claim 41 wherein said analytical output is obtained by absorbance spectroscopy.

46. The method according to claim 41 wherein said nucleic acid target sequence is selected from the group consisting of deoxyribonucleic acid and ribonucleic acid.

47. The method according to claim 41 further comprising a first probe and a second probe.

48. The method according to claim 47 wherein said sample to be assayed comprises a plurality of first nucleic acid targets and second substantially identical nucleic acid targets.

49. The method according to claim 48 wherein said first probe comprises a nucleotide at said interrogation position that is complementary to a first target nucleic acid at said predetermined position, and said second probe comprises a nucleotide at the interrogation position that is complementary to a second target nucleic acid at said predetermined position.

50. The method according to claim 48 wherein the analytical output obtained when one of said nucleic acid probes hybridizes with partial complementarity to one target nucleic acid sequence is less than the analytical output when all of the nucleic acid probes hybridize with total complementarity to their respective nucleic acid target sequences.

51. The method according to claim 48 wherein the analytical output obtained when one of said nucleic acid probes hybridizes with total complementarity to one nucleic acid target sequence is greater than the analytical output when all of the nucleic acid probes hybridize with partial complementarity to their respective nucleic acid target sequences.

* * * * *